US010081790B2

(12) United States Patent
Stewart et al.

(10) Patent No.: US 10,081,790 B2
(45) Date of Patent: Sep. 25, 2018

(54) *BACILLUS* BASED DELIVERY SYSTEM AND METHODS OF USE

(71) Applicant: The Curators of the University of Missouri, Columbia, MO (US)

(72) Inventors: George C. Stewart, Columbia, MO (US); Brian Matthew Thompson, Creve Coeur, MO (US); Chung-Ho Lin, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 14/849,295

(22) Filed: Sep. 9, 2015

(65) Prior Publication Data
US 2016/0053222 A1 Feb. 25, 2016

Related U.S. Application Data

(62) Division of application No. 13/089,015, filed on Apr. 18, 2011, now Pat. No. 9,132,175.

(51) Int. Cl.
| | |
|---|---|
| *C12P 7/10* | (2006.01) |
| *C12N 1/20* | (2006.01) |
| *C12P 3/00* | (2006.01) |
| *C12R 1/085* | (2006.01) |
| *C02F 3/34* | (2006.01) |
| *B09C 1/10* | (2006.01) |
| *C02F 101/22* | (2006.01) |
| *C02F 101/30* | (2006.01) |
| *C02F 101/20* | (2006.01) |

(52) U.S. Cl.
CPC ............... *C12N 1/20* (2013.01); *B09C 1/10* (2013.01); *C02F 3/342* (2013.01); *C12P 3/00* (2013.01); *C12P 7/10* (2013.01); *C12R 1/085* (2013.01); *C02F 2101/20* (2013.01); *C02F 2101/22* (2013.01); *C02F 2101/306* (2013.01)

(58) Field of Classification Search
CPC ... C07K 14/32; C07K 2319/035; C12N 11/16
USPC .................. 435/170, 252.31, 262.5
See application file for complete search history.

(56) References Cited

U.S. PATENT DOCUMENTS

| | | | |
|---|---|---|---|
| 8,030,064 | B2 | 10/2011 | Lee et al. |
| 2004/0077090 | A1 | 4/2004 | Short |
| 2010/0291100 | A1 | 11/2010 | Macinga |

FOREIGN PATENT DOCUMENTS

| | | |
|---|---|---|
| EP | 0 792 363 B1 | 12/2003 |
| WO | 02/00232 A2 | 1/2002 |
| WO | 2005/028654 A1 | 3/2005 |
| WO | 2006/012366 A2 | 2/2006 |
| WO | 2007078127 A1 | 7/2007 |
| WO | 2007/086898 A2 | 8/2007 |

OTHER PUBLICATIONS

Ciabattini, A., et al., "Oral Priming of Mice by Recombinant Spores of Bacillus subtilis," Vaccine, Oct. 2004, pp. 4139-4143, vol. 22, Nos. 31-32.
Duc, L. H., et al., "Immunization Against Anthrax Using Bacillus subtilis Spores expressing the Anthrax Protective Antigen," Vaccine, Jan. 2007, pp. 346-355, vol. 25, No. 2.
Duc, L. H., et al., "Bacterial Spores as Vaccine Vehicles," Infection and Immunity, May 2003, pp. 2810-2818, vol. 71, No. 5.
Hoelscher, B., et al., "Removal of Toxic Contaminants from Polluted Soil and Water Via Enzyme-Linked Bacillus Spores," Poster presented at Missouri Life Sciences Week Research Poster Session, Apr. 14, 2010, 1 page.
Isticato, R., et al., "Surface Display of Recombinant Proteins in Bacillus subtilis Spores," Journal of Bacteriology, Nov. 2001, pp. 6294-6301, vol. 183, No. 21.
Johnson, M. J., et al., "ExsY and CotY Are Required for the Correct Assembly of the Exosporium and Spore Coat of Bacillus cereus," Journal of Bacteriology, Nov. 2006, pp. 7905-7913, vol. 188, No. 22.
Kim, J. H., et al., "Spore-Displayed Streptavidin: A Live Diagnostic Tool in Biotechnology," Biochemical and Biophysical Research Communications, May 2005, pp. 210-214, vol. 331, No. 1.
Kim, J. H., et al., "Bacterial Surface Display of GFP(uv) on Bacillus subtilis Spores," Journal of Microbiology and Biotechnology, Apr. 2007, pp. 677-680, vol. 17, No. 4.
Leski, T. A., et al., "Identification and Classification of bcl Genes and Proteins of Bacillus cereus Group Organisms and Their Application in Bacillus anthracis Detection and Fingerprinting," Applied and Environmental Microbiology, Nov. 2009, pp. 7163-7172, vol. 75, No. 22.
Li, W. et al., "Cloning of the Thermostable Cellulase Gene from Newly Isolated Bacillus subtilis and Its Expression in *Escherichia coli*," Molecular Biotechnology, 2008, pp. 195-201, vol. 40, No. 2.
Luiz, W. B., et al., "Boosting Systemic and Secreted Antibody Responses in Mice Orally Immunized with Recombinant Bacillus subtilis Strains Following Parenteral Priming with a DNA Vaccine Encoding the Enterotoxigenic *Escherichia coli* (ETEC) CFA/I fimbriae B subunit," Vaccine, 2008, pp. 3998-4005, vol. 26, No. 32.
Mauriello, E. M., et al., "Display of Heterologous Antigens on the Bacillus subtilis Spore Coat Using CotC as a Fusion Partner," Vaccine, Mar. 2004, pp. 1177-1187, vol. 22, Nos. 9-10.
Paccez, J. D., et al., "Stable Episomal Expression System Under Control of a Stress Inducible Promoter Enhances the Immunogenicity of Bacillus subtilis as a Vector for Antigen Delivery," Vaccine, Apr. 2006, pp. 2935-2943, vol. 24, No. 15.
Paccez, J. D., et al., "Evaluation of Different Promoter Sequences and Antigen Sorting Signals on the Immunogenicity of Bacillus subtilis Vaccine Vehicles," Vaccine, Jun. 2007, pp. 4671-4680, vol. 25, No. 24.

(Continued)

*Primary Examiner* — Janet L Epps-Smith
(74) *Attorney, Agent, or Firm* — Senniger Powers LLP

(57) ABSTRACT

Herein a *Bacillus* exosporium molecule delivery (BEMD) system that provides a means to deliver molecules of interest (MOIs) to an environment is disclosed. The system results in the display of MOIs on the exosporium surface of *Bacillus* family members such that they can be delivered to an environment in a stable and active form. In addition, methods of making and using the system are described.

26 Claims, 29 Drawing Sheets
(27 of 29 Drawing Sheet(s) Filed in Color)
Specification includes a Sequence Listing.

(56) References Cited

OTHER PUBLICATIONS

Park, T. J., et al., "Spore Display Using Bacillus thuringiensis Exposporium Protein InhA," Journal of Microbiology and Biotechnology, May 2009, pp. 495-501, vol. 19, No. 5.

Park, T. J., "Surface-Display of Recombinant Proteins on Bacterial Exosporium and its Biotechnological Applications," Doctoral Thesis presented to the Department of Chemical and Biomolecular Engineering, Korea Advanced Institute of Science and Technology, 2004, 104 pages.

Sequence Listing filed in WO 2007/078127 A1 published Jul. 12, 2007, downloaded from <http://patentscope.wipo.int/search/en/detail.jsf?docId=WO2007078127&recNum=1&tab=PCTDocuments&maxRec=&office=&prevFilter=&sortOption=&queryString=>, 5 pages.

Steichen, C. T., et al., "Non-Uniform Assembly of the Bacillus anthracis Exosporium and a Bottle Cap Model for Spore Germination and Outgrowth," Molecular Microbiology, 2007, pp. 359-367, vol. 64, No. 2.

Tan, L., et al., "Sequence Motifs and Proteolytic Cleavage of the Collagen-Like Glycoprotein BclA Required for Its Attachment to the Exosporium of Bacillus anthracis," Journal of Bacteriology, Mar. 2010, pp. 1259-1268, vol. 192, No. 5.

Thompson, B. M., et al., "Targeting of the BclA and BclB Proteins to the Bacillus anthracis Spore Surface," Molecular Microbiology, Oct. 2008, pp. 421-434, vol. 70, No. 2.

Thompson, B. M., et al., "The BclB Glycoprotein of Bacillus anthracis is Involved in Exosporium Integrity," Journal of Bacteriology, Sep. 2007, pp. 6704-6713, vol. 189, No. 18.

Thompson, B. M., et al., "The Co-Dependence of BxpB/ExsFA and BclA for Proper Incorporation into the Exosporium of Bacillus anthracis," Molecular Microbiology, Feb. 2011, pp. 799-813, vol. 79, No. 3.

Waller, L. N., et al., "Identification of a Second Collagen-Like Glycoprotein Produced by Bacillus anthracis and Demonstration of Associated Spore-Specific Sugars," Journal of Bacteriology, Jul. 2005, pp. 4592-4597, vol. 187, No. 13.

Zhou, Z., et al., "Oral Administration of a Bacillus subtilis Spore-Based Vaccine Expressing Clonorchis sinensis tegumental Protein 22.3 kDa Confers Protection Against Clonorchis sinensis," Vaccine, Mar. 2008, pp. 1817-1825, vol. 26, No. 15.

Zhou, Z., et al., "Immunogenicity of Recombinant Bacillus subtilis Spores Expressing Clonorchis sinensis tegumental Protein," Parasitology Research, Jan. 2008, pp. 293-297, vol. 102, No. 2.

Thompson, B. M., "Amino-Terminal Sequences of the Bacillus Anthracis Exosporium Proteins BclA and BclB Important for Localization and Attachment to the Spore Surface," A Thesis presented to the Faculty of the Graduate School at the University of Missouri, Columbia, Aug. 2008, 165 pages.

FIG. 1

B. anthracis spore

Exosporium nap (BclA)
Exosporium basal layer
Spore coat
Cortex

FIG. 2A

MSNNNYSNGLNPDESLSASAFDPNLVGPTLPPIPPFTLPTG   SEQ.ID.NO:7
MSEKYIIHGTALEPNLIGPTLPPIPPFTFPNG   SEQ.ID.NO:8
MVKVVEGNGGKSKIKSPLNSNEFKILSDLVGPIFPPVPIGMTGIT   SEQ.ID.NO:9
MKQNDKLWLDKGIIGPENIGPTFPVLPPIHIPTG   SEQ.ID.NO:10
LI/VGPTL/FPPIPP   SEQ.ID.NO:11

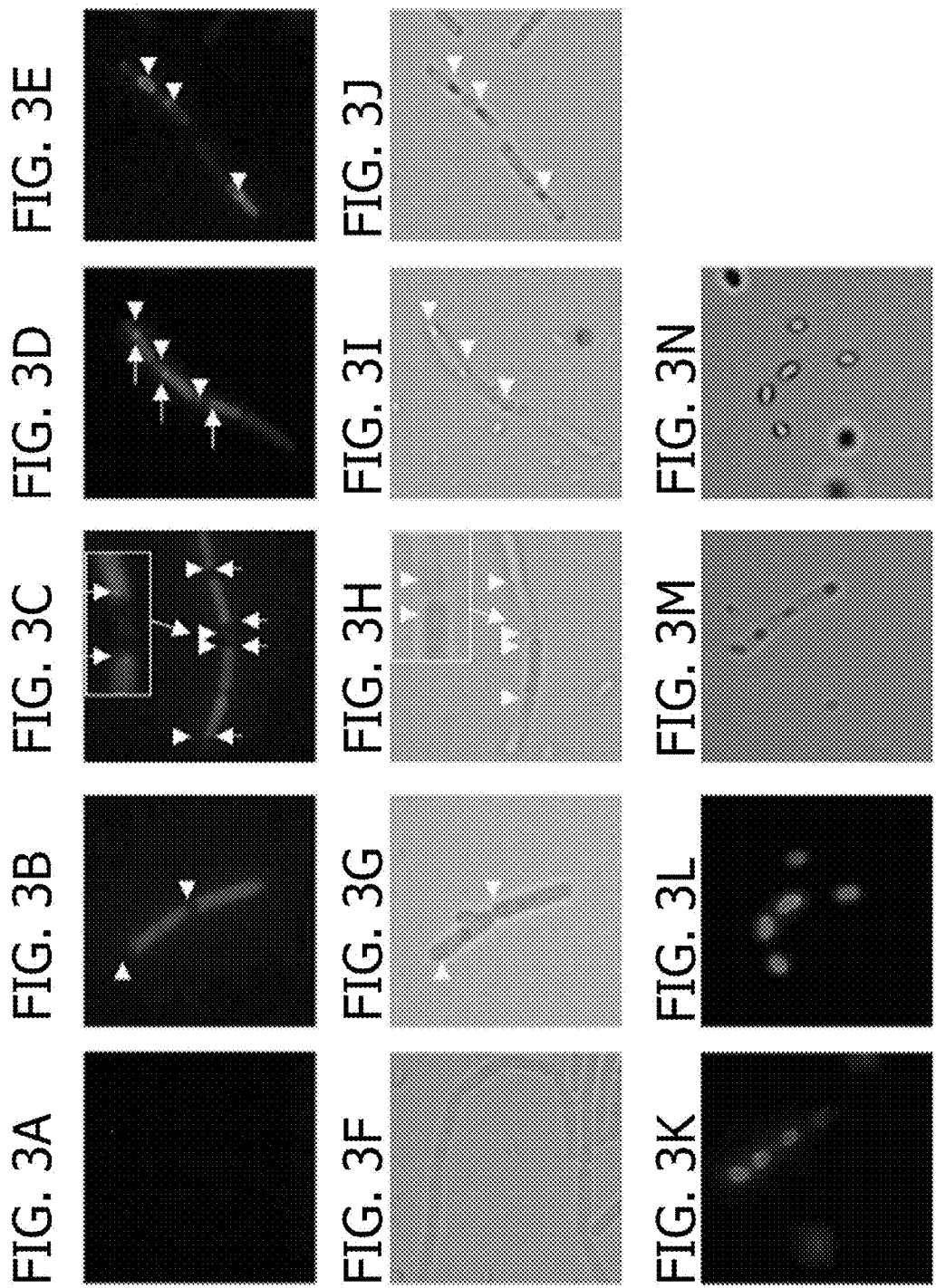

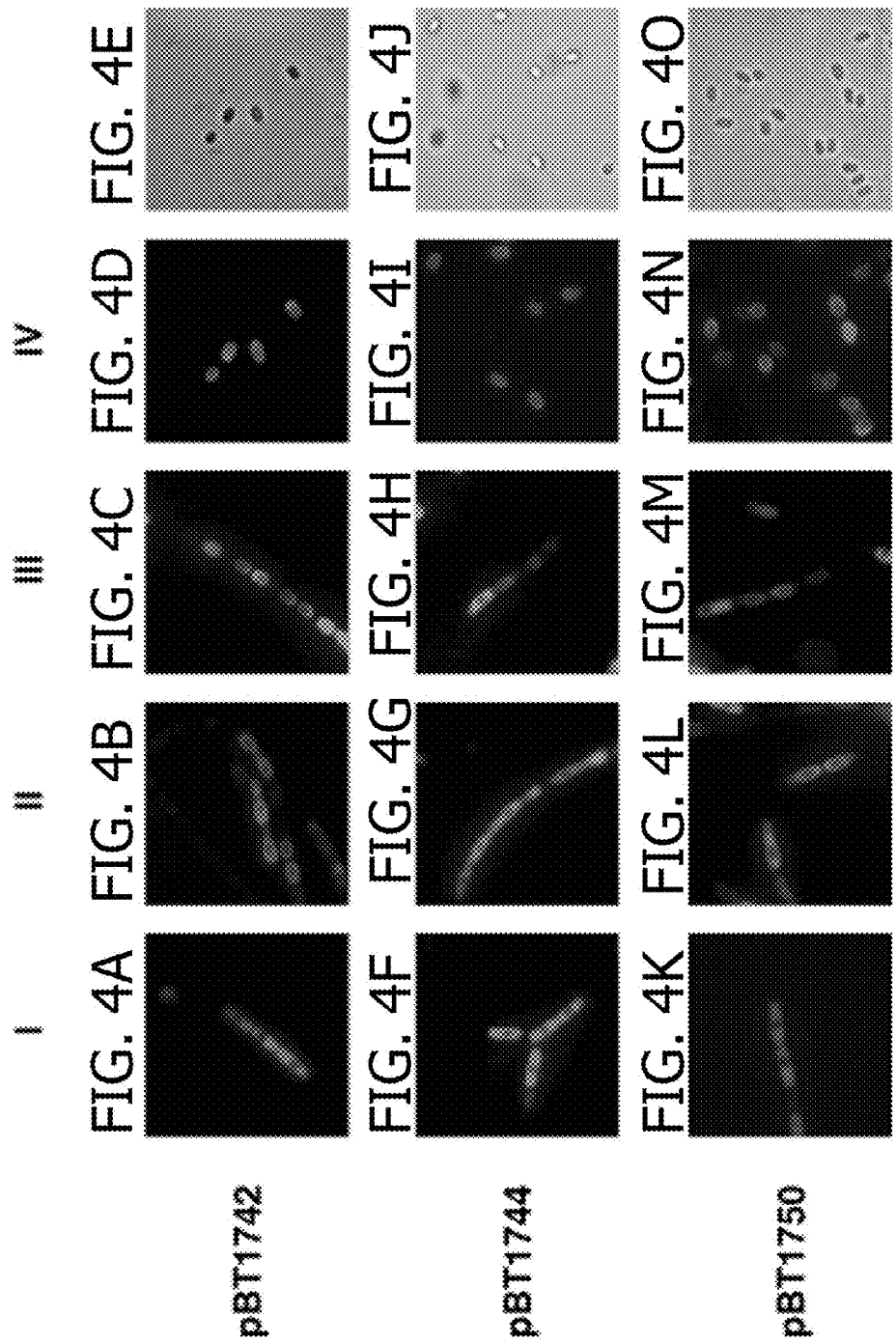

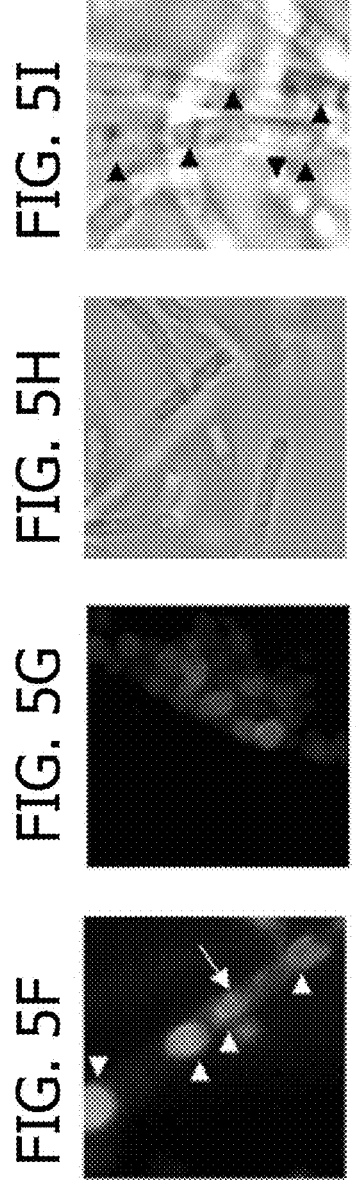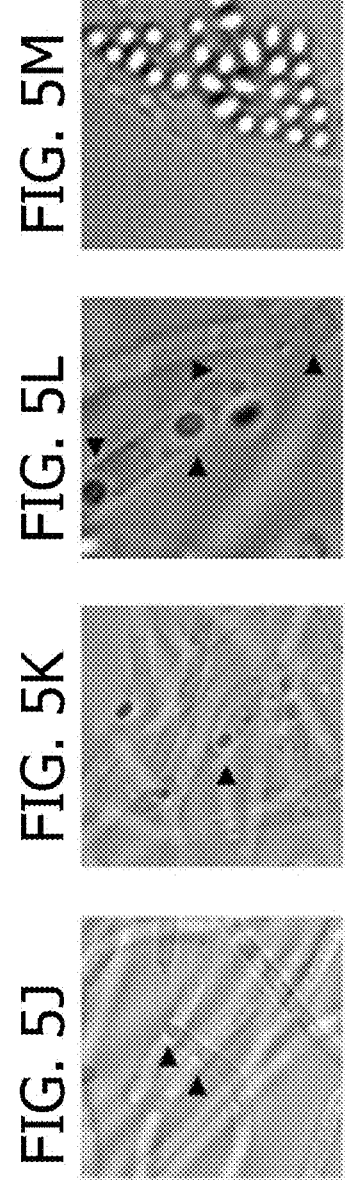

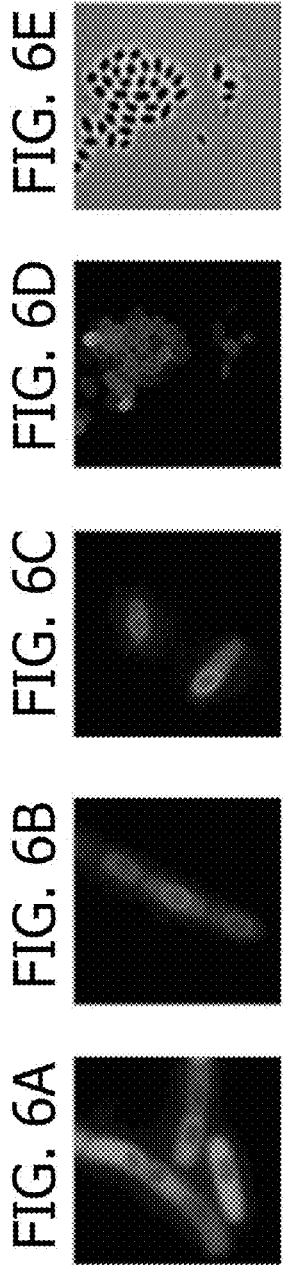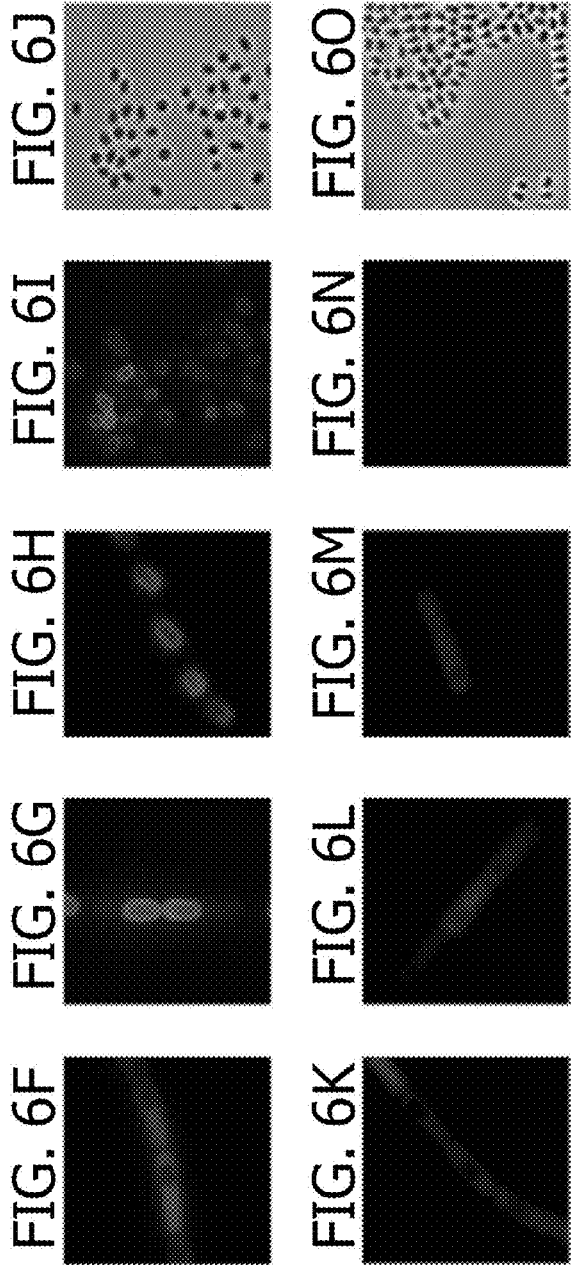

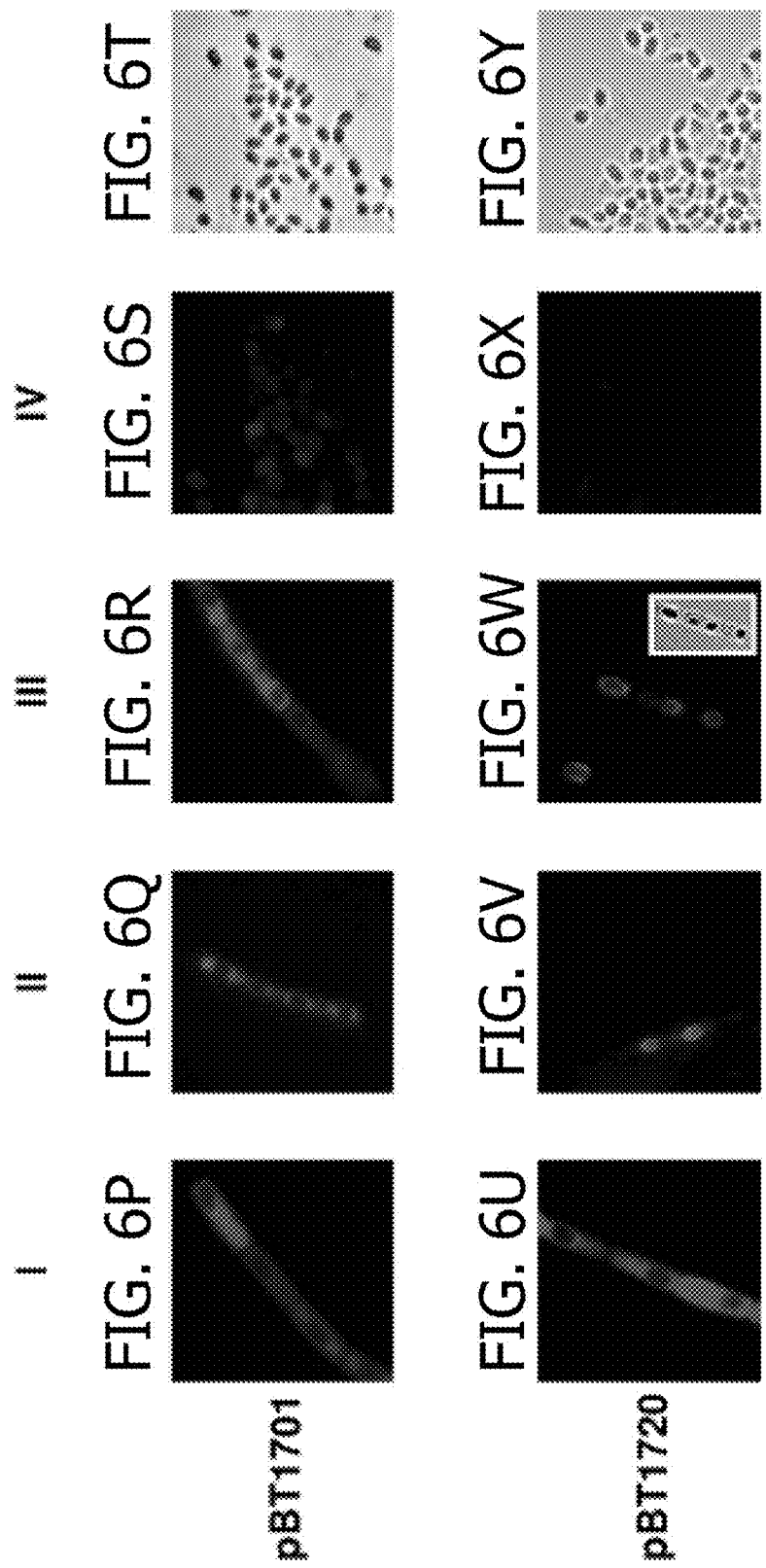

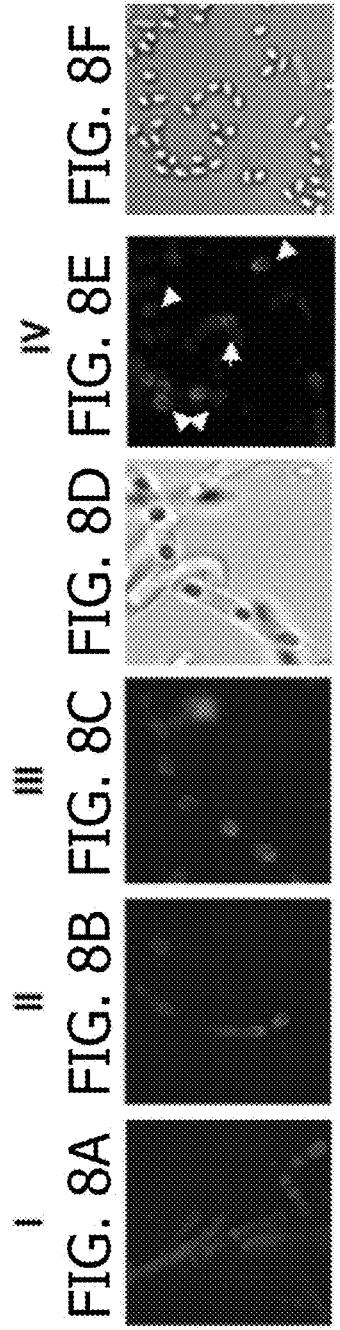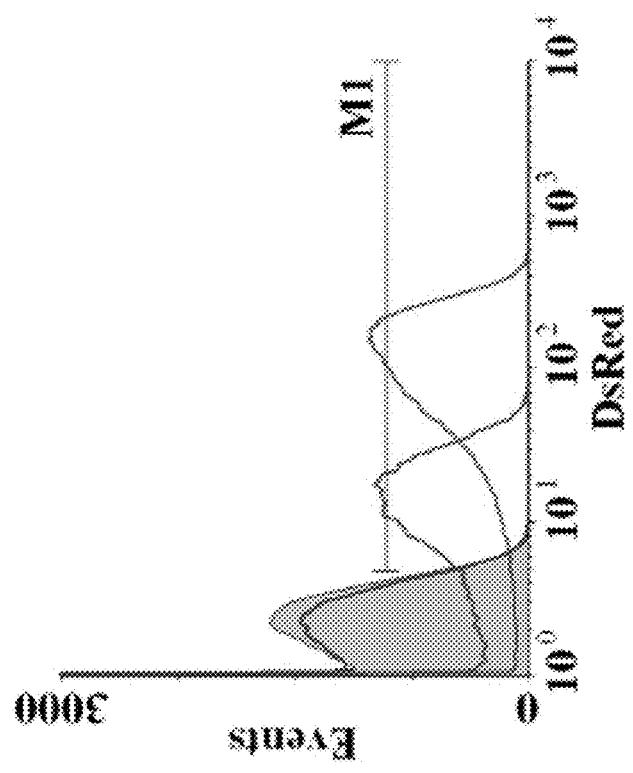

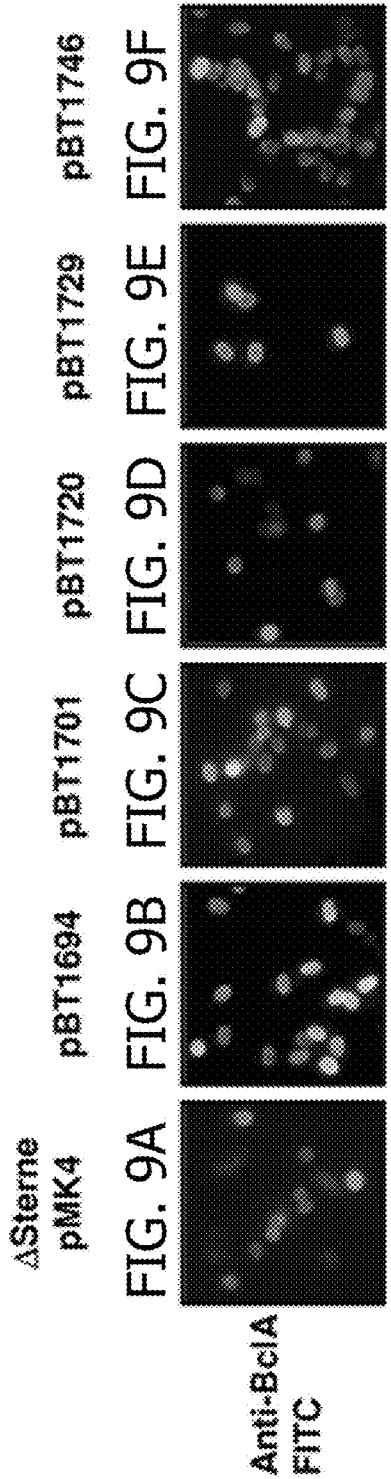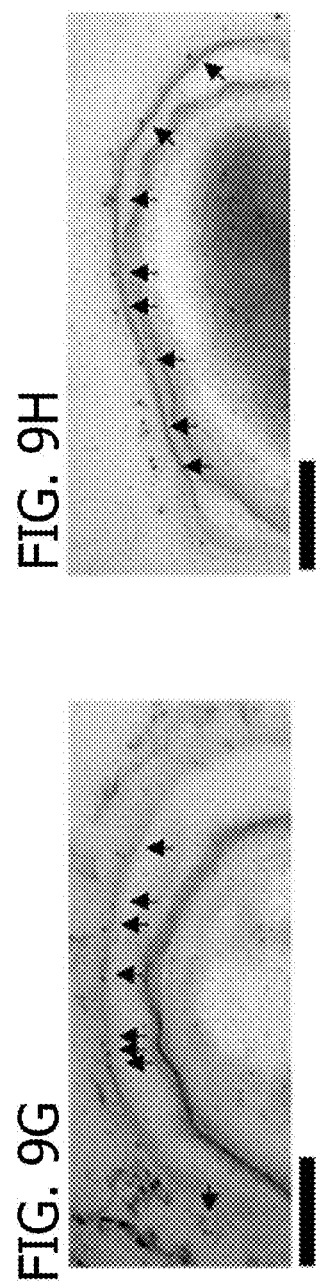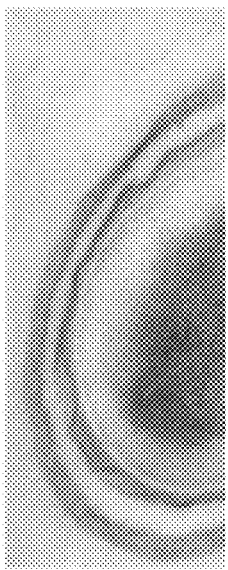

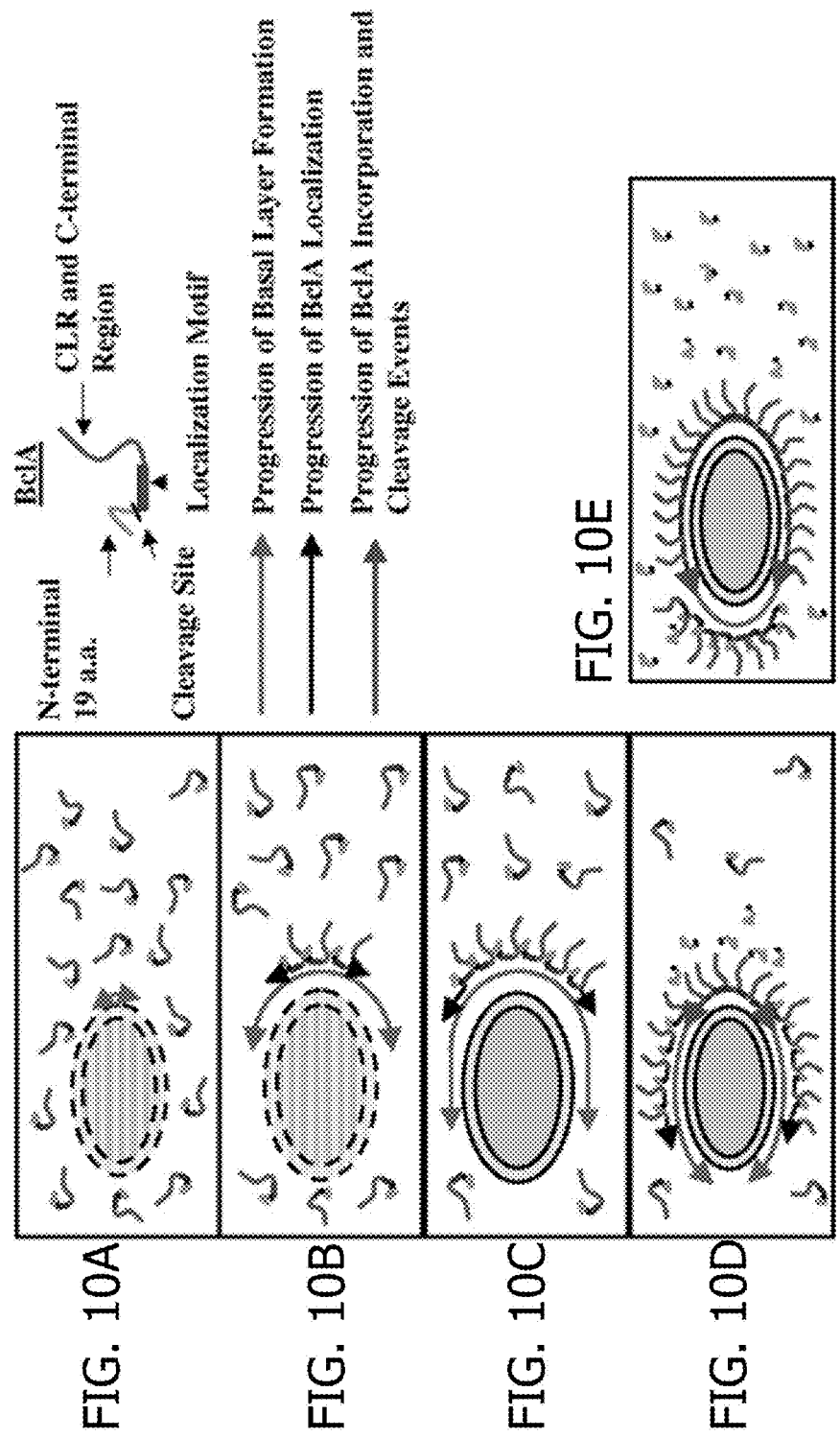

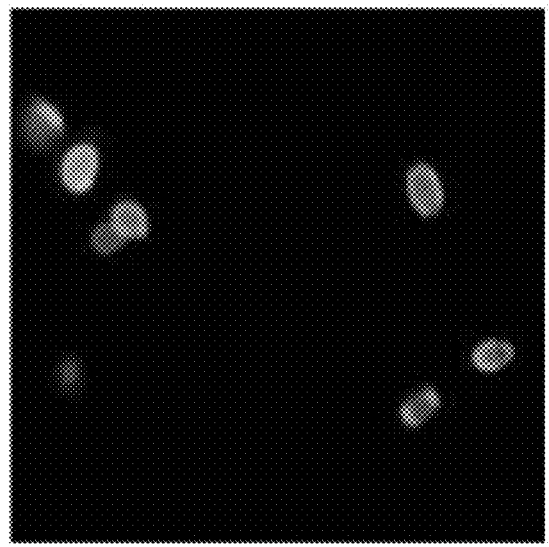
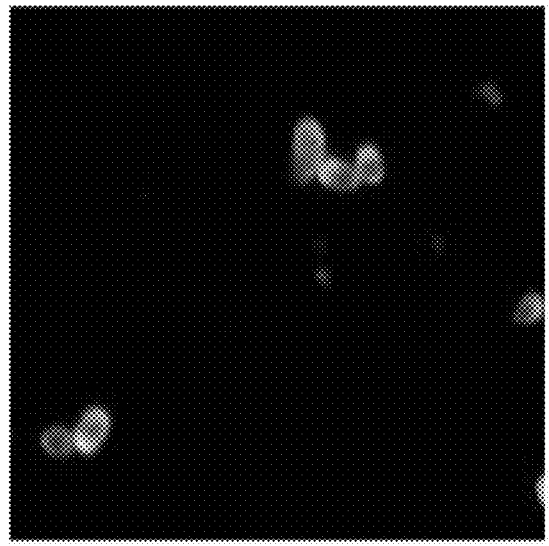

FIG. 15

SEQUENCE LISTING

```
<160> NUMBER OF SEQ ID NOS: 64

<210> SEQ ID NO 1
<211> LENGTH: 35
<212> TYPE: PRT
<213> ORGANISM: Bacillus spp

<400> SEQUENCE: 1

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro
        35

<210> SEQ ID NO 2
<211> LENGTH: 32
<212> TYPE: PRT
```

<213> ORGANISM: Bacillus spp

<400> SEQUENCE: 2

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

<210> SEQ ID NO 3
<211> LENGTH: 31
<212> TYPE: PRT
<213> ORGANISM: Bacillus spp

<400> SEQUENCE: 3

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro
            20                  25                  30

<210> SEQ ID NO 4
<211> LENGTH: 36
<212> TYPE: PRT
<213> ORGANISM: Bacillus spp

<400> SEQUENCE: 4

Met Val Lys Val Val Glu Gly Asn Gly Gly Lys Ser Lys Ile Lys Ser
1               5                   10                  15

Pro Leu Asn Phe Lys Ile Leu Ser Asp Leu Val Gly Pro Thr Phe Pro
            20                  25                  30

Pro Val Pro Thr
        35

<210> SEQ ID NO 5
<211> LENGTH: 17
<212> TYPE: PRT
<213> ORGANISM: Bacillus spp

<400> SEQUENCE: 5

Met Ala Phe Asp Pro Asn Leu Val Gly Pro Thr Leu Pro Pro Ile Pro
1               5                   10                  15

Pro

<210> SEQ ID NO 6
<211> LENGTH: 27
<212> TYPE: PRT
<213> ORGANISM: Bacillus spp

<400> SEQUENCE: 6

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro
            20                  25

<210> SEQ ID NO 7
<211> LENGTH: 41
<212> TYPE: PRT
<213> ORGANISM: Bacillus spp

<400> SEQUENCE: 7

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
            35                  40

<210> SEQ ID NO 8
<211> LENGTH: 33
<212> TYPE: PRT
<213> ORGANISM: Bacillus spp

<400> SEQUENCE: 8

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly

<210> SEQ ID NO 9
<211> LENGTH: 44
<212> TYPE: PRT
<213> ORGANISM: Bacillus spp

<400> SEQUENCE: 9

Met Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr
            35                  40

<210> SEQ ID NO 10
<211> LENGTH: 34
<212> TYPE: PRT
<213> ORGANISM: Bacillus spp

<400> SEQUENCE: 10

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly

<210> SEQ ID NO 11
<211> LENGTH: 13
<212> TYPE: PRT
<213> ORGANISM: Bacillus spp

<400> SEQUENCE: 11

Leu Ile Val Gly Pro Thr Leu Phe Pro Pro Ile Pro Pro
1               5                   10

<210> SEQ ID NO 12
<211> LENGTH: 35
<212> TYPE: PRT
<213> ORGANISM: Bacillus spp

<400> SEQUENCE: 12

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

```
Ile Pro Pro
        35

<210> SEQ ID NO 13
<211> LENGTH: 17
<212> TYPE: PRT
<213> ORGANISM: Bacillus spp

<400> SEQUENCE: 13

Met Ala Phe Asp Pro Asn Leu Val Gly Pro Thr Leu Pro Pro Ile Pro
1               5                   10                  15

Pro

<210> SEQ ID NO 14
<211> LENGTH: 35
<212> TYPE: PRT
<213> ORGANISM: Bacillus spp

<400> SEQUENCE: 14

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro
        35

<210> SEQ ID NO 15
<211> LENGTH: 35
<212> TYPE: PRT
<213> ORGANISM: Bacillus spp

<400> SEQUENCE: 15

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro
        35

<210> SEQ ID NO 16
<211> LENGTH: 24
<212> TYPE: PRT
<213> ORGANISM: Bacillus spp

<400> SEQUENCE: 16

Met Ser Asn Asn Asn Tyr Ser Asn Gly Leu Asn Pro Asp Glu Ser Leu
1               5                   10                  15

Ser Ala Ser Ala Phe Asp Pro Asn
            20

<210> SEQ ID NO 17
<211> LENGTH: 12
<212> TYPE: PRT
<213> ORGANISM: Bacillus spp

<400> SEQUENCE: 17

Met Leu Val Gly Pro Thr Leu Pro Pro Ile Pro Pro
1               5                   10

<210> SEQ ID NO 18
<211> LENGTH: 1
```

```
<212> TYPE: PRT
<213> ORGANISM: Bacillus spp

<400> SEQUENCE: 18

Met
1

<210> SEQ ID NO 19
<211> LENGTH: 28
<212> TYPE: PRT
<213> ORGANISM: Bacillus spp

<400> SEQUENCE: 19

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro
            20                  25

<210> SEQ ID NO 20
<211> LENGTH: 28
<212> TYPE: PRT
<213> ORGANISM: Bacillus spp

<400> SEQUENCE: 20

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro
            20                  25

<210> SEQ ID NO 21
<211> LENGTH: 26
<212> TYPE: DNA
<213> ORGANISM: Bacillus spp

<400> SEQUENCE: 21
ctcgagtaat caccctcttc caaatc                                          26

<210> SEQ ID NO 22
<211> LENGTH: 37
<212> TYPE: DNA
<213> ORGANISM: Bacillus spp

<400> SEQUENCE: 22
ttaccaccga taccaccaat ggtgagcaag ggcgagg                               37

<210> SEQ ID NO 23
<211> LENGTH: 26
<212> TYPE: DNA
<213> ORGANISM: Bacillus spp

<400> SEQUENCE: 23
ctcgagtaat caccctcttc caaatc                                          26

<210> SEQ ID NO 24
<211> LENGTH: 42
<212> TYPE: DNA
<213> ORGANISM: Bacillus spp

<400> SEQUENCE: 24
ccattattat tgaaaaagtt gctatggtga gcaagggcga gg                         42

<210> SEQ ID NO 25
<211> LENGTH: 26
```

<212> TYPE: DNA
<213> ORGANISM: Bacillus spp

<400> SEQUENCE: 25
ctcgagtaat caccctcttc caaatc                                    26

<210> SEQ ID NO 26
<211> LENGTH: 34
<212> TYPE: DNA
<213> ORGANISM: Bacillus spp

<400> SEQUENCE: 26
ggaggtgaat ttatggcatt tgaccctaat cttg                           34

<210> SEQ ID NO 27
<211> LENGTH: 26
<212> TYPE: DNA
<213> ORGANISM: Bacillus spp

<400> SEQUENCE: 27
ctcgagtaat caccctcttc caaatc                                    26

<210> SEQ ID NO 28
<211> LENGTH: 48
<212> TYPE: DNA
<213> ORGANISM: Bacillus spp

<400> SEQUENCE: 28
aaggctgccg cagcgatgtc aaataataat tattcaaatg accatgat            48

<210> SEQ ID NO 29
<211> LENGTH: 26
<212> TYPE: DNA
<213> ORGANISM: Bacillus spp

<400> SEQUENCE: 29
ctcgagtaat caccctcttc caaatc                                    26

<210> SEQ ID NO 30
<211> LENGTH: 41
<212> TYPE: DNA
<213> ORGANISM: Bacillus spp

<400> SEQUENCE: 30
ccaccgatac caccaatgag taaaggagaa gaacttttca c                   41

<210> SEQ ID NO 31
<211> LENGTH: 26
<212> TYPE: DNA
<213> ORGANISM: Bacillus spp

<400> SEQUENCE: 31
ctcgagtaat caccctcttc caaatc                                    26

<210> SEQ ID NO 32
<211> LENGTH: 42
<212> TYPE: DNA
<213> ORGANISM: Bacillus spp

<400> SEQUENCE: 32
ttaccaccga taccaccaat gaccatgatt acgccaagct tg                  42

<210> SEQ ID NO 33

```
<211> LENGTH: 26
<212> TYPE: DNA
<213> ORGANISM: Bacillus spp

<400> SEQUENCE: 33
ctcgagtaat caccctcttc caaatc                                          26

<210> SEQ ID NO 34
<211> LENGTH: 42
<212> TYPE: DNA
<213> ORGANISM: Bacillus spp

<400> SEQUENCE: 34
acgctttatg gaggtgaatt tatgaccatg attacgccaa gc                        42

<210> SEQ ID NO 35
<211> LENGTH: 26
<212> TYPE: DNA
<213> ORGANISM: Bacillus spp

<400> SEQUENCE: 35
ctcgagtaat caccctcttc caaatc                                          26

<210> SEQ ID NO 36
<211> LENGTH: 79
<212> TYPE: DNA
<213> ORGANISM: Bacillus spp

<400> SEQUENCE: 36
tcaaatggat taaaccccga tgaatcttta tcagctagtg catttgaccc taatatgacc     60
atgattacgc caagcttgc                                                  79

<210> SEQ ID NO 37
<211> LENGTH: 26
<212> TYPE: DNA
<213> ORGANISM: Bacillus spp

<400> SEQUENCE: 37
ctcgagtaat caccctcttc caaatc                                          26

<210> SEQ ID NO 38
<211> LENGTH: 58
<212> TYPE: DNA
<213> ORGANISM: Bacillus spp

<400> SEQUENCE: 38
atgcttgtag gacctacatt accaccgata ccaatgacca tgattacgcc aagcttgc       58

<210> SEQ ID NO 39
<211> LENGTH: 27
<212> TYPE: DNA
<213> ORGANISM: Bacillus spp

<400> SEQUENCE: 39
ctcgagatta gaacgtaacc aatttag                                         27

<210> SEQ ID NO 40
<211> LENGTH: 45
<212> TYPE: DNA
<213> ORGANISM: Bacillus spp

<400> SEQUENCE: 40
accttcccgg ttcttccccc aatgaccatg attacgccaa gcttg                     45
```

<210> SEQ ID NO 41
<211> LENGTH: 26
<212> TYPE: DNA
<213> ORGANISM: Bacillus spp

<400> SEQUENCE: 41
ctcgagtaat caccctcttc caaatc                                    26

<210> SEQ ID NO 42
<211> LENGTH: 45
<212> TYPE: DNA
<213> ORGANISM: Bacillus spp

<400> SEQUENCE: 42
acgctttatg gaggtgaatt tatgaaacag aatgacaaat tatgg               45

<210> SEQ ID NO 43
<211> LENGTH: 37
<212> TYPE: DNA
<213> ORGANISM: Bacillus spp

<400> SEQUENCE: 43
cctcgccctt gctcaccatt ggtggtatcg gtggtaa                        37

<210> SEQ ID NO 44
<211> LENGTH: 31
<212> TYPE: DNA
<213> ORGANISM: Bacillus spp

<400> SEQUENCE: 44
gcctcgagtt acttgtacag ctcgtccatg c                              31

<210> SEQ ID NO 45
<211> LENGTH: 42
<212> TYPE: DNA
<213> ORGANISM: Bacillus spp

<400> SEQUENCE: 45
cctcgccctt gctcaccata gcaactttt caataataat gg                   42

<210> SEQ ID NO 46
<211> LENGTH: 31
<212> TYPE: DNA
<213> ORGANISM: Bacillus spp

<400> SEQUENCE: 46
gcctcgagtt acttgtacag ctcgtccatg c                              31

<210> SEQ ID NO 47
<211> LENGTH: 34
<212> TYPE: DNA
<213> ORGANISM: Bacillus spp

<400> SEQUENCE: 47
gattagggtc aaatgccata aattcacctc cata                           34

<210> SEQ ID NO 48
<211> LENGTH: 31
<212> TYPE: DNA
<213> ORGANISM: Bacillus spp

<400> SEQUENCE: 48

```
gcctcgagtt acttgtacag ctcgtccatg c                                      31

<210> SEQ ID NO 49
<211> LENGTH: 36
<212> TYPE: DNA
<213> ORGANISM: Bacillus spp

<400> SEQUENCE: 49
catcgctgcg gcagccttgt acagctcgtc catgcc                                 36

<210> SEQ ID NO 50
<211> LENGTH: 30
<212> TYPE: DNA
<213> ORGANISM: Bacillus spp

<400> SEQUENCE: 50
ctcgagttat ttgtagagct catccatgcc                                        30

<210> SEQ ID NO 51
<211> LENGTH: 42
<212> TYPE: DNA
<213> ORGANISM: Bacillus spp

<400> SEQUENCE: 51
ttctccttta ctcattggtg gtatcggtgg taatgtaggt cc                          42

<210> SEQ ID NO 52
<211> LENGTH: 30
<212> TYPE: DNA
<213> ORGANISM: Bacillus spp

<400> SEQUENCE: 52
ctcgagttat ttgtagagct catccatgcc                                        30

<210> SEQ ID NO 53
<211> LENGTH: 42
<212> TYPE: DNA
<213> ORGANISM: Bacillus spp

<400> SEQUENCE: 53
tggcgtaatc atggtcattg gtggtatcgg tggtaatgta gg                          42

<210> SEQ ID NO 54
<211> LENGTH: 33
<212> TYPE: DNA
<213> ORGANISM: Bacillus spp

<400> SEQUENCE: 54
ctcgagtaaa ggaacagatg gtggcgtccc tcg                                    33

<210> SEQ ID NO 55
<211> LENGTH: 47
<212> TYPE: DNA
<213> ORGANISM: Bacillus spp

<400> SEQUENCE: 55
caagcttggc gtaatcatgg tcataaattc acctccataa agcgttc                     47

<210> SEQ ID NO 56
<211> LENGTH: 33
<212> TYPE: DNA
<213> ORGANISM: Bacillus spp

<400> SEQUENCE: 56
```

```
ctcgagtaaa ggaacagatg gtggcgtccc tcg                              33
```

<210> SEQ ID NO 57
<211> LENGTH: 73
<212> TYPE: DNA
<213> ORGANISM: Bacillus spp

<400> SEQUENCE: 57

```
gctgataaag attcatcggg gtttaatcca tttgaataat tattatttga cataaattca   60
cctccataaa gcg                                                     73
```

<210> SEQ ID NO 58
<211> LENGTH: 33
<212> TYPE: DNA
<213> ORGANISM: Bacillus spp

<400> SEQUENCE: 58

```
ctcgagtaaa ggaacagatg gtggcgtccc tcg                              33
```

<210> SEQ ID NO 59
<211> LENGTH: 53
<212> TYPE: DNA
<213> ORGANISM: Bacillus spp

<400> SEQUENCE: 59

```
tggtatcggt ggtaatgtag gtcctacaag cataaattca cctccataaa gcg         53
```

<210> SEQ ID NO 60
<211> LENGTH: 33
<212> TYPE: DNA
<213> ORGANISM: Bacillus spp

<400> SEQUENCE: 60

```
ctcgagtaaa ggaacagatg gtggcgtccc tcg                              33
```

<210> SEQ ID NO 61
<211> LENGTH: 38
<212> TYPE: DNA
<213> ORGANISM: Bacillus spp

<400> SEQUENCE: 61

```
tggcgtaatc atggtcattg ggggaagaac cgggaagg                         38
```

<210> SEQ ID NO 62
<211> LENGTH: 33
<212> TYPE: DNA
<213> ORGANISM: Bacillus spp

<400> SEQUENCE: 62

```
ctcgagtaaa ggaacagatg gtggcgtccc tcg                              33
```

<210> SEQ ID NO 63
<211> LENGTH: 44
<212> TYPE: DNA
<213> ORGANISM: Bacillus spp

<400> SEQUENCE: 63

```
cataatttgt cattctgttt cataaattca cctccataaa gcgt                  44
```

<210> SEQ ID NO 64
<211> LENGTH: 33
<212> TYPE: DNA

```
<213> ORGANISM: Bacillus spp

<400> SEQUENCE: 64
ctcgagtaaa ggaacagatg gtggcgtccc tcg                                    33
```

BACILLUS BASED DELIVERY SYSTEM AND METHODS OF USE

RELATED APPLICATIONS

This application is a divisional of U.S. Non-Provisional patent application Ser. No. 13/089,015, filed Apr. 18, 2011, which is incorporated herein by reference in its entirety.

FIELD OF THE INVENTION

The present invention relates to a system suitable for the production and delivery of bioparticles, proteins, and small molecules. The invention provides both compositions and methods of use relating to the system. The system utilizes sequences from *Bacillus* spp. glycoproteins to insert molecules of interest (MOI) into the exosporium of a *Bacillus* spore and carry the MOIs to a target site as part of a delivery system. The delivery system is useful in bioremediation of contaminants, the production of biofuels, in vaccine therapeutics, in biosensor technology, in biocatalyst technology, as biofilters, in fuel cells, and in other fields of use.

BACKGROUND OF THE INVENTION

*Bacillus* is a genus of rod-shaped bacteria. Ubiquitous in nature, *Bacillus* includes both free-living and pathogenic species. There are three important pathogenic members of *Bacillus*: *B. cereus* causes a foodborne illness similar to that of *Staphylococcus*; *B. thuringiensis* is an important insect pathogen, and is sometimes used to control insect pests; and *B. anthracis* causes anthrax in humans and animals. Under stressful environmental conditions, these cells shift to an alternative developmental pathway, sporulation, and produce oval endospores that can stay dormant for extended periods.

Much of what is known of the sporulation process comes from genetic studies of the nonpathogenic *Bacillus subtilis*. Unlike the pathogenic *Bacillus* spp. above, *B. subtilis* does not have an exosporium layer on its exterior. This outermost layer of the endospore consists of a basal layer surrounded by an external nap of hair-like projections (see FIG. 1). Filaments of the hair-like nap are predominantly formed by the collagen-like glycoprotein BclA, while the basal layer is comprised of a number of different proteins.

The use of bacteria spores as delivery systems has been demonstrated using a *B. subtilis* platform. See, Kim and Schumann, 2009. The *B. subtilis* platform was proposed as a vaccine delivery system using CotB and CotC fusion proteins. This platform displays a low level of C-terminally fused proteins on the spore coat of the endospores. Both CotB and CotC have complex structures with multiple cysteine bonds with other spore coat proteins and a rigid structure. The necessity to form multiple binding partners for Cot B/C incorporation hinders high protein expression levels on the surface of the spores. Additionally, the majority of the CotB and CotC proteins are in a complex 3D coat structure, with only a small percentage accessible for enzymatic reactions on the surface of *B. subtilis* spores. Therefore, a need remains for a delivery system capable of displaying a high percentage of MOIs on the exosporium for delivery and that allows substantial bioactivity of the MOIs.

The delivery system of the present invention solves the above-described problems. Specifically, the present invention provides a delivery system utilizing a small expression sequence that targets the MOIs to the most external portion of the exosporium surface allowing even the most complex MOI structures to freely fold in a native fashion for optimal bioactivity. Further, the present invention provides a delivery system with high expression of MOIs. The compositions, methods of making, and methods of using the delivery system of the present invention are described in detail below.

SUMMARY OF THE INVENTION

The invention provides a *Bacillus* exosporium molecule delivery (BEMD) system suitable for delivering molecules of interest (MOIs) to an environment or area that would benefit from the presence or activity of the bioactive protein. The system includes a recombinant *Bacillus* family member expressing at least one MOI on the exterior of its exosporium. In particular, the MOI is fused to a positioning sequence that is about the first 50 amino acid residues of the N-terminal domain (NTD) of a *Bacillus* exosporium protein. The positioning sequence encodes positioning amino acid residues that insert into the exosporium such that the MOI is physically oriented at the external most portion of the exosporium.

MOIs used in the BEMD system may be any molecule of interest. Preferably, the MOI is capable of being expressed from a DNA sequence that is translated into a protein. Suitable MOIs include proteins such as enzymes, immunogenic molecules, and other peptide or polypeptide encoding sequences. The MOIs do not have to encode functional proteins. In one embodiment, the MOI is immunogenic and capable of stimulating an immune response when presented to a subject. In another embodiment, the MOIO is an enzymatic protein capable of enzymatic activity when it is presented to an environment or subject. In yet another embodiment the MOI is a substrate required by an enzymatic protein for enzymatic activity. The BEMD system may use on or more MOIs.

A BEMD system of the invention may include a recombinant *Bacillus* family member that has multiple MOIs on its exosporium. Alternatively, a BEMD system may include multiple recombinant *Bacillus* family members, each of which includes a single type of MOI on its respective exosporium. A combination of such multiple *Bacillus* family members may be used in a BEMD system to achieve a multi-molecular effect in an environment to which the BEMD system is delivered.

Recombinant *Bacillus* family members include strains of *B. anthracis*, *B. cereus*, *B. thuringiensis*, and combinations thereof. Strains of *B. thuringiensis* are preferred members. Inactivated strains are also preferred. Alternatively, nontoxic or genetically manipulated *Bacillus* family members may be used. Preferably, recombinant *Bacillus* family member cultures are prepared separately then combined together after harvest. Alternatively, *Bacillus* family members may be prepared in combination with one another from the beginning.

Positioning sequences preferably encode at least the first 50 amino acid residues of the N-terminal domain (NTD) of a *Bacillus* exosporium protein. *Bacillus* exosporium proteins include *Bacillus* BclA, BclB, and BAS3290 (BclE). Preferred *Bacillus* exosporium proteins include *Bacillus* BclA, BclB, BAS3290 (BclE), and combinations thereof.

The invention also provides methods of making a BEMD system comprising constructing a fusion construct containing at least one positioning sequence and at least one MOI; cloning the fusion construct into a shuttle plasmid; and transformation of the shuttle plasmid containing the fusion construct into a *Bacillus* family member such that the fusion construct is expressed on the family member's exosporium.

The invention further provides kits for a BEMD system containing at least one *Bacillus* family member expressing at least one positioning sequence and at least one MOI, wherein the positioning sequence is inserted into the exosporium such that the MOI is physically oriented at the external most portion of the exosporium. Alternatively, the kit contains a shuttle plasmid having a multiple cloning site whereby at least one MOI may be inserted such that it creates a fusion construct with at least one positioning sequence. The provided shuttle plasmid may contain one or more multiple cloning sites and one or more positioning sequence elements such that one or more MOIs may be inserted to create one or more fusion constructs. The kit may also provide at least one *Bacillus* family member to be transformed with the provided shuttle plasmid following insertion of the desired MOI. Preferred kits include a shuttle plasmid containing at least one positioning sequence having about the first 50 amino acid residues of the N-terminal domain (NTD) of a *Bacillus* exosporium protein.

Methods of using a BEMD system are also provided. Such methods include distributing to an environment or area at least one recombinant *Bacillus* family member expressing a fusion construct, wherein the fusion construct comprises at least one MOI and at least one positioning sequence element and the positioning sequence element encodes about the first 50 amino acid residues of the N-terminal domain (NTD) of a *Bacillus* exosporium protein, in the recombinant *Bacillus* family member's exosporium such that the MOI is physically oriented at the outer most portion of the exosporium.

One skilled in the art will recognize that the BEMD platform has a plethora of uses, which are too numerous to enumerate herein. Further, the BEMD platform may have uses beyond the current knowledge and state of technology that will come to light in the future. It is contemplated that the basic use of the present invention can easily be modified for utility in the above-described situations as well as those that will evolve with time. One advantage of the BEMD system is that the MOI is selected based on the desired use of the BEMD system. Molecules that are not currently appreciated may be easily used as MOIs with the BEMD system once they are recognized. Exemplary uses of the invention, without limitation, include delivery of immunogenic MOIs to a subject to stimulate an immune response, delivery of enzymatic MOIs to an environment to bioremediate contaminants, and the application of enzymatic MOIs to a biomass to create substances used in the food industry, biofuel/biodiesel industry, and green energy industry.

DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, the acronym "BEMD" is used in place of "BEAD" which was used in the priority applications. Therefore, any use of BEAD herein is synonymous with the use of BEMD.

An "immunogenic molecule" means a recombinant protein, native protein, or artificial small molecule that stimulates an immune response in a subject. Preferably, an immunogenic molecule does not adversely affect a subject when administered.

Herein, a "subject" may be a human or animal. "Animal" refers to a fish, bird, or mammal. Preferably the animal is a mammal such as a cat, dog, ungulate (e.g. horse, zebra, donkey, cattle/bison, rhinoceros, camel, hippopotamus, goat, swine, sheep, giraffe, okapi, moose, deer, tapir, antelope, or gazelle), rodent (e.g. mice, rats, and other small, gnawing mammals), bat, bear, primate, or cetacean.

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the subject will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of a pathogen, and/or a delay in the of onset of symptoms.

Those of skill in the art will understand that the compositions disclosed herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the compositions of the present invention can include diluents, isotonic agents, stabilizers, or adjuvants.

"Diluents", as used herein, can include water, saline, dextrose, ethanol, glycerol, and the like. "Isotonic agents" can include sodium chloride, dextrose, mannitol, sorbitol, and lactose, among others. "Stabilizers" include albumin and alkali salts of ethylendiamintetracetic acid, among others.

Herein, an "adjuvant" or "adjuvants" can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, water-in-oil emulsion, oil-in-water emulsion, and water-in-oil-in-water emulsion. The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di (caprylate/caprate), glyceryl tri-(caprylate/caprate) or propylene glycol dioleate; or esters of branched fatty acids or alcohols, in particular isostearic acid esters. The oil is used in combination with emulsifiers to form the emulsion. The emulsifiers are preferably nonionic surfactants, in particular esters of sorbitan, mannide (e.g. anhydromannitol oleate), glycol, polyglycerol, propylene glycol, and oleic, isostearic, ricinoleic or hydroxystearic acid, which are optionally ethoxylated, and polyoxypropylene-polyoxyethylene copolymer blocks, in particular the Pluronic products, especially L121. (See Hunter et al., The Theory and Practical Application of Adjuvants (Ed.Stewart-Tull, D. E. S.), John Wiley and Sons, NY, pp 51-94 (1995) and Todd et al., Vaccine 15:564-570 (1997).

Compositions of the invention also can include one or more pharmaceutical-acceptable carriers. Herein, "pharmaceutical-acceptable carrier" or "veterinary-acceptable carrier" include any and all solvents, dispersion media, coatings, stabilizing agents, growth media, dispersion media, cell culture media and cell culture constituents, coatings, adjuvants, diluents, preservatives, antibacterial and antifungal agents, isotonic agents, adsorption delaying agents, and the like.

"Administering" or the "administration of" a composition of the invention means delivery of a composition of the invention to a subject by any accepted means in the art. Such appropriate means of administration include intravenous, intra-arterial, intraperitoneal, intramuscular, subcutaneous, intrapleural, topical, or by inhalation. The appropriate means of administering a composition of the invention to a subject will be dependent upon the specific objective to be achieved (e.g. therapeutic, diagnostic, preventative) and the targeted cells, tissues, or organs.

Herein, "effective dose" means, but is not limited to, an amount of a composition of the invention that elicits, or is able to elicit, an immune response that yields a reduction of clinical symptoms in a subject to which the antigen is administered.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Biomass" is used herein to include biological material that can be converted into a biofuel, chemical or other product. One exemplary source of biomass is plant matter. Plant matter can be, for example, woody plant matter, non-woody plant matter, cellulosic material, lignocellulosic material, hemicellulosic material, carbohydrates, pectin, starch, inulin, fructans, glucans, corn, sugar cane, grasses, switchgrass, bamboo, and material derived from these. Plant matter can be further described by reference to the chemical species present, such as proteins, polysaccharides and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corn steep solids, distillers' grains, peels, pits, fermentation waste, straw, lumber, sewage, garbage and food leftovers. These materials can come from farms, forestry, industrial sources, households, etc. Another non-limiting example of biomass is animal matter, including, for example milk, meat, fat, animal processing waste, and animal waste. "Feedstock" is frequently used to refer to biomass being used for a process, such as those described herein.

"Biofuels", "Fuels and or other chemicals" and "other products" are used interchangeably and is used herein to include compounds suitable as liquid fuels, gaseous fuels, reagents, chemical feedstocks, chemical additives, processing aids, food additives, and other uses that chemicals can be put to, and includes, but is not limited to, hydrocarbons, hydrogen, methane, hydroxy compounds such as alcohols (e.g. ethanol, butanol, propanol, methanol, etc.), carbonyl compounds such as aldehydes and ketones (e.g. acetone, formaldehyde, 1-propanal, etc.), organic acids, derivatives of organic acids such as esters (e.g. wax esters, glycerides, etc.) and other functional compounds including, but not limited to, 1,2-propanediol, 1,3-propanediol, lactic acid, formic acid, acetic acid, succinic acid, pyruvic acid, enzymes such as cellulases, polysaccharases, lipases, proteases, ligninases, and hemicellulases and may be present as a pure compound, a mixture, or an impure or diluted form.

The term "fuel cell" (or traditionally termed chemical fuel cell) refers, to a device for performing an electrochemical energy conversion by use of abiotic and/or inorganic catalysts. A fuel cell works by catalysis, separating the component electrons and protons of the reactant fuel and forcing the electrons to travel trough a circuit, hence converting them to electrical power. In a fuel cell the catalysis is performed by abiotic and/or inorganic catalysts such as platinum group metal or alloys which act inhibiting on microbial activity. Accordingly, a fuel cell differs from a microbial fuel cell e.g. by the choice of catalyst. As will be apparent to the skilled person such difference will inevitably influence the fuel cell construction thus leading to a completely different construction when compared to the construction of a microbial fuel cell. Moreover, the types of fuels (substrates) which can be used in a microbial fuel cell and a fuel cell may differ significantly. In a microbial fuel cell most inorganic substrates can be used as the source of chemical energy, while a fuel cell has a very limited choice of substrates (e.g. $H_2$, $CH_4$, or methanol).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The application contains at least one drawing executed in color. Copies of this patent application publication with color drawing(s) will be provided by the Office upon request and payment of the necessary fee.

FIG. 1 shows a transmission electron micrograph of a spore of the Sterne strain of *B. anthracis*. The sample was stained with ruthenium red to better visualize the nap on the exosporium layer. The cortex, spore coat, exosporium nap (BclA), and exosporium basal layer of the spore are indicated.

FIG. 2A is an N-terminal sequence alignment of four *B. anthracis* collagen-like proteins. Each protein sequence is displayed beginning with the N-terminal methionine residue. The conserved region is underlined in each sequence. A consensus sequence (SEQ ID NO: 11) is presented below the alignment. GenBank designations of the Sterne strain are as follows: SEQ ID NO: 7 is BclA; SEQ ID NO: 8 is BAS3290 (BclE); SEQ ID NO: 9 is BAS4623; and SEQ ID NO: 10 is BclB.

FIGS. 3A-3O provide micrographs (epi-fluorescence microscopy at 600× magnification) of sporulating cells expressing the pBT1744 BclA N-terminal domain fusion and tracks expression over time. Arrowheads correspond to spores at various stages of development; arrows indicate BclA fusion localization to the spore poles. FIGS. 3F-3J, 3M, and 3N are bright field images of the epi-fluorescence images FIGS. 3A-3E, 3K and 3L, respectively. Insets in FIGS. 3C and 3H are enlarged images of the filament to enable visualization of the initial polar fusion protein localization and the site of spore development respectively. FIGS. 3A-3N specifically show the following stages. FIGS. 3A and 3F: $T_{-1.5}$, cells taken at mid-exponential phase. FIGS. 3B and 3G: $T_2$, appearance of fluorescence in the mother cell cytoplasm and the appearance of the darkened area representative of spore development (enlarged 150% for better visualization). FIGS. 3C and 3H: $T_3$, beginning of localization of BclA to the site of initiation of exosporium assembly, as noted by the small enhancement of the fluorescence at the internal pole of the developing spores. FIGS. 3D and 3I: $T_4$, progression of BclA localization of BclA around the pole of the spore at a time corresponding with the appearance of visible spores by bright field microscopy. FIGS. 3E and 3J: $T_6$, localization of BclA around the spore progressing towards completion. FIGS. 3K and 3M: $T_7$, progression of BclA localization near completion. FIGS. 3L and 3N: $T_{10}$, free fluorescent spores with the pBT1744-encoded fusions attached to the exosporium. FIG. 3O graphs the progression of the sporulating culture over time as monitored by absorbance at 600 nm. Initiation of stationary phase equals $T_0$. Cells were induced to sporulate synchronously in modified G broth. Samples were taken at the indicated times.

FIGS. 9G-9I are TEM micrographs of spores containing the BclA NTD fusion to eGFP (pBT1744). FIG. 9G shows pBT1744 fusion spores labeled with rabbit polyclonal anti-GFP antibodies followed by anti-rabbit secondary labeled with 10 nm colloidal gold particles. FIG. 9H shows pBT1744 fusion spores labeled with rabbit anti-rBclA polyclonal antibodies followed by secondary anti-rabbit antibodies labeled with 20 nm colloidal gold particles. FIG. 9I shows ΔSterne control spores labeled with pre-immune rabbit polyclonal antibodies and 20 nm colloidal gold particles. Examples of gold particles are denoted by arrows. The bar represents a 250 nm size and applies to FIGS. 9G-9I.

FIGS. 10A-10E show a model for BclA incorporation into the exosporium basal layer during sporulation in *B. anthracis*. FIG. 10A shows production of BclA and appearance of fluorescence in the mother cell cytoplasm. FIG. 10B represents the localization of BclA to the pole of the spore (facing the mother cell compartment) following the progression (light purple or gray double headed arrow) of the basal layer (dashed lines) around the spore. FIG. 10C shows the appearance of a visible spore (solid lines), and continuation of BclA localization (black arrows) around the spore. FIG. 10D illustrates the progression of BclA localization across the spore (light purple or gray long arrows); with a tailing cleavage event (darker gray or purple short arrows) that incorporates the localized BclA into the basal layer. Free N-terminal residues are found in the mother cell cytoplasm. FIG. 10E illustrates that incorporation of the localized BclA proteins is almost complete, with subsequent increase in N-terminal peptides in the mother cell compartment. CLR is the collagen-like repeat domain of the BclA protein.

FIGS. 11A and 11B show late stage sporulating cells ($T_7$). FIGS. 11C and 11D show released spores. FIGS. 11B and 11D are bright field images of the spores or sporulating cells, respectively, whose fluorescence is shown FIGS. 11A and 11C.

FIGS. 12A-12B show micrographs of the pBT1744 construct (*B. anthracis* BclA N-terminal domain fused to EGFP) localized and attached to the spores of both *B. cereus* 14579 (FIG. 12A) and *B. thuringiensis kurstaki* (FIG. 12B).

FIG. 13A shows *B. anthracis* control spores. FIGS. 13A-13C are bright field images of the respective micrographs shown in FIGS. 13D-13F. FIGS. 13D-13F show binding (green) by all antibodies in sera following exposure to protein A-FITC conjugate.

FIGS. 14A and 14B are bright field images of the respective micrographs shown in FIGS. 14C and 14D that show binding (green) by all antibodies in sera following exposure to protein A-FITC conjugate.

FIG. 15 shows a SDS-PAGE western blot of the extracted proteins of the spore layers from the *B. thuringiensis* spores expressing the PRRSV ORF5 protein fused to the BclA protein from immune or preimmune pig sera. Lanes 1 and 3 shows wild type *B. thuringiensis*. Lanes 2 and 4 show the specific reactivity of the immune sera to the PRRSV ORF5 band. Lanes 1 and 2 are from preimmune pig sera, and lanes 3 and 4 are from PRRSV immune pig sera.

FIG. 20A shows the HPLC reading of control spores (blue) and AtzA expressing spores (red) 10 h after initiating the incubation. FIG. 20B graphically depicts the percentage of atrazine and hydroxyatrazine over the course of the incubation. FIG. 20C shows the chemical structures for the conversion of atrazine to hydroxyatrazine. FIGS. 20D and E show the HPLC readings of AtzA expressing spores at Day 0 (FIG. 20D) and Day 10 (FIG. 20E).

DETAILED DESCRIPTION

Figure 2B:
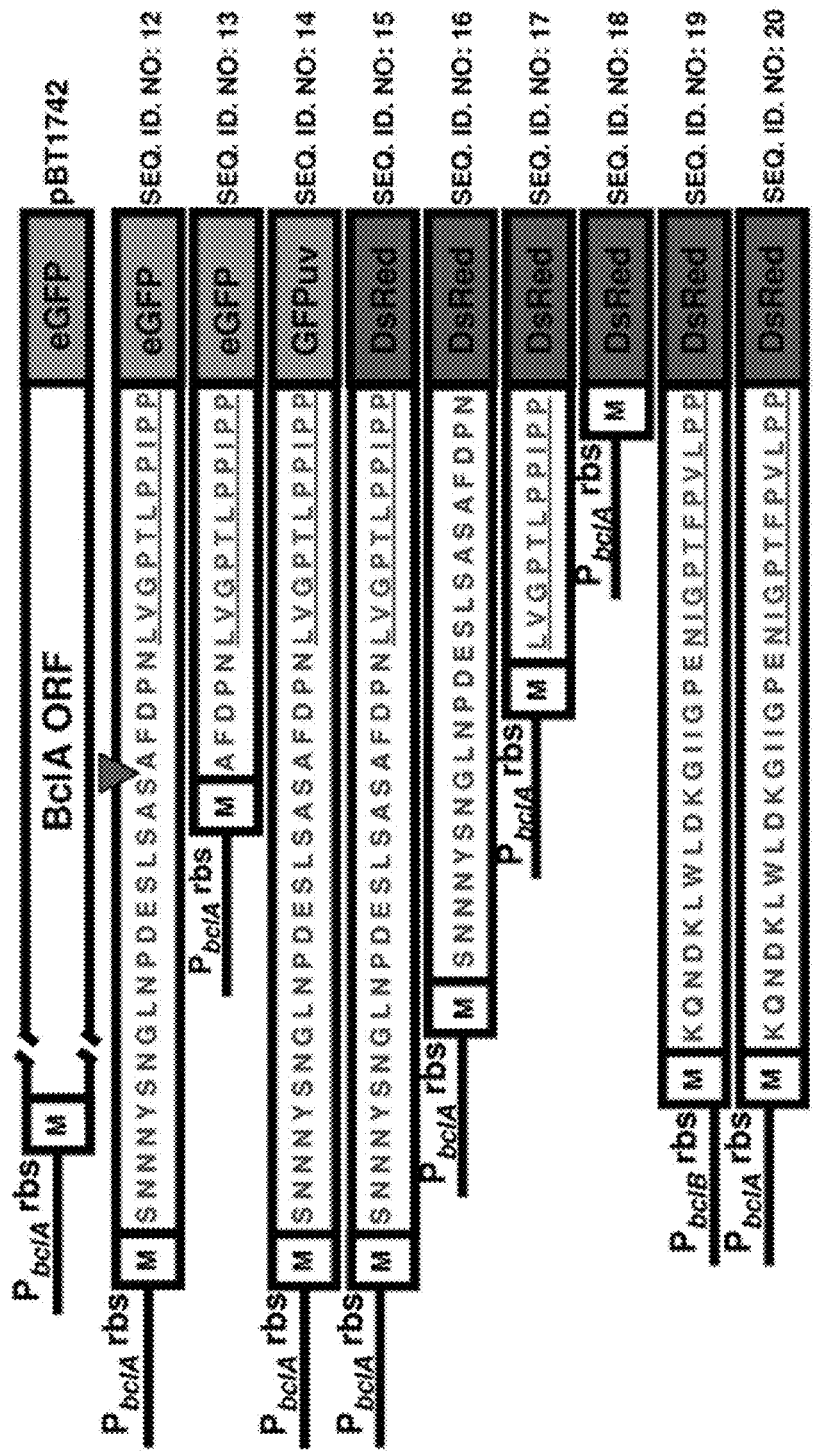
FIG. 2B diagrams the constructs described herein. Conserved regions are underlined. The arrow (▼) corresponds to the site of a previously described cleavage event. The designations of the corresponding fusion-encoding plasmids for the constructs are as follows: SEQ ID NO: 12 is pBT1744; SEQ ID NO: 13 is pBT1750; SEQ ID NO: 14 is pBT1693; SEQ ID NO: 15 is pBT1694; SEQ ID NO: 16 is pBT1701; SEQ ID NO: 17 is pBT1720; SEQ ID NO: 18 is pBT1729; SEQ ID NO: 19 is pBT1747; and SEQ ID NO: 20 is pBT1746.
Figure 30:
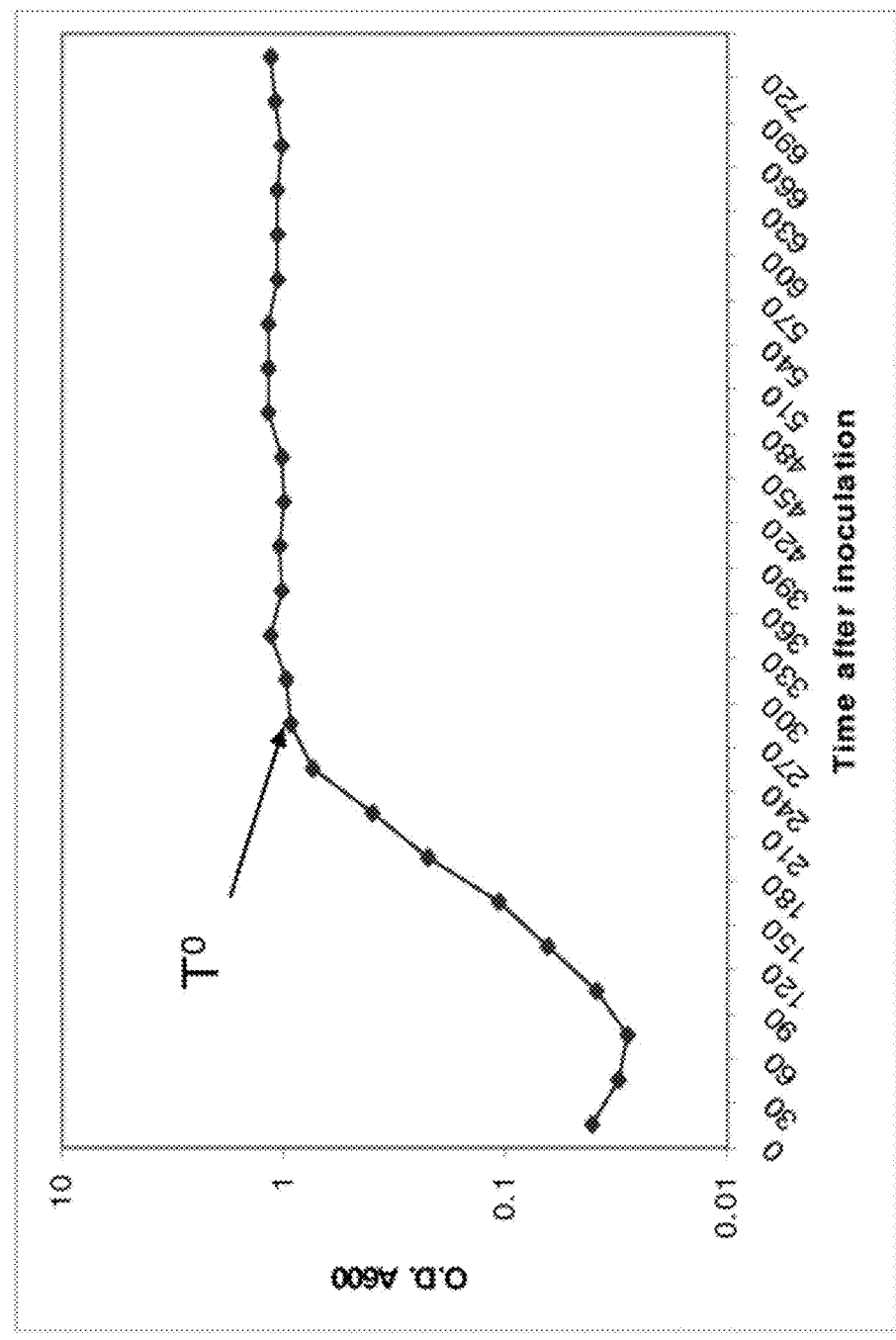

The present invention relates to the delivery of molecules to an environment or subject that would benefit from the presence or activity of the molecule. In particular, a procedure to efficiently localize molecules of interest (MOI) to the outer layers of exosporium-containing *Bacillus* spores has been discovered for the delivery to an environment. Herein, are identified sequences of the BclA and BclB glycoproteins responsible for the insertion of MOIs into the exosporium layer of the spore. These sequences can be used as targeting domains to incorporate MOIs onto the spore surface. As such, herein is described a *Bacillus* exosporium molecule delivery (BEMD) system that provides a means to deliver MOIs to an environment in need of the MOI or activity of the MOI. Furthermore, this novel delivery system can be exploited to incorporate MOIs into the exosporium of the *Bacillus* family of bacteria, including *B. anthracis*, *B. cereus*, and *B. thuringiensis*, thus, resulting in the surface display of MOIs. In particular, the BEMD system described herein may be useful in vaccine development, remediation technology, biofuels, fuel cells, and other endeavors.

Identification of Domains Important in Protein Incorporation into the Exosporium Two collagen-like glycoproteins, BclA and BclB, have been shown to be surface exposed on spores of *B. anthracis*. The BclA and BclB are found in the exosporium layer of *B. anthracis* spores. The protein BclA is the major constituent of the surface nap and has been shown to be attached to the exosporium with its N terminus positioned at the basal layer and its C-terminus extending outward from the spore. BclA extracted from spores has been shown to lack its N-terminal 19 amino acids, which suggests that a proteolytic event is involved in the incorporation of this protein into the exosporium. The mechanisms by which BclA and BclB are incorporated into the exosporium are unknown. Herein, sequences at the N-terminus of these Bcl proteins that are sufficient for the incorporation of the proteins into the exosporium have been identified. Additional proteins are encoded in the *B. anthracis* genome with collagen-like triplet amino acid repeats. These determinants possess sequences resembling $\sigma^K$ promoter elements, and each is expressed during the sporulation phase of the *B. anthracis* life cycle. The N-termini of these proteins possess interesting sequence similarities (FIG. 2A).

The N-terminal domains of BclA and BclB allow for the targeting and incorporation of these proteins into the exosporium of *Bacillus* family members. The BclA N-terminal domain comprises an 11 amino acid conserved motif, SEQ ID NO: 11, described herein and a 24 amino acid N-terminal region that contains a putative proteolytic cleavage site. A suggested role of the conserved motif is as a potential recognition site that leads to the positioning of the proteins to their appropriate target sites within the exosporium layer, but the attachment of proteins relies on more N-terminal sequences. Interestingly, addition of only 5 additional amino acids to the conserved motif (amino acids 20-24) allows for efficient localization and attachment of proteins, suggesting a role for those 5 amino acids in attachment of BclA to the exosporium. Removal of the conserved motif (but retention of the N-terminal amino acid sequence) leads to poor incorporation of the fusion proteins into the exosporium. The low level of incorporation observed may result from reduced positioning of the proteins at their sites of incorporation (limited fluorescence targeted to the exosporium of developing spores), but those proteins that are aligned properly get incorporated. The role of the proteolytic cleavage event has yet to be elucidated, but the data suggest that removal of the N-terminus prior to the putative cleavage site does not lead to a change in the level of protein incorporation into the exosporium. If a cleavage event is required for incorporation of BclA, the single methionine residue upstream of the cleavage site is sufficient for cleavage to occur. Alternatively, no cleavage event is required for exosporium incorporation and the cleavage event may be involved in release of the protein from the spore.

The process of assembly and attachment of BclA and BclB has not been described in detail to date. It is known that the BxpB (also called ExsFA) protein is involved directly or indirectly in the assembly of BclA on the surface of the exosporium, as bxpB mutant spores do not contain a BclA-coated nap. The N-terminal domains of BclA and BclB are responsible for the targeting and incorporation of these proteins into the exosporium of *B. anthracis*. FIGS. 10A-10E represent a model for the maturation and assembly of BclA into the exosporium. Production of BclA protein occurs early in sporulation, before the spore is visible within the mother cell by phase contrast microscopy (FIG. 10A). Soon thereafter, BclA localizes to the pole of the endospore facing the mother cell compartment (FIG. 10B). The BclA fusion protein begins to localize from the tip of the pole of the spore to encompass the newly formed exosporium basal layer around the spore (FIG. 10C). This localization is dependent on the presence of the conserved motif, amino acids 25-35 of BclA. Loss of this motif leads to greatly diminished BclA localization and subsequently poor incorporation. The pattern of initial exosporium development is consistent with previous studies, suggesting that exosporium assembly initiation is spatially regulated in the sporulating cell. This nap assembly pattern is presumably due to positioning of a protein or protein complex in the basal layer that recognizes the conserved motif in BclA. Fusions containing only the conserved motif localize to the mother cell center-facing pole of the spore. The motif only fusion localizes in a pattern following the newly formed basal layer across the spore, but this fusion is released at a time corresponding to the cleavage event. Because this fusion construct lacks the N-terminal cleavage site, it cannot be processed and is not stably incorporated.

Maturation of the exosporium basal layer and the beginning of nap assembly occur at the same pole as that involved in the initiation of basal layer assembly. This initial localization of BclA is to an area smaller than the described 'cap,' suggesting that the cap in exsY mutant spores results from a stalling in the progression of the exosporium development, rather than a broader initial deposition of BclA. It is proposed herein that the conserved domain is a localization domain that is recognized by an exosporium protein or complex that positions BclA for subsequent cleavage and incorporation.

Subsequent to positioning of BclA around the spore, cleavage of the N-terminal domain after residue 19 occurs concomitantly with stable incorporation of the protein into the exosporium (FIG. 10D). This cleavage event follows the localization of BclA around the spore from one pole to the other (FIG. 10E). Fusion constructs that contain a 'pre-cleaved' N-terminus both localize and attach efficiently to the exosporium. This may indicate that the cleavage event per se is not required for the actual incorporation, but may create the proper substrate for the incorporation event. Studies are underway to determine if the N-terminal methionine residue is removed during incorporation, which would suggest a requirement for the proteolytic event.

Correct localization of the proteins in the exosporium driven by the N-terminal domain (NTD) alone suggests that recognition of the N-terminal sequence is key in the nap assembly process. Glycosylation of the collagen-like repeat region of BclA and the trimerization of the BclA protein owing to the presence of these repeats do not appear to be necessary for recognition and incorporation of BclA into the exosporium.

BclB is produced in lower quantities in the mother cell in comparison with BclA. Expression of BclB under the more active bclA promoter allows for incorporation of BclB fusions into the exosporium. However, the pattern of incorporation differs from the uniform distribution observed with the BclA fusions. Differences in the N-terminal amino acid sequences may result in interactions with a different set of exosporium proteins, which may account for the different localization results.

Exploitation of the Targeting Domains as a *Bacillus* Exosporium Molecule Delivery (BEMD) System During the sporulation process in *Bacillus*, spores are assembled with the outermost spore layers deposited last. The BclA glycoprotein is the predominant protein on the exosporium nap layer. This exosporium surface protein is expected to be among the last of the spore proteins to be incorporated into the spore. Data herein show that the N-terminal domains of the BclA and BclB proteins are sufficient for localization to the exosporium surface and that efficient expression on the spore surface is also dependent on the timing or levels of expression during sporulation. Amino acid sequences distal to the first 35 amino acids of the BclA protein are not required for surface localization on spores and can be replaced with MOIs that can be incorporated into fusions of the types described herein.

Use of the *Bacillus* exosporium molecule delivery (BEMD) system is expected to allow for high expression of MOIs in the endospore of *Bacillus* family members. The amount of incorporation surpasses that of recombinant proteins expressed on *B. subtilis* spores using the CotB/C systems.

Composition of the BEMD System

The BEMD system includes bacteria from the *Bacillus* family expressing a fusion construct. The fusion construct includes at least one positioning sequence and at least one MOI. The positioning sequence encodes about the first 50 amino acids of the N-terminal domain (NTD) of a *Bacillus* exosporium protein. Suitable *Bacillus* exosporium proteins may be derived from any *Bacillus* family member. Exemplary *Bacillus* exosporium proteins include *Bacillus* BclA, BclB, BAS3290 (BclE), and combinations thereof. The *Bacillus* exosporium protein may also be a conserved sequence derived from natural occurring *Bacillus* exosporium proteins.

The positioning sequence may encode about the first 50 amino acids of the NTD of a *Bacillus* exosporium protein. Preferably, the positioning sequence encodes about the first 5, 10, 15, 20, 25, 30, 35, 40, or 45 amino acids of the NTD of a *Bacillus* protein.

The positioning sequence and MOI are combined into a fusion construct through molecular cloning techniques well known in the art. A skilled artisan will appreciate the ability to enhance the attributes of the fusion construct through molecular cloning and mutagenesis techniques well known in the art. Suitable enhancements may include adding spacer sequences to improve native folding of the MOI, alteration of the MOI sequence to enhance activity or expression and alteration of the positioning sequence to alter the position of the MOI on the surface of the exosporium. These alteration and enhancement techniques are well known in the art.

The MOIs used with the BEMD system may be any molecule of interest. Preferably, the MOI is a molecule capable of being genetically expressed from a DNA sequence. The DNA sequence is fused to a positioning sequence to target its expression product to the outer most portion of an exosporium. The MOI sequence may be separated from the positioning sequence by about 1 to 100 nucleotides. The MOI sequence may be an enzyme. Suitable enzymes may be natural, synthetic, or genetically altered to enhance desired properties. Exemplary enzyme classes include oxidoreductases, transferases, hydrolases, lyases, isomerases, and ligases. The MOI sequence may be an immunogen or antigen.

Once generated, the fusion construct is cloned into a shuttle plasmid. The shuttle plasmid is then transformed into the desired *Bacillus* family member generating bioparticles. These bioparticles (i.e. transformed bacteria) containing the shuttle plasmid and, thus, the fusion construct are grown into batches of suitable size for the application. Suitable shuttle plasmids contain a replication origin, antibiotic selection elements and a multiple cloning site. Many suitable shuttle plasmids are known in the art that can be used with the present invention.

Depending upon the desired use of the BEMD system, the bioparticles may be further manipulated to remove the MOI or inactivate the bacterium. Removal of the MOI may be by any method known in the art. Preferably, the fusion construct contains a cleavage sequence between the positioning sequence and the sequence of the MOI. Substances, such as proteolytic enzymes that recognize the cleavage sequence used may be applied to the bioparticle to remove the MOI. The MOI may then be separated from the remaining bioparticle through methods known in the art such as centrifugation.

Once the BEMD system is generated and the desired amount is produced, it may be inactivated to prevent further germination once in use. There are several methods known in the art for inactivating bacteria germination and any method can be used that is accepted in the industry. Such methods include, without limitation, UV exposure, heat treatment, and irradiation. Exposure to ultraviolet (UV) radiation is a preferred method of inactivating spores; however, any of the compatible, inactivation methods known in the art may be used. Alternatively, spores derived from nontoxigenic strains, or genetically or physically inactivated strains, could be developed as part of a delivery system. This system would provide the important MOI without the problems associated with residual.

The delivery of the BEMD bioparticles to an environment or subject may be by any methods known in the art. The method of delivery will be dependent upon the desired use of the BEMD bioparticles. For instance, for bioremediation the BEMD bioparticles need to be added to the biomass, soil, or liquid. Agitation or dry mixing of the bioparticles may enhance their activity. Additionally, a slurry of BEMD bioparticles may be made with an amount of solution which is then added to the biomass, soil, surface or liquid followed by spreading, mixing, or agitation. Alternatively, if the BEMD system is to be delivered to a subject it will need to be administered as defined herein. Methods of administration may require the BEMD bioparticles to be mixed with pharmaceutical-acceptable or veterinary-acceptable carriers.

Methods of Use

As can be appreciated, the present invention has numerous uses across numerous fields. Advantageously, the method of using the present invention is basically similar despite the field of use. In particular, the MOI and method of delivery may change depending on the use, but the basic platform does not. As the uses of the invention are too numerous to enumerate herein, the scope of the invention should not be limited to the exemplary uses described herein.

Vaccine Development

The BEMD system has implications for the development of potentially better and safer vaccines. The MOI may be an immunogen or antigen. Important immunogens could be expressed on the surface of a spore from the *Bacillus* family using any of the methods of the present invention. Herein, the BEAD system is demonstrated using well-known reporter proteins and a well-characterized antigen of viral origin. It is expected that any suitable antigen or small molecule may be recombined using the methods herein. Suitable antigens or small molecules are those that are known or expected to illicit a desired immune response that is sufficient to yield a therapeutic or protective effect when expressed on the exterior of a *Bacillus* spore. Suitability, in large part the use of an immunogen will be determined by the folding in the three-dimensional structure once the recombinant antigen is incorporated into the exosporium, i.e. the antigenic portion(s) of the recombinant molecule must be available for detection by the immune system.

Immunogenic MOIs may be any antigen currently used to produce vaccines and those discovered in the art. Exemplary disease and conditions from which immunogenic MOIs may be derived include the following: Acintobacter infections, caused by *Acinetobacter baumannii*; Actinomycosis, caused by *Actinomyces israelii, Actinomyces gerencseriae*, and *Propionibacterium propionicus*; African sleeping sickness, caused by *Trypanosoma brucei*; Acquired immune deficiency syndrome (AIDS), caused by Human immunodeficiency virus; Amebiasis, caused by *Entamoeba histolytica*; Anaplasmosis, caused by *Anaplasma* genus, Anthrax, caused by *Bacillus anthracis; Arcanobacterium haemolyticum* infection, caused by *Arcanobacterium haemolyticum*; Argentine hemorrhagic fever, caused by Junin virus; Ascariasis, caused by *Ascaris lumbricoides*, Astrovirus infection, caused by Astroviradae family; Babesiosis, *Babesia* genus; *Bacillus cereus* infection, caused by *Bacillus cereus*; Bacterial pneumonia; Bacterial vaginosis; *Bacteroides* infection, caused by *Bacteroides* genus; Balantidiasis, caused by *Balantidium coli; Baylisascaris* infection, caused by *Baylisascaris* genus; BK virus infection, caused by BK virus; Black piedra, caused by *Piedraia hortae; Blastocystis hominis* infection, caused by *Blastocystis hominis*; Blastomycosis, caused by *Blastomyces dermatitidis*; Bolivian hemorrhagic fever, caused by Machupo virus; *Borrelia* infection, caused by *Borrelia* genus; Botulism (and Infant botulism), caused by *Clostridium botulinum*; Note: Botulism is not an infection by *Clostridium botulinum* but caused by the intake of botulinum toxin; Brazilian hemorrhagic fever, caused by Sabia; Brucellosis, caused by *Brucella* genus; *Burkholderia* infection, caused by usually *Burkholderia cepacia* and other *Burkholderia* species; Buruli ulcer, caused by *Mycobacterium ulcerans*; Calicivirus infection (Norovirus and Sapovirus), caused by Caliciviridae family; Campylobacteriosis, caused by *Campylobacter* genus; Candidiasis (Moniliasis; Thrush) usually *Candida albicans* and other *Candida* species; Cat-scratch disease, caused by *Bartonella henselae*; Cellulitis, caused by usually Group A *Streptococcus* and *Staphylococcus*; Chagas Disease (American trypanosomiasis), caused by *Trypanosoma cruzi*; Chancroid, caused by *Haemophilus ducreyi*; Chickenpox, caused by Varicella zoster virus (VZV); Chlamydia, caused by *Chlamydia trachomatis; Chlamydophila pneumoniae* infection, caused by *Chlamydophila pneumoniae*; Cholera, caused by *Vibrio cholerae*; Chromoblastomycosis, caused by usually *Fonsecaea pedrosoi*; Clonorchiasis, caused by *Clonorchis sinensis; Clostridium difficile* infection, caused by *Clostridium difficile*; Coccidioidomycosis, caused by *Coccidioides immitis* and *Coccidioides posadasii*; Colorado tick fever (CTF), caused by Colorado tick fever virus (CTFV); Common cold (Acute viral rhinopharyngitis; Acute coryza), caused by usually rhinoviruses and coronaviruses; Creutzfeldt-Jakob disease (CJD), caused by CJD prion; Crimean-Congo hemorrhagic fever (CCHF), caused by Crimean-Congo hemorrhagic fever virus; Cryptococcosis, caused by *Cryptococcus neoformans*; Cryptosporidiosis, caused by *Cryptosporidium* genus; Cutaneous larva migrans (CLM), caused by usually *Ancylostoma braziliense*; multiple other parasites; Cyclosporiasis, caused by *Cyclospora cayetanensis*; Cysticercosis, caused by *Taenia solium*; Cytomegalovirus infection, caused by Cytomegalovirus; Dengue fever, caused by Dengue viruses (DEN-1, DEN-2, DEN-3 and DEN-4)—Flaviviruses; Dientamoebiasis, caused by *Dientamoeba fragilis*; Diphtheria, caused by *Corynebacterium diphtheriae*; Diphyllobothriasis, caused by *Diphyllobothrium*; Dracunculiasis, caused by *Dracunculus medinensis*; Ebola hemorrhagic fever, caused by Ebolavirus (EBOV); Echinococcosis, caused by *Echinococcus* genus; Ehrlichiosis, caused by *Ehrlichia* genus; Enterobiasis (Pinworm infection), caused by *Enterobius vermicularis; Enterococcus* infection, caused by *Enterococcus* genus; Enterovirus infection, caused by Enterovirus genus; Epidemic typhus, caused by *Rickettsia prowazekii*; Erythema infectiosum (Fifth disease), caused by Parvovirus B19; Exanthem subitum, caused by Human herpesvirus 6 (HHV-6) and Human herpesvirus 7 (HHV-7); Fasciolopsiasis, caused by *Fasciolopsis buski*; Fasciolosis, caused by *Fasciola hepatica* and *Fasciola gigantica*; Fatal familial insomnia (FFI), caused by FFI prion; Filariasis, caused by Filarioidea superfamily; Food poisoning by *Clostridium perfringens*, caused by *Clostridium perfringens*; Free-living amebic infection; *Fusobacterium* infection, caused by *Fusobacterium* genus; Gas gangrene (Clostridial myonecrosis), caused by usually *Clostridium perfringens*; other *Clostridium* species; Geotrichosis, caused by *Geotrichum candidum*; Gerstmann-Sträussler-Scheinker syndrome (GSS), caused by GSS prion; Giardiasis, caused by *Giardia intestinalis*; Glanders, caused by *Burkholderia mallei*; Gnathostomiasis, caused by *Gnathostoma spinigerum* and *Gnathostoma hispidum*; Gonorrhea, caused by *Neisseria gonorrhoeae*; Granuloma inguinale (Donovanosis), caused by *Klebsiella granulomatis*; Group A streptococcal infection, caused by *Streptococcus pyogenes*; Group B streptococcal infection, caused by *Streptococcus agalactiae; Haemophilus influenzae* infection, caused by *Haemophilus influenzae*; Hand, foot and mouth disease (HFMD), caused by Enteroviruses, mainly Coxsackie A virus and Enterovirus 71 (EV71); Hantavirus Pulmonary Syndrome (HPS), caused by Sin Nombre virus; *Helicobacter pylori* infection, caused by *Helicobacter pylori*; Hemolytic-uremic syndrome (HUS), caused by *Escherichia coli* O157:H7; Hemorrhagic fever with renal syndrome (HFRS), caused by Bunyaviridae family; Hepatitis A, caused by Hepatitis A Virus; Hepatitis B, caused by Hepatitis B Virus; Hepatitis C, caused by Hepatitis C Virus; Hepatitis D, caused by Hepatitis D Virus; Hepatitis E, caused by Hepatitis E Virus; Herpes simplex, caused by Herpes simplex virus 1 and 2 (HSV-1 and HSV-2); Histoplasmosis, caused by *Histoplasma capsulatum*; Hookworm infection, caused by *Ancylostoma duodenale* and *Necator americanus*; Human bocavirus infection, caused by Human bocavirus (HBoV); Human *ewingii* ehrlichiosis, caused by *Ehrlichia ewingii*; Human granulocytic anaplasmosis (HGA), caused by *Anaplasma phagocytophilum*; Human metapneumovirus infection, caused by Human metapneumovirus (hMPV); Human monocytic ehrlichiosis, caused by *Ehrlichia chaffeensis*; Human papillomavirus (HPV) infection, caused by Human papillomavirus (HPV); Human parainfluenza virus infection, caused by Human parainfluenza viruses (HPIV); Hymenolepiasis, caused by *Hymenolepis nana* and *Hymenolepis diminuta*; Epstein-Barr Virus Infectious Mononucleosis (Mono), caused by Epstein-Barr Virus (EBV); Influenza (flu), caused by Orthomyxoviridae family; Isosporiasis, caused by *Isospora Belli*; Kawasaki disease, caused by unknown; evidence supports that it is infectious; Keratitis; *Kingella kingae* infection, caused by *Kingella kingae*; Kuru, caused by Kuru prion; Lassa fever, caused by Lassa virus; Legionellosis (Legionnaires' disease), caused by *Legionella pneumophila*; Legionellosis (Pontiac fever), caused by *Legionella pneumophila*; Leishmaniasis, caused by *Leishmania* genus; Leprosy, caused by *Mycobacterium leprae* and *Mycobacterium lepromatosis*; Leptospirosis, caused by *Leptospira* genus; Listeriosis, caused by *Listeria monocytogenes*; Lyme disease (Lyme borreliosis), caused by usually *Borrelia burgdorferi* and other *Borrelia* species; Lymphatic filariasis (Elephantiasis), caused by *Wuchereria bancrofti* and *Brugia malayi*; Lymphocytic choriomeningitis, caused by Lymphocytic choriomeningitis virus (LCMV); Malaria, caused by *Plasmodium* genus; Marburg hemorrhagic fever (MHF), caused by Marburg virus; Measles, caused by Measles virus; Melioidosis (Whitmore's disease), caused by *Burkholderia pseudomallei*; Meningitis; Meningococcal disease, caused by *Neisseria meningitidis*; Metagonimiasis, caused by usually *Metagonimus yokagawai*; Microsporidiosis, caused by Microsporidia phylum; Molluscum contagiosum (MC), caused by Molluscum contagiosum virus (MCV); Mumps, caused by Mumps virus; Murine typhus (Endemic typhus), caused by *Rickettsia typhi; Mycoplasma* pneumonia, caused by *Mycoplasma pneumoniae*; Mycetoma, caused by numerous species of bacteria (Actinomycetoma) and fungi (Eumycetoma); Myiasis, caused by parasitic dipterous fly larvae; Neonatal conjunctivitis (Ophthalmia neonatorum), caused by most commonly *Chlamydia trachomatis* and *Neisseria gonorrhoeae*; (New) Variant Creutzfeldt-Jakob disease (vCJD, nvCJD), caused by vCJD prion; Nocardiosis, caused by usually *Nocardia asteroides* and other *Nocardia* species; Onchocerciasis (River blindness), caused by *Onchocerca volvulus*; Paracoccidioidomycosis (South American blastomycosis), caused by *Paracoccidioides brasiliensis*; Paragonimiasis, caused by usually *Paragonimus westermani* and other *Paragonimus* species; Pasteurellosis, caused by *Pasteurella* genus; Pediculosis capitis (Head lice), caused by *Pediculus humanus capitis*; Pediculosis corporis (Body lice), caused by *Pediculus humanus corporis*; Pediculosis pubis (Pubic lice, Crab lice), caused by Phthirus pubis; Pelvic inflammatory disease (PID); Pertussis (Whooping cough), caused by *Bordetella pertussis*; Plague, caused by *Yersinia pestis*; Pneumococcal infection, caused by *Streptococcus pneumoniae*; Pneumocystis pneumonia (PCP), caused by *Pneumocystis jirovecii*; Pneumonia; Poliomyelitis, caused by Poliovirus; *Prevotella* infection, caused by *Prevotella* genus; Primary amoebic meningoencephalitis (PAM), caused by usually *Naegleria fowleri*; Progressive multifocal leukoencephalopathy, caused by JC virus; Psittacosis, caused by *Chlamydophila psittaci*; Q fever, caused by *Coxiella burnetii*; Rabies, caused by Rabies virus; Rat-bite fever, caused by *Streptobacillus moniliformis* and *Spirillum minus*; Respiratory syncytial virus infection, caused by Respiratory syncytial virus (RSV); Rhinosporidiosis, caused by *Rhinosporidium seeberi*; Rhinovirus infection, caused by Rhinovirus; Rickettsial infection, caused by *Rickettsia* genus; Rickettsialpox, caused by *Rickettsia akari*; Rift Valley fever (RVF), caused by Rift Valley fever virus; Rocky mountain spotted fever (RMSF), caused by *Rickettsia rickettsii*; Rotavirus infection, caused by Rotavirus; Rubella, caused by Rubella virus; Salmonellosis, caused by *Salmonella* genus; SARS (Severe Acute Respiratory Syndrome), caused by SARS coronavirus; Scabies, caused by *Sarcoptes scabiei*; Schistosomiasis, caused by *Schistosoma* genus; Sepsis; Shigellosis (Bacillary dysentery), caused by *Shigella* genus; Shingles (Herpes zoster), caused by Varicella zoster virus (VZV); Smallpox (Variola), caused by Variola major or Variola minor; Sporotrichosis, caused by *Sporothrix schenckii*; Staphylococcal food poisoning, caused by *Staphylococcus* genus; Staphylococcal infection, caused by *Staphylococcus* genus; Strongyloidiasis, caused by *Strongyloides stercoralis*; Syphilis, caused by *Treponema pallidum*; Taeniasis, caused by *Taenia* genus; Tetanus (Lockjaw), caused by *Clostridium tetani*; Tinea barbae (Barber's itch), caused by usually *Trichophyton* genus; Tinea capitis (Ringworm of the Scalp), caused by usually *Trichophyton tonsurans*; Tinea corporis (Ringworm of the Body), caused by usually *Trichophyton* genus; Tinea cruris (Jock itch), caused by usually *Epidermophyton floccosum, Trichophyton rubrum*, and *Trichophyton mentagrophytes*; Tinea manuum (Ringworm of the Hand), caused by *Trichophyton rubrum*; Tinea nigra, caused by usually *Hortaea werneckii*; Tinea pedis (Athlete's foot), caused by usually *Trichophyton* genus; Tinea unguium (Onychomycosis), caused by usually *Trichophyton* genus; Tinea versicolor (*Pityriasis versicolor*), caused by *Malassezia* genus; Toxocariasis (Ocular Larva Migrans (OLM)), caused by *Toxocara canis* or *Toxocara cati*; Toxocariasis (Visceral Larva Migrans (VLM)), caused by *Toxocara canis* or *Toxocara cati*; Toxoplasmosis, caused by *Toxoplasma gondii*; Trichinellosis, caused by *Trichinella spiralis*; Trichomoniasis, caused by *Trichomonas vaginalis*; Trichuriasis (Whipworm infection), caused by *Trichuris trichiura*; Tuberculosis, caused by usually *Mycobacterium tuberculosis*; Tularemia, caused by *Francisella tularensis; Ureaplasma urealyticum* infection, caused by *Ureaplasma urealyticum*; Venezuelan equine encephalitis, caused by Venezuelan equine encephalitis virus; Venezuelan hemorrhagic fever, caused by Guanarito virus; Viral pneumonia; West Nile Fever, caused by West Nile virus; White piedra (Tinea blanca), caused by *Trichosporon beigelii*; *Yersinia pseudotuberculosis* infection, caused by *Yersinia pseudotuberculosis*; Yersiniosis, caused by *Yersinia enterocolitica*; Yellow fever, caused by Yellow fever virus; Zygomycosis, caused by Mucorales order (Mucormycosis) and Entomophthorales order (Entomophthoramycosis).

Production of Biofuels

The BEMD system may be used in the production of biofuels. It is contemplated that the MOI is any enzyme or combination of enzymes capable of hydrolyzing starch, sucrose, lactose, cellulose or hemicelluloses into fermentable sugars. These sugars can be further fermented using enzymes capable of using the sugars to produce ethanol. The BEMD system can be delivered to a biomass such as agricultural crops, such as corn, sugar cane and sugar beet, or from agricultural byproducts, such as whey and potato processing waste streams to aide in the production of ethanol.

Use of the BEMD system provides an improved production step for delivery of the desired enzymes. After the fuel and/or other compounds produced can be recovered by suitable processing methods depending on the particular material produced and the level of purity desired. For example, when producing ethanol the entire contents of the reaction can be transferred to a distillation unit, and 96 percent ethanol/4 percent water (by volume) can be distilled and collected. Fuel grade ethanol (99-100 percent ethanol) can be obtained by azeotropic distillation of the 96 percent ethanol, e.g., by the addition of benzene and then re-distilling the mixture, or by passing the 96 percent ethanol through molecular sieves to remove the water.

Production of Biodiesel

The BEMD system may be used in the production of biodiesel. The conversion of vegetable oils to methyl- or other short chain esters in a single transesterification reaction using lipases has led to the production of high-grade biodiesel. It is contemplated that the BEMD system will incorporate an MOI that is a lipase. Exemplary lipases include, without limitation, lipases such as those from *Pseudomonas cepacia, Rhizomocur miehei* and *Candida antarctica*. One skilled in the art will recognize that any lipase or combination of lipases could be used as MOIs with the BEMD system in the production of biodiesel. Use of the BEMD system provides an improved production step for delivery of the lipases used in the production of an energy source.

Bioremediation

The BEMD system of the present invention can be utilized in the remediation of contaminants. The BEMD system aides in the delivery of enzymes known in the art for the reduction of contaminants. Enzymes known in the art of having the capability of breaking down or converting contaminants to less harmful substances can be used as MOIs with the BEMD system of the present invention. Suitable enzymes that may be used as MOIs, without limitation, include mono- or di-oxygenases, reductases, dehalogenases, cytochrome P450 monooxygenases, enzymes involved in lignin metabolism such as laccases, lignin- and manganese peroxidases and bacterial phophotriesteraes. Suitable enzymes also include natural occurring, synthetic, and genetically engineered enzymes. By way of example, the enzyme AtzA produced by soil bacterium *Pseudomonas* strain ADP, is capable of modifying the contaminant atrazine to the benign substance hydroatrazine (FIGS. 20A-20E). By way of example the contaminated environments can include, but not limited to liquid environments, such as water, solid or semi-solid environments, such as soil, or gaseous environments, such as air.

Exemplary contaminates include the following: polycyclic aromatic hydrocarbons (PAHs), polynitrated aromatic compounds, pesticides such as organochlorine insecticides, bleach-plant effluents, synthetic dyes, polymers, wood preservatives, chrysene, benzol[a]pyrene, coronene, dibenzothiophenes, cloro-dibenzofurans, cloro-dibenzo p-dioxines, atrazine, lindane, polychlorinated biphenyl, synthetic pyrethroids, carbamates, and organophosphates to name a few.

Exemplary enzymes that may be used as MOIs include the following: mono- or di-oxygenases, reductases, dehalogenases, cytochrome P450 monooxygenases, enzymes involved in lignin-metabolism such as laccases, lignin and manganese peroxidases, and phosphotriesterases to name a few.

The BEMD system of the present invention may be combined with methods known in the art for remediation. Suitable methods known in the art include, without limitation, bioremediation, vacuum or air stripping, immobilization, and soil washing-flushing. Immobilization is one of the more common methods, where solid matrices are introduced into the soil that bind or otherwise minimize migration of the contaminate from the initial site. Soil washing-flushing involves the introduction of aqueous solution to the subsurface to mobilize the contaminates for treatment. It is contemplated that the BEMD system can be combined with soil-washing techniques to introduce the BEMD particles to the subsurface. Also, BEMD particles can be mixed into soil slurry and added to soil or incorporated inot the desired environment through the use of soil tillage.

Fuel Cell

The BEMD system of the present invention can be utilized in fuel cells. The BEMD system aides in the delivery of enzymes known in the art for the production of an energy source. Enzymes known in the art of having the capability of breaking down organic material can be used as MOIs with the BEMD system of the present invention. BEMD systems expressing one or more of such enzymes as MOIs can be used with devices that directly convert biocatalyst power generated from the degradation of organic matter into electrical energy. Exemplary enzymes include without limitation hydrogenases, laccases and other redox enzymes that have application as electrocatalysts. In the field of biofuel cells, hydrogenases have been demonstrated that convert hydrogen to generate an electric current and possess similar energy conversion efficiency to noble-metal-based commercial methods. Laccases have also been incorporated into the design of biofuel cells since they are one of the few enzymes that can accept electrons from the cathodic compartment of a biofuel cell.

By way of example and without limitation, the BEMD system can be contacted with environments containing organic material (i.e. biomass) such as wastewater and other undesirable substrates. As the enzymes delivered by the BEMD system degrade the organic material through oxidation, hydrolysis, and other degradation methods, the fuel cell device converts this power into electricity. Fuel cell devices are known in the art such as those described in U.S. Patent Application No. 20100178530, incorporated herein by reference. Several studies on electricity production from artificial or real domestic wastewater, animal wastewater, food wastewater, and recently hydrolysate from corn stover biomass has been conducted and for this purpose several different types of fuel cells have been developed both for batch and continuous mode operations.

Biohydrogen

The BEMD system of the present invention can be utilized in the production of molecular hydrogen as a renewable, efficient and pollution-free energy source. Hydrogen is colorless, odorless, tasteless, non-toxic and, on combustion, it produces water as the only byproduct. Hydrogen obtained from biomass has the potential to compete with hydrogen produced by other methods such as from natural gas, which requires the catalytic conversion of hydrocarbons or electrochemical or photochemical water splitting. Enzymes known in the art as hydrogenases can be used as MOIs with the BEMD system of the present invention. BEMD systems expressing one or more of such enzymes as MOIs can be used for the production of hydrogen, for example, by fermentation of sugar or, more preferably, from waste.

Biofilm Removal

Naturally occurring biofilms are continuously produced and often accumulate on numerous industrial surfaces and on biological surfaces. In an industrial setting, the presence of these biofilms causes a decrease in the efficiency of industrial machinery, requires increased maintenance, and presents potential health hazards. For example, the surfaces of water cooling towers become increasingly coated with microbially produced biofilm slime which both constricts water flow and reduces heat exchange capacity. Water cooling tower biofilms may also harbor pathogenic microorganisms such as *Legionella pneumophila*. Food preparation lines are routinely plagued by biofilm build-up both on the machinery and on the food product where biofilms often include potential pathogens. Industrial biofilms are complex assemblages of insoluble polysaccharide-rich biopolymers which are produced and elaborated by surface dwelling microorganisms. The chemical composition of industrial biofilms are diverse and are specific to each species of surface dwelling microorganism.

On a biological surface, the presence of these biofilms results in the growth of, and subsequent colonization by, pathogenic microorganisms on an internal or external surface of a host animal or on the surface of objects introduced into the animal (e.g. surgical implants). Animal pathogens which colonize surfaces are often maintained and protected by unique polysaccharide rich biofilms produced by the pathogen. Such biofilms coat the infected or colonized surface of the animal or implanted object and continue to be produced during the disease process. For many diseases, biofilms are required for the disease process to become established and to progress. The chemical compositions of pathogen-associated surface biofilms, which consist of complex mixtures of biopolymers, are specific to each species of pathogen.

The BEMD system can be utilized to treat and remove biofilms. Enzymes known in the art as hydrolytic enzymes can be used as MOIs with the BEMD system of the present invention. BEMD systems expressing one or more of such enzymes as MOIs can be delivered to biofilm environments such that the hydrolytic enzymes significantly degrade or remove the biofilm. Techniques are known in the art for biofilm removal such as those described in U.S. Patent Application No. 20100159563, incorporated herein by reference.

Drug Delivery

The BEMD system of the present invention may be utilized in delivering therapeutic molecules to a subject. Molecules such as therapeutic proteins may be used as MOIs with the BEMD system. These bioparticles may be administered to a subject by methods described herein. Suitable therapeutic proteins include those known in the art and those yet to be discovered.

Unless defined otherwise, all technical and scientific terms used herein have the same meaning as is commonly understood by one of skill in the art to which this invention belongs at the time of filing.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Experimental Procedures

Growth Conditions

*Bacillus anthracis* strain ΔSterne-1 was a gift from Dr. S. H. Leppla (National Institutes of Health, Bethesda, Md.). ΔSterne-1 is a strain derived from Sterne and lacks pX01 and pX02 (capsule- and toxin-negative). Sporulation was induced by growth on nutrient agar plates at 30° C. or in liquid culture using modified G Broth. Growth in liquid culture was monitored by absorbance at 600 nm. Sporulation was essentially complete (>95%) after 72 hours on nutrient agar plates. The degree of sporulation was assessed by phase contrast microscopy. Spores were harvested from 7-day old nutrient agar plates to ensure complete sporulation, washed 3 times in PBS, and stored at room temperature.

Creation of Fusion Constructs

Fusion constructs were created by polymerase chain reaction (PCR) amplification followed by splicing by overlapping extension as used in the art (see for example, Ho, et al., Gene 77: 51-59 (1989) and Horton, et al., Gene 77: 61-68 (1989)). Primers utilized in the PCR reactions are listed in Tables 1a and 1b. Correct fusions contained intact promoter regions including a as well as native RBS and start codons. Fusion constructs were then subcloned into the shuttle plasmid pMK4 (see Sullivan et al., 1984), followed by electroporation into the ΔSterne strain of *Bacillus anthracis*. Selection of electrotransformed cells was on tryptic soy agar plates containing chloramphenicol at 10 μg/ml. Verification of the correct identity of the plasmids in the transformed cells was accomplished by antibiotic selection, followed by DNA extraction and plasmid DNA sequencing from vegetative cells.

TABLE 1a

Polymerase Chain Reaction Primers.

| Fusion | * | Primer 1 | DNA Sequence | SEQ. ID. NO. |
|---|---|---|---|---|
| pBT1744 | US | 106 | ctcgagtaatcaccctcttccaaatc | 21 |
|  | DS | 177 | ttaccaccgataccaccaatggtgagcaagggcgagg | 22 |
| pBT1742 | US | 106 | ctcgagtaatcaccctcttccaaatc | 23 |
|  | DS | 158 | ccattattattgaaaaagttgctatggtgagcaagggcgagg | 24 |
| pBT1750 | US | 106 | ctcgagtaatcaccctcttccaaatc | 25 |
|  | DS | 213 | ggaggtgaatttatggcatttgaccctaatcttg | 26 |
| pBT1758 | US | 106 | ctcgagtaatcaccctcttccaaatc | 27 |
|  | DS | 243 | aaggctgccgcagcgatgtcaaataataattattcaaatgaccatgat | 28 |
| pBT1693 | US | 106 | ctcgagtaatcaccctcttccaaatc | 29 |
|  | DS | 65 | ccaccgataccaccaatgagtaaaggagaagaacttttcac | 30 |
| pBT1694 | US | 106 | ctcgagtaatcaccctcttccaaatc | 31 |
|  | DS | 66 | ttaccaccgataccaccaatgaccatgattacgccaagcttg | 32 |
| pBT1729 | US | 106 | ctcgagtaatcaccctcttccaaatc | 33 |
|  | DS | 83 | acgctttatggaggtgaatttatgaccatgattacgccaagc | 34 |
| pBT1701 | US | 106 | ctcgagtaatcaccctcttccaaatc | 35 |
|  | DS | 94 | tcaaatggattaaaccccgatgaatctttatcagctagtgcatttgac cctaatatgaccatgattacgccaagcttgc | 36 |

TABLE 1a-continued

Polymerase Chain Reaction Primers.

| Fusion | * | Primer 1 | DNA Sequence | SEQ. ID. NO. |
|---|---|---|---|---|
| pBT1720 | US | 106 | ctcgagtaatcaccctcttccaaatc | 37 |
|  | DS | 92 | atgcttgtaggacctacattaccaccgataccaatgaccatgattacgccaagcttgc | 38 |
| pBT1747 | US | 110 | ctcgagattagaacgtaaccaatttag | 39 |
|  | DS | 67 | accttcccggttcttcccccaatgaccatgattacgccaagcttg | 40 |
| pBT1746 | US | 106 | ctcgagtaatcaccctcttccaaatc | 41 |
|  | DS | 142 | acgctttatggaggtgaatttatgaaacagaatgacaaattatgg | 42 |

*: DS, downstream primer;
US, upstream primer
US primer 1 corresponds upstream of the respective bclA or bclB promoter regions with associated XhoI sites. US primer 2 corresponds to the end of the promoter or sequences in the NTD with an overlapping extension matching DS primer 1.
DS primer 1 corresponds with the 5p region of reporter genes (or NTDs fused to reporter genes for pBT1746, pBT1758).
DS primer 2 corresponds to the 3p region of reporter genes with associated XhoI sites.
pBT1746 was constructed by PCR amplification of construct pBT1747 (DS primers) followed by SOE to the bclA promoter region (US primers).
pBT1758 was constructed by PCR amplification of the pBT1693 construct with (DS primers) followed by SOE to the PCR product of the amplification of the US primers.

TABLE 1b

Polymerase Chain Reaction Primers.

| Fusion | * | Primer 2 | DNA Sequence | SEQ. ID. NO. |
|---|---|---|---|---|
| pBT1744 | US | 178 | cctcgcccttgctcaccattggtggtatcggtggtaa | 43 |
|  | DS | 157 | gcctcgagttacttgtacagctcgtccatgc | 44 |
| pBT1742 | US | 159 | cctcgcccttgctcaccatagcaactttttcaataataatgg | 45 |
|  | DS | 157 | gcctcgagttacttgtacagctcgtccatgc | 46 |
| pBT1750 | US | 214 | gattagggtcaaatgccataaattcacctccata | 47 |
|  | DS | 157 | gcctcgagttacttgtacagctcgtccatgc | 48 |
| pBT1758 | US | 244 | catcgctgcggcagccttgtacagctcgtccatgcc | 49 |
|  | DS | 103 | ctcgagttatttgtagagctcatccatgcc | 50 |
| pBT1693 | US | 100 | ttctcctttactcattggtggtatcggtggtaatgtaggtcc | 51 |
|  | DS | 103 | ctcgagttatttgtagagctcatccatgcc | 52 |
| pBT1694 | US | 101 | tggcgtaatcatggtcattggtggtatcggtggtaatgtagg | 53 |
|  | DS | 104 | ctcgagtaaaggaacagatggtggcgtccctcg | 54 |
| pBT1729 | US | 90 | caagcttggcgtaatcatggtcataaattcacctccataaagcgttc | 55 |
|  | DS | 104 | ctcgagtaaaggaacagatggtggcgtccctcg | 56 |
| pBT1701 | US | 95 | gctgataaagattcatcggggtttaatccatttgaataattattatttgacataaattcacctccataaagcg | 57 |
|  | DS | 104 | ctcgagtaaaggaacagatggtggcgtccctcg | 58 |
| pBT1720 | US | 85 | tggtatcggtggtaatgtaggtcctacaagcataaattcacctccataaagcg | 59 |
|  | DS | 104 | ctcgagtaaaggaacagatggtggcgtccctcg | 60 |
| pBT1747 | US | 108 | tggcgtaatcatggtcattggggaagaaccgggaagg | 61 |
|  | DS | 104 | ctcgagtaaaggaacagatggtggcgtccctcg | 62 |
| pBT1746 | US | 143 | cataatttgtcattctgtttcataaattcacctccataaagcgt | 63 |
|  | DS | 104 | ctcgagtaaaggaacagatggtggcgtccctcg | 64 |

*Same footnote as Table 1a.

Spore Analysis by Flow Cytometry

Ten miligrams of spores were resuspended in 500 µl of 4% paraformaldehyde in PBS and incubated for 2 hours at room temperature. The spores were then washed four times with PBS and resuspended in StartingBlock (Pierce) and incubated with mixing at room temperature for 45 minutes. The spores were then pelleted and resuspended in Starting-Block. Rabbit polyclonal antiserum (1:250 dilution) against rBclA was then added and incubated with mixing at room temperature for 45 minutes. The spores were then washed three times in StartingBlock PBS and then incubated with mixing with FITC-Protein A conjugate (Sigma Chemical Co.) and incubated for 45 minutes at room temperature. The spores were then washed three times with StartingBlock, followed by two washes with PBS and then processed on a FACScan flow cytometer using a 488 nm argon laser (Beckton Dickinson Biosciences). Data were analyzed using Cell Quest analysis software (Beckton Dickinson).

Micrograph Images

Samples from sporulating cells on nutrient agar plates or in modified G broth were collected at indicated intervals and diluted in 10 μl of PBS containing DABCO (Diazabicyclooctane, Acros Organics) anti-fade reagent. All images were obtained using a Nikon E600 epi-fluorscence microscope using a 60× or 100× oil immersion objective.

Transmission Electron Microscopy

Immunogold labelling of embedded spores was performed after fixation of spores in a 2% glutaraldehyde and 2% formaldehyde PBS solution. Spores were embedded in 3% agar (EM Science, Gibbstown, N.J.). Dehydration involved sequential treatment with 25%, 50%, 75%, 95% and 100% acetone. Polymerization was carried out at 60° C. in Epon/araldite resin. Sections were cut at 85 nm thickness and put on 200-mesh carbon-coated copper grids; the cut grid sections were blocked in a 1% BSA solution for 30 min. The grids were washed three times in PBS, and the primary antibodies were added to the grids at a concentration of 1:25 in incubation buffer (Aurion). One hour later, the grids were washed six times in incubation buffer and incubated with 1:25 goat antirabbit secondary conjugated with 10 or 20 nm colloidal gold beads and allowed to bind for 2 hours. After a series of washes in PBS, the grids were post-fixed in 2% glutaraldehyde on 0.1 M PBS for 5 min and finished with washes in PBS and distilled water. Samples were examined with a JEOL 1200EX electron microscope.

Example 1

The BclA Protein Contains an N-Terminal Exosporium Targeting Domain

Given that the BclA protein associates with the exosporium via its N-terminus, this N-terminal conserved sequence, SEQ ID NO: 11 (see FIG. 2A), was investigated for the possible targeting of BclA and other collagen-like proteins to the exosporium.

To determine if the N-terminal domain of BclA is sufficient to target the native protein to the exosporium, two gene fusions were generated to the eGFP fluorescent reporter. PCR amplification of the upstream promoter/regulatory sequences of bclA and including the N-terminus coding sequence through the conserved motif or the entire bclA coding sequence was performed. These PCR products were then spliced with the eGFP reporter gene to produce in-frame fusions (FIG. 2B). The DNA constructs were subcloned into the pMK4 shuttle plasmid using known techniques (see Sullivan et al., 1984) and introduced into the plasmid-free ΔSterne strain of B. anthracis by electroporation. Transformants were either induced to sporulate in synchronized modified G Broth or grown in brain-heart infusion broth overnight and induced to sporulate by culturing on nutrient agar plates at 30° C. for 3 days. Expression of the reporters was examined by epi-fluorescence microscopy.

The transformed cells containing the BclA ORF fusion (pBT1742) or N-terminal domain (NTD) fusion (pBT1744) did not express the eGFP reporters during exponential growth (FIG. 3A), which is consistent with the known expression pattern shown by gene array analysis (see Bergman et al., 2006). As the cells expressing the fusions transitioned into stationary phase with the concomitant physiological shift to the sporulation process, fluorescence appeared throughout the mother cell cytoplasm (FIG. 3B). Two hours into stationary phase ($T_2$), BclA is expressed and translated, before a visible spore is formed in the mother cell (FIGS. 3B and 3G). The developing spore surface does not appear to be initially enriched for this reporter fusion protein during the early phases of visible spore development, with the emergent spore evident as a darkened area in the sporulating cell and with no enhanced fluorescence around the spore periphery (FIG. 3B). Synthesis of the fusion protein thus appears to be temporally distinct from incorporation into the exosporium. One hour later ($T_3$), a small amount of enhanced fluorescence became evident at one pole of the spore periphery (FIG. 3C). The initial polar localization of the BclA fusion was oriented towards the mother cell compartment, away from the pole of the mother cell, which is consistent with reports that the exosporium is initiated at this point (Ohye and Murrell, 1973; Steichen et al., 2007). As stationary phase progresses into the fourth hour ($T_4$), this area of fusion protein incorporation at one pole expands around the pole (FIG. 3D). At $T_6$, the exosporium is formed making its way around the spore (FIG. 3E), which was accompanied by a corresponding decrease in cytoplasmic fluorescence, presumably marking the incorporation of the fusion constructs into the exosporium (FIG. 3E). Shortly thereafter, at $T_7$, the incorporation of the fusion into the exosporium was complete. The cytoplasm of the mother cell lost its fluorescence while the surface of the spore retained fluorescence (FIG. 3K). This loss of cytoplasmic fluorescence presumably resulted from deposition of the protein on the spore surface, leakage of the fusion protein from the cell, degradation of the fusion protein or a combination of these events. Examination of the spores at 10 hours into stationary phase ($T_{10}$) revealed the presence of released, highly fluorescent spores (FIG. 3L). A representative growth curve is presented in FIG. 3O. $T_0$ denotes the point of entry into stationary phase.

For comparison, the BclA N-terminal domain fusion (pBT1744) was compared with a second constructed fusion consisting of the entire bclA open reading frame fused to the eGFP reporter gene (pBT1742, FIG. 2B). This fusion encoded by pBT1742 localized and attached to the spore surface at identical time points and distribution as the BclA N-terminal fusion encoded by pBT1744 (FIGS. 4A-4J). This result suggests that the N-terminal domain alone is sufficient for localization and incorporation of the BclA protein onto the spore surface.

Example 2

N-Terminal Amino Acids Required for Exosporium Incorporation

BclA released from spores lack its N-terminal 19 amino acids (Sylvestre et al., 2002; Steichen et al., 2003). It is unknown whether the proteolytic event resulting in the loss of these N-terminal residues takes place during exosporium assembly and BclA incorporation, or occurs after BclA has been stably inserted into the exosporium layer. To determine whether these initial N-terminal amino acids are required for efficient incorporation into the exosporium, a third fusion (pBT1750) was constructed, containing the bclA promoter region, RBS, through the bclA initiation codon followed by the coding sequence for amino acids 20-35 of BclA fused to the eGFP coding sequence (see FIG. 2B). This construct mimics the spore-extracted form of BclA (differing only by the presence of the N-terminal methionine residue), and allows for examination of the role of the truncated N-terminus in incorporation of BclA (FIG. 4K-4O). The pBT1750-expressing cells mirrored the pBT1742 and pBT1744 fusion cultures in their pattern of fluorescence incorporation and timing, suggesting that the initial 19 amino acids are not necessary for localization of BclA into the exosporium.

Figure 4P:
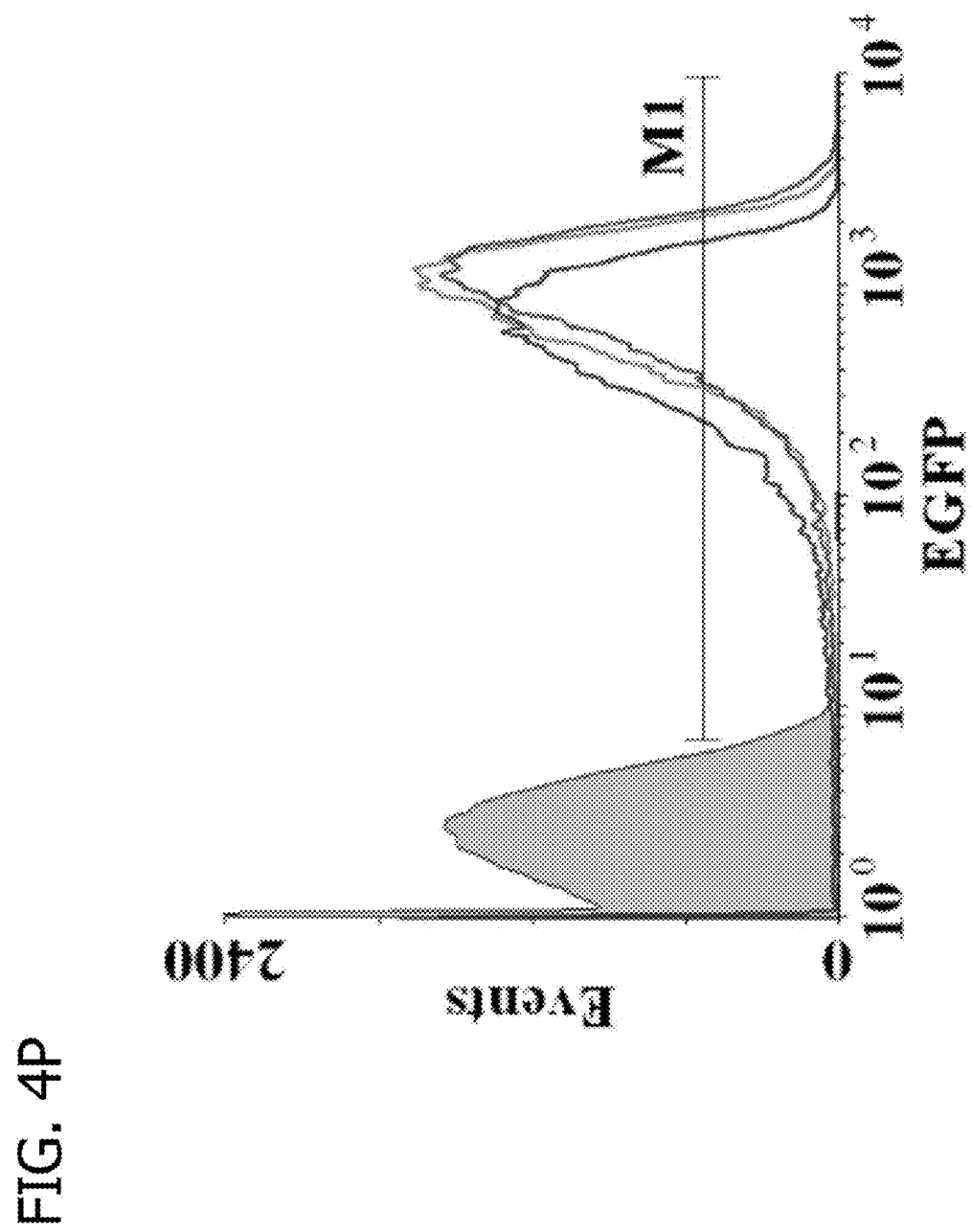
FIGS. 4A-4O show micrographs of sporulating cells and spores from strains expressing the entire BclA open reading frame (ORF) (pBT1742), the N-terminal domain (pBT1744), and the N-terminal truncation (pBT1750) fusion constructs (600× magnification). Ro of the bclA promoter.

To quantify the relative fusion incorporation levels, a direct comparison of the fluorescence associated with each spore type was undertaken by flow cytometry. All three fusions, (spores containing pBT1744, pBT1742, and pBT1750 fusions) localized to the spore surface to similar degrees (FIG. 4P). Greater than 97% of the spores for all three fusions were positive for fluorescence (Table 2). The mean positive fluorescence (MPF) for the purified, paraformaldehyde-fixed spores was 767 for pBT1744, 817 for pBT1742, and 528 for pBT1750. These data suggest that the N-terminal domain of BclA is not only sufficient, but as efficient as the intact BclA protein in targeting the reporter protein to the spore surface and its stable incorporation of the protein onto the spore. The loss of the N-terminal 19 amino acids did not greatly affect the incorporation of BclA, as only a modest decrease in the amount of fluorescence was seen in the pBT1750-containing spores.

TABLE 2

Fluorescence of Spores Determined by Flow Cytometry

| Designation | % Positive Spores Over Background | PMF | PMF Fold Increase |
| --- | --- | --- | --- |
| ΔSterne pMK4 | 5.5 | 7.42 | 1.0 |
| pBT1742 | 89.5 | 140.9 | 19.0 |
| pBT1744 | 99 | 307.9 | 41.5 |
| pBT1693 | 98.3 | 59.69 | 8.0 |
| ΔSterne pMK4 | 3.9 | 5.5 | 1.0 |
| pBT1694 | 96.6 | 94.6 | 17.2 |
| pBT1729 | 3.8 | 5.7 | 1.0 |
| pBT1701 | 73.2 | 15.2 | 2.8 |
| pBT1720 | 11.4 | 6 | 1.1 |
| pBT1747 | 4.2 | 5.9 | 1.1 |
| pBT1746 | 72.5 | 16 | 2.9 |

Example 3

Figure 5A:
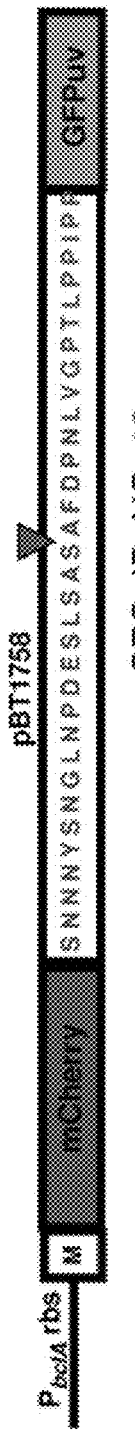

Cleavage of the N-Terminal Domain Associates with Incorporation of BclA into the Exosporium The attachment of the pBT1750-encoded fusion implied that the truncated BclA can be recognized and attached to the exosporium. To address the question of whether cleavage of the intact BclA N-terminal domain occurs during exosporium formation, a dual reporter fusion construct was made. The pBT1758-encoded fusion consists of the bclA promoter followed by the mCherry monomeric reporter gene (Shaner et al., 2005; Giepmans et al., 2006) fused in frame to the BclA N-terminal domain that was in turn fused in frame to the GFPuv reporter (FIG. 5A). This fusion allows for the analysis of cleavage in the N-terminal domain (NTD) by appearance of separation between the red fluorescence and green fluorescence of the reporter proteins.

Figure 5B:
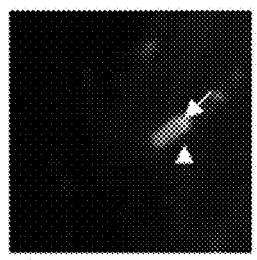
Figure 5C:
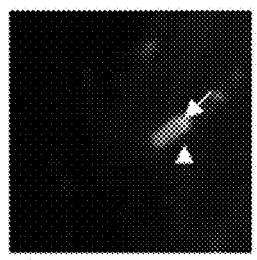
Figure 5D:
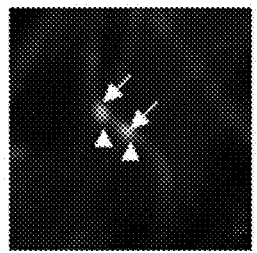
Figure 5E:
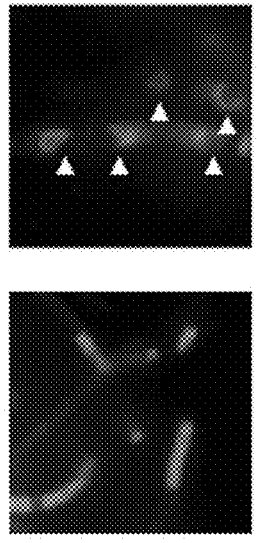

Similar to the findings with the single-reporter fusions, the pBT1758 fusion appeared in the mother cell cytoplasm prior to the appearance of the emerging spore (FIGS. 5B and 5H). The orange fluorescence (rather than yellow) likely resulted from a more intense red fluorescence of the mCherry fusion relative to monomers of the green GFPuv reporter protein in this fusion (Shaner et al., 2005). Soon thereafter, the fusion localized to the spore periphery, as demonstrated by the orange rings, localizing around the pole of the emerging spore (FIGS. 5C and 5I). At subsequent time points, the developing orange fluorescence continued to envelop the spore, followed by the putative cleavage event. This cleavage event results in the release of bound mCherry and subsequent emergence of a green spore (FIGS. 5D, 5E, 5J and 5K). The reduction in the local concentration of mCherry, combined with the enrichment of GFPuv fluorescence at the spore periphery resulted in production of yellow fluorescence (FIGS. 5D, 5E, 5J and 5K). Progression of cleavage around the spore surface released increasing concentrations of the mCherry reporter with the NTD 19-amino-acid tail attached to its C-terminus into the mother cell cytoplasm. However, the GFPuv reporter, by virtue of its attachment to the C-terminus of BclA amino acids 20-35, became stably attached to the spore surface (FIGS. 5E and 5F). Completion of the cleavage events (yellow fluorescence reaching the distal pole of the spore) coincided with the definitive appearance of the spore in the bright field images (FIGS. 5E and 5K). The cleavage events trailed the positioning of BclA at the exosporium (as demonstrated in FIGS. 3A-3O) from the mid-mother cell-facing pole of the spore to its completion at the opposite pole (FIGS. 5E and 5K). Fluorescence of the released mCherry reporter quickly faded, as the cleaved mCherry fusion protein appeared either to be unstable inside the mother cell, or was rapidly lost from the cytoplasm during initial stages of mother cell lysis (FIGS. 5F and 5L). The released spores retained their incorporated green fluorescence (FIGS. 5G and 5M).

The systematic cleavage of the reporter fusions at the site of the exosporium assembly demonstrated the difference in timing between the positioning of the BclA protein at the exosporium and the cleavage event. No discernable red or orange fluorescence was observed in the released spores, demonstrating a correlation of the cleavage event with the final incorporation of BclA into the exosporium. Therefore, the loss of the N-terminal residues of BclA results from events related to exosporium synthesis and not subsequent release of BclA.

Example 4

Reporter Oligomerization is not Required for Exosporium Incorporation

The interwinding of the individual native BclA molecules to form a triple helix in wild-type spores is made possible by interactions among the C-terminal domains of the BclA monomers (Boydston et al., 2005). The ability of pBT1744 and pBT1750 fusions, lacking both the C-terminal domain of BclA and the collagen-like region (CLR) with its associated glycosylation sites (Daubenspeck et al., 2004), to localize to the exosporium suggests that neither oligomerization of proteins nor glycosylation of the CLR are essential for incorporation of proteins into the exosporium of B. anthracis. Although not essential, oligomerization of proteins may be beneficial in localization to the exosporium. Two additional constructs were made that contained the BclA protein sequence from pBT1744, but fused to the GFPuv reporter (pBT1693) or DsRed (pBT1694, FIG. 2B). The GFPuv reporter has a natural propensity to dimerize under physiological conditions, and the DsRed reporter protein obligately tetramerizes (Yang et al., 1996; Baird et al., 2000). The pBT1693 and pBT1694 constructs (FIGS. 6A-6J) displayed expression kinetics and fluorescent distribution profiles similar to the eGFP fusions (FIGS. 3A-3O and 4A-4P). In all cases, fluorescence appeared initially after sporulation had commenced followed by an increased concentration of the fluorescent reporter around the spore periphery (FIGS. 6A-6C, 6F-6H). The complete loss of cytoplasmic fluorescence in the pBT1694-containing sporulating cells prior to spore release may signify a more complete incorporation of the fusion proteins into the exosporium. A delay in the spore release of the pBT1694-encoded fusion cells was observed. The DsRed self-association of this tetramerizing protein (Baird et al., 2000) may form a tight shell around the spores and mask structures or interfere with natural processes that trigger spore release from the mother cells. After lysis of the mother cells, released spores retained surface-associated fluorescence (FIGS. 6D, 6E, 6I, and 6J).

To eliminate the possibility that the reporter proteins bind non-specifically to the exosporium, a control fusion was constructed. DsRed was expressed under the control of the bclA promoter and ribosome binding site (RBS) but without any of the bclA N-terminal coding sequence (pBT1729; FIG. 2B). Although containing identical promoter and RBS elements as the aforementioned constructs, the pBT1729-containing cells exhibited diminished fluorescence in the cytoplasm, suggesting that the DsRed protein without the N-terminal BclA sequence had a substantially shorter half-life in the sporulating cells. A similar observation was made with the mCherry reporter (a derivative of DsRed) of the pBT1758 fusion (FIGS. 5A-5M). However, the DsRed in the pBT1729-containing cells did not concentrate around the periphery of the spore (FIGS. 6K-6M) and the released spores were not fluorescent (FIGS. 6N and 6O). Thus, the labelling of the spores by the reporter fusions appeared not to be the result of non-specific binding of the reporter proteins to the spore surface.

Example 5

Contributions of the Conserved Motif and N-Terminal Sequences to Exosporium Incorporation of Reporter Proteins To determine if the conserved motif sequence identified in FIG. 2A was required for attachment of the fusion proteins to the spore surface, fusion constructs were created that either contained the BclA N-terminal sequence lacking the conserved sequence (SEQ ID NO: 11; pBT1701), or contained only the conserved motif, SEQ ID NO: 11, fused to DsRed (pBT1720, FIG. 2B). The pBT1701-encoded fusion protein without the conserved motif exhibited a reduced concentration around the spore periphery, no polar localization, and maintained cytoplasmic fluorescence up to the time of spore release. Only modest levels of fluorescence were detected on released spores (FIGS. 6P-6T). Thus loss of the conserved N-terminal BclA sequence resulted in a diminished exosporium incorporation of the fusion protein.

The pBT1720-encoded fusion protein, consisting of the conserved motif alone fused to DsRed, but lacking the rest of the BclA initial N-terminal residues (residues 2-24, which includes the proteolytic cleavage site), concentrated around the spore periphery quickly after being expressed with a corresponding decrease in cytoplasmic fluorescence. However, released spores were devoid of fluorescence (FIGS. 6U-6Y). Thus the presence of only the conserved motif resulted in the fusion protein being targeted to the spore periphery, but was insufficient to allow attachment of the protein to the mature exosporium. It was observed that localization of the motif-only fusion followed the normal progression of NTD localization oberved with the pBT1744-encoded fusion (mother cell proximal pole to the mother cell distal pole), but stable incorporation failed to occur and the fusion was lost from the spores (FIGS. 6U-6W). The BclA N-terminal 24 amino acids missing in this fusion protein contain the site for the proteolytic cleavage event that may be involved in the attachment of BclA to the exosporium. Optimal localization and attachment of BclA to the maturing exosporium is dependent upon the conserved motif, whereas the ultimate attachment of BclA requires the N-terminal cleavage event.

Figure 7:
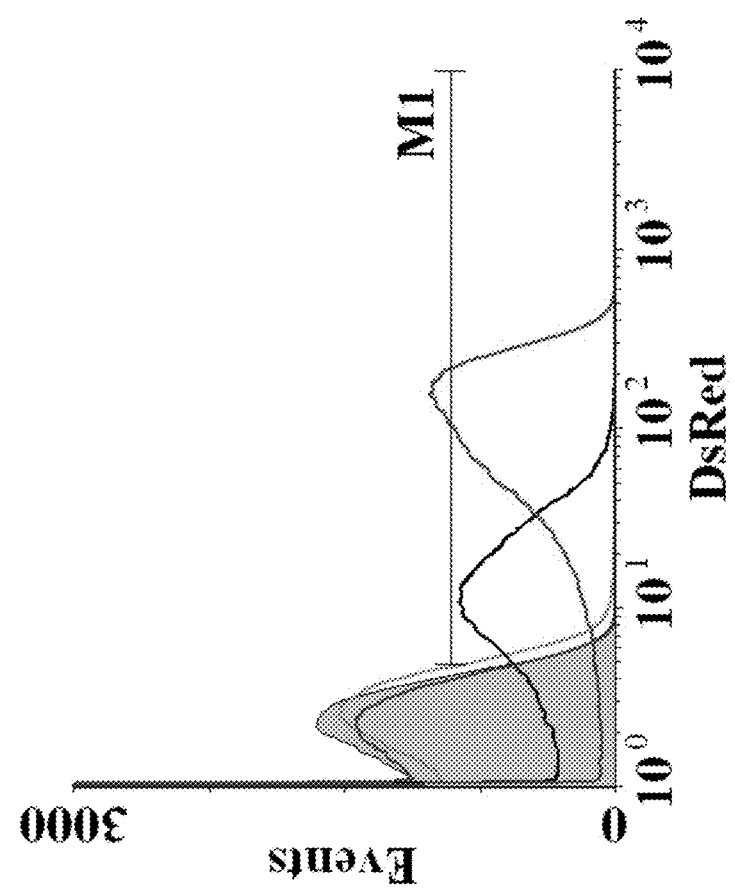

To quantify the level of incorporation of each of the DsRed-containing fusion constructs into the released spores, flow cytometry was performed on purified, paraformaldehyde-fixed spores (FIG. 7 and Table 2). The DsRed fluorescence of the spores bearing the intact BclA N terminal 35 amino acid sequence (pBT1694) was 6.2-fold greater than all other DsRed-containing fusion constructs (FIG. 7). The fusion lacking the conserved motif (pBT1701) was detectably fluorescent, with greater than 73.2% of the spores positive over background and with a mean positive fluorescence (MPF) of 15.2. But these values were substantially lower than those obtained with pBT1694-bearing spores (96.6%, MPF 94.6%). The pBT1720 conserved motif-only fusion gave little detectable fluorescence above that of the negative control spores (11.4% to 3.9%, MPF 6). Spores from cells expressing DsRed without BclA N-terminal residues (pBT1729) were not detectably fluorescent over background (3.8% vs. 3.9%).

Example 6

Exosporium Incorporation Utilizing the BclB N-Terminal Domain

After establishing that the BclA N-terminal domain was sufficient to localize proteins to the spore periphery, the ability of the corresponding BclB domain to target proteins to the exosporium was studied. The DsRed reporter was fused to the BclB N-terminus with the coding sequence up to and including the conserved region, with the natural bclB promoter and RBS (pBT1747; FIG. 2B). Previous reports have suggested that bclB and bclA are transcribed at an identical stage in sporulation, but with bclB transcribed at a –2-fold lower level (Bergman et al., 2006). However, the pBT1747-encoded fusion appeared earlier in the sporulation process than the BclA fusions and at a greatly reduced level, lower than the reported 2-fold difference in mRNA (Bergman et al., 2006). Released spores only contained barely detectable levels of the fusion protein (FIG. 8G).

To increase production of the BclB fusion proteins, the BclB N-terminal sequence fused to DsRed was positioned under the control of the more active bclA promoter and RBS elements (pBT1746; FIG. 2B). The pBT1746-encoded fusion protein was expressed at a level similar to that of the pBT1694 construct. The pBT1746-encoded BclA construct mimicked the pBT1694-encoded BclA construct, with both fluorescent fusions produced and localizing around the spore periphery before release of the fluorescent spores (FIGS. 8A-8F). There appeared to be a difference in the spore localization pattern on the pBT1746-encoded fusion, with the fluorescence spread across the spore in a slightly mottled fashion and ultimately encompassed only 75% of the spore, with one pole devoid of fluorescence (FIGS. 8E and 8F). The fusion did not exhibit the more uniform distribution seen with the pBT1693- and pBT1694-encoded fusions. Although incorporation was evident, the capacity of the BclB domain to target proteins to the spore surface was reduced when compared to that of the BclA N-terminal fusion (FIG. 8G). The pBT1746-encode BclB fusion spores were 72.5% positive compared with 96.6% for pBT1694-containing spores, with a MPF of 16.1 compared to 94.6. This result illustrates that the presence of the BclB N-terminus is sufficient to localize foreign proteins to the spore surface, but the degree of incorporation is dependent upon the production level of the protein and/or the differences in the sequences of the N-terminus or targeting domains of BclA and BclB.

Example 7

Native BclA is Incorporated into Spores Expressing Reporter Proteins

To determine if native BclA continued to be incorporated into the exosporium in cells expressing the Bcl-domain-containing fusions, fluorescent purified spores were incubated with rabbit anti-recombinant BclA polyclonal antibodies followed by FITC-Protein A conjugate (FIGS. 9A-9F). Spores from each of the DsRed fusion constructs retained the ability to bind anti-BclA antibodies, indicating that native BclA was incorporated into the spores. Spores from the promoter-only constructs (pBT1720 and pBT1729) produced spores with wild-type levels of BclA as expected (FIGS. 9D, 9E). Spores with the fusion protein incorporated into the exosporium demonstrated a pronounced heterogeneity in the amount of fusion protein on the spore surfaces relative to the native BclA levels in individual spores in the population (FIG. 9A-9F). This result was especially noticeable in the pBT1746-encoded (BclB NTD) fusion, suggesting that the incorporation of the fusion hinders native BclA incorporation or may effect the topology of the proteins, thus inhibiting binding or access of the anti-BclA polyclonal antibodies to the native BclA.

Example 8

Incorporation of Fusion Proteins onto the Exosporium Surface

Exosporium targeting was checked by immune-electron microscopy analysis of spores containing the pBT1744-encoded BclA N-terminal fusion to eGFP. Spores were analysed under TEM after treatment with either anti-rBclA rabbit polyclonal antibodies or anti-GFP rabbit polyclonal antibodies (Imgenex). These primary antibodies were followed with secondary gold-labelled anti-rabbit antibodies bearing 20 and 10 nm gold particles, respectively (FIGS. 9G and 9H). Both anti-GFP and anti-rBclA antibodies localized to the nap layer of the exosporium. The anti-GFP antibodies were found in closer proximity to the basal layer, which may be due to the eGFP protein lacking the filamentous structure associated with native BclA. There was no indication that the incorporation of the fusion proteins differed from the incorporation of natural BclA. The appearance of the exosporium was normal, despite the incorporation of the fusion proteins.

Example 9

The BAS3290 Protein can be Used to Introduce Foreign Antigens

Figure 11B:
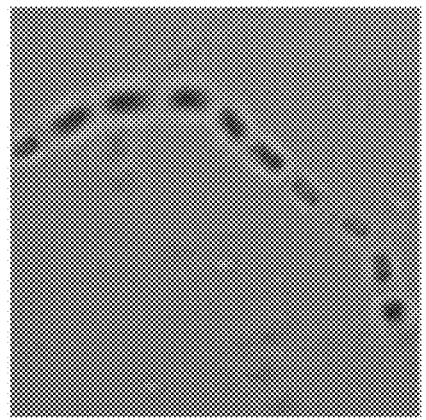
FIGS. 11A-11D show micrographs of a fusion of the entire BAS3290 ORF to the EGFP reporter under the control of the native BAS3290 $\sigma^K$
Figure 11D:
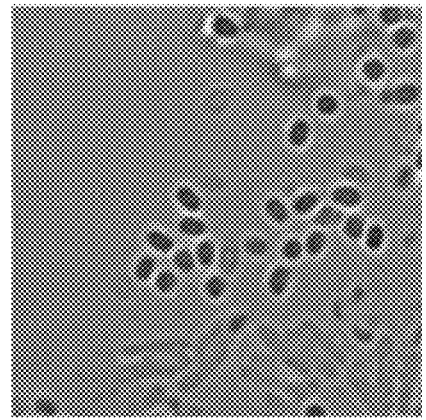
Figure 11A:
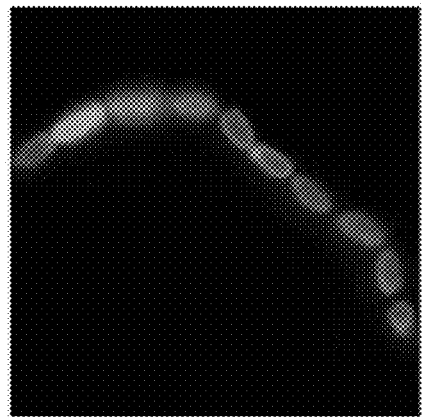
Figure 11C:
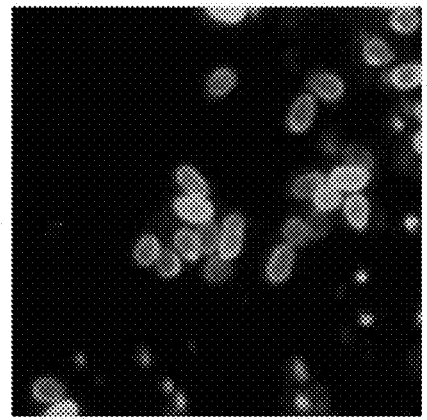

The BAS3290 protein of *B. anthracis* is predicted to localize to the exosporium due to the high degree of identity of its N-terminal domain (SEQ ID NO: 8) to the N-terminal domain of the localization domain of the BclA protein (SEQ ID NO: 7; 13 of 14 amino acid residues identical). A fusion of the entire BAS3290 ORF to the EGFP reporter under the control of the native BAS3290 $\sigma^K$ was constructed. This fusion protein was produced late in the sporulation process, which was consistent with transcription under this promoter. This fusion protein was produced and localized immediately to the exosporium (FIGS. 11A and 11B). After localization to the exosporium, this fusion was affixed to the released spores demonstrating as fluorescent spores (FIGS. 11C and 11D). This result demonstrates that the BAS3290 protein acts mechanistically similar to the BclA protein, and could also be utilized for the creation of fusion for surface display of foreign antigens on the exosporium of *B. anthracis*.

Example 10

Other Exosporium Containing-*Bacillus* Species

To demonstrate the conserved nature of the localization machinery in the *Bacillus cereus* family, the pBT1744 construct (*B. anthracis* BclA N-terminal domain fused to EGFP; see Thompson et al. 2008) was utilized. This pBT1744 construct was electroporated into *B. cereus* strain 14579 and *B. thuringiensis* strain kurstaki. Proper antibiotic resistant clones were allowed to enter sporulation, and observed upon release of free spores. The *B. anthracis* BclA N-terminal domain localized and attached to the spores of both *B. cereus* (FIG. 12A) and *B. thuringiensis* (FIG. 12B). This result demonstrates that any of the *Bacillus cereus* family may be used to incorporate foreign antigens onto exosporia of the family.

Example 11

*Bacillus* Exosporium Molecule Delivery (BEMD) Systems

Figure 13C:
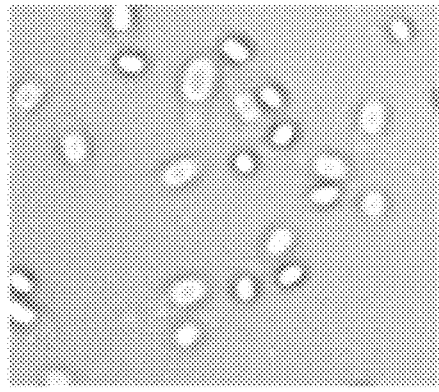
FIGS. 13A-13F show the *B. anthracis* spores expressing the BclA (FIG. 13B) and BclB (FIG. 13C) NTD tagged Porcine Respiratory and Reproductive Virus (PRRSV) ORF5 labeled with preimmune or immune sera from pigs.
Figure 13F:
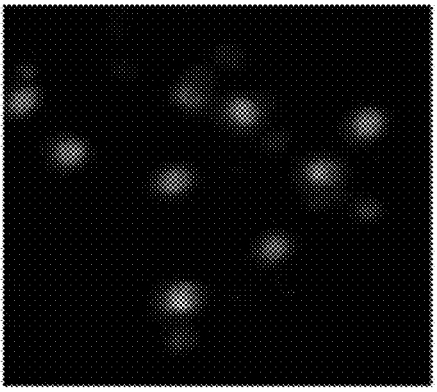
Figure 13B:
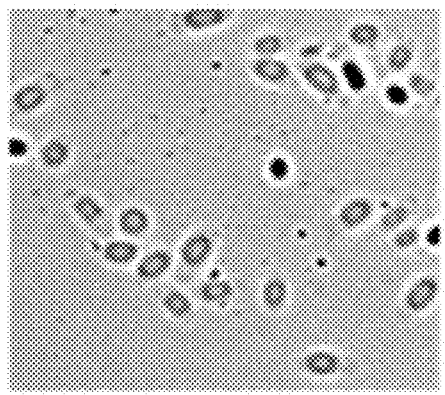
Figure 13E:
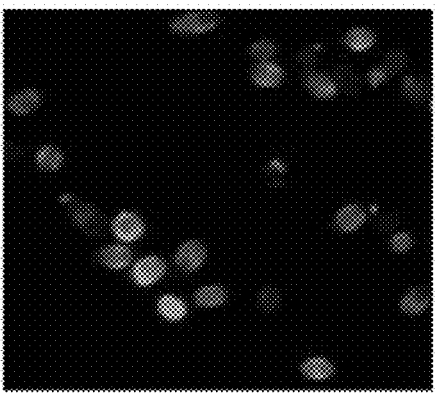
Figure 13A:
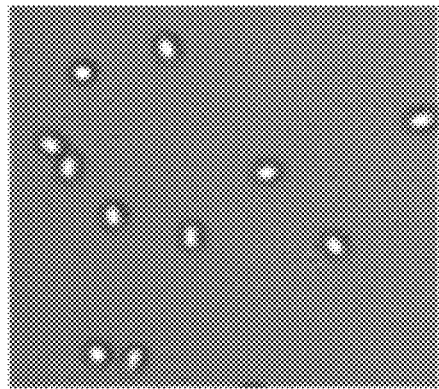
Figure 13D:
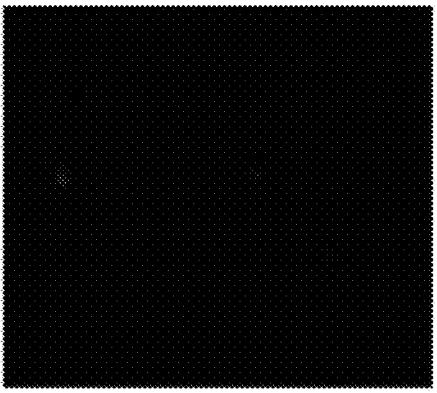

The ORF5 from the Porcine Respiratory and Reproductive Virus (PRRSV), which encodes a protective, neutralizing protein, was chosen to be an exemplary foreign antigen expressed using the BEMD system in different *Bacillus cereus* family members. Polymerase chain reaction (PCR) of the PRRSV ORF5 was accomplished using standard techniques. Fusion of the PRRSV ORF5 to the N-terminal domain of BclA or BclB was accomplished by splicing and overlapping extension techniques well-known in the art. Correct fusions were cloned into the shuttle plasmid pMK4, sequenced, and electroporated into *B. anthracis* strain ΔSterne and *B. thuringiensis* strain kurstaki. Correct transformants were selected, grown in Brain Heart Infusion broth and then allowed to sporulate by plating onto N agar plates at 30° C. Free spores were collected after 3 days, and washed with PBS to remove vegetative cell debris. Purified spores were then subjected to immunolabeling with sera from either preimmune pigs, or from pigs previously infected with PRRSV and to whom a known titer to PRRSV had been established. Exposure to sera was followed with protein A-FITC conjugate, which binds to all antibodies and lights up green. As shown in FIGS. 13A-13F, the *B. anthracis* spores expressing either the BclA or the BclB N-terminal domain (NTD) tagged PRRSV ORF5 labeled with immune sera (FIGS. 13B, 13C), while immune sera did not react with wildtype spores (FIG. 13A).

Figure 14B:
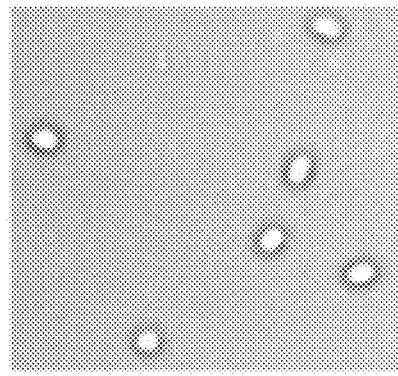
FIGS. 14A-14D show the *B. thuringiensis* spores expressing the BclA NTD tagged PRRSV ORF5 labeled with immune sera (FIG. 14A) or preimmune sera (FIG. 14B) from pigs.
Figure 14D:
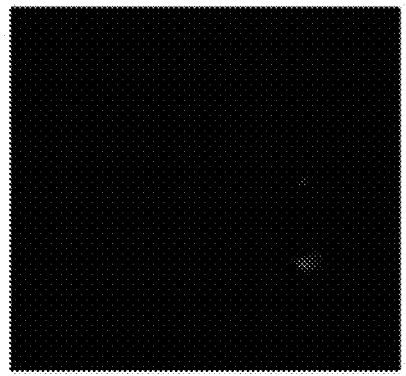
Figure 14A:
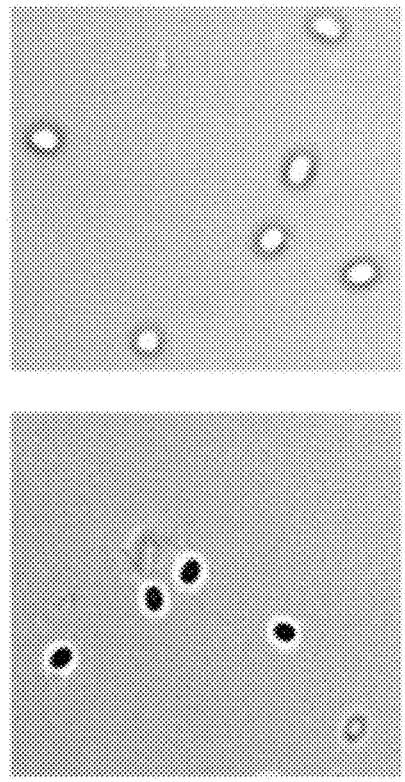
Figure 14C:
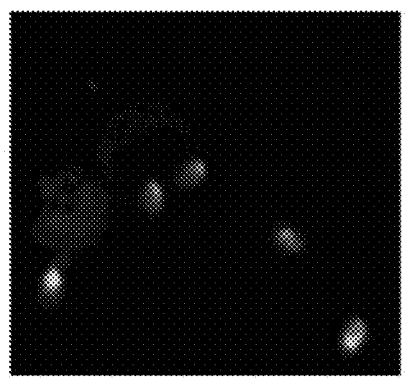

In *B. thuringiensis*, the BclA NTD tagged PRRSV ORF5 localized to the exosporium, but mostly preferentially to one pole (FIG. 14A). These spores did not react with the preimmune pig sera, suggesting the reactivity seen at the poles was specific to PRRSV (FIG. 14B). These results demonstrate that foreign antigens can be expressed on the surface of the exosporium of the B. cereus family members with this antigen expression system, and that reactivity to these proteins is demonstrated by immunofluorescence assays. This reactivity indicates that the foreign antigens have surface exposure and are available to stimulate an immune reaction.

Figure 15:
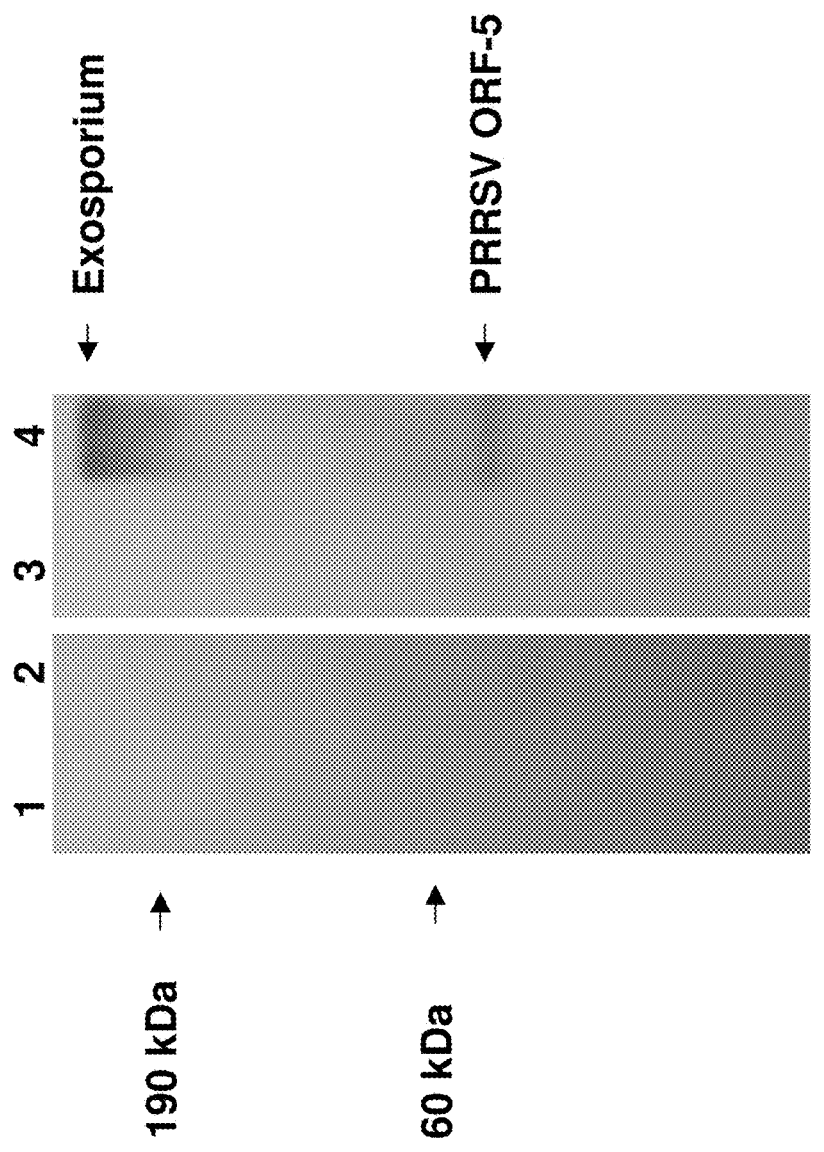

Next, extraction of the spore layers from the B. thuringiensis spore expressing the PRRSV ORF5 protein fused to the BclA protein was undertaken. Separation of these extracted proteins by SDS-PAGE, followed by western blotting with immune and preimmune pig sera (FIG. 15) further demonstrates the specific reactivity of the immune sera to the PRRSV ORF5 (see Lane 4 on the gel). The high molecular weight material on the western is indicative of large molecular weight exosporium complexes which do not dissociate under SDS or urea buffer insult. Glycosylation of these complexes leads to the variable molecular weight smear seen on the blot (Lane 4). The lower molecular weight band (Lane 4) corresponds to the molecular weight of the fusion of PRRSV ORF5 fused to BclA NTD.

Example 12

Expressing Bioactive Enzymes Using the BEMD System

The use of this genetic system for expressing enzymes on the surface of the spore bioparticles is a promising approach to mitigation of contaminates in both soil and water. To demonstrate the effectiveness of this approach the common test enzyme β-galactosidase was expressed on the surface of BEMD bioparticles. β-galactosidase (β-gal) converts the disaccharide lactose into monosaccharides, galactose and glucose (β-gal use reviewed in Rosochacki et al. 2002). This enzyme is commonly used in genetic screening as a hallmark of enzyme activity. β-galactosidase, isolated from the lacZ gene from E. coli, was cloned in frame with the promoter elements, RBS, and first 35 amino acids of the bclA gene of B. thuringiensis. The resulting construct was cloned into the Gram positive shuttle vector pMK4, sequenced for verification, and electroporated into B. thuringiensis as previously described (Thompson and Stewart, 2008). Correct clones were allowed to undergo sporulation in Tiger broth overnight, and free spores were collected and purified via differential centrifugation (Thompson et al. 2011). The spores expressing β-gal were then UV-inactivated to finish the construction of the "killed spore" β-gal bioparticles.

Figure 16:
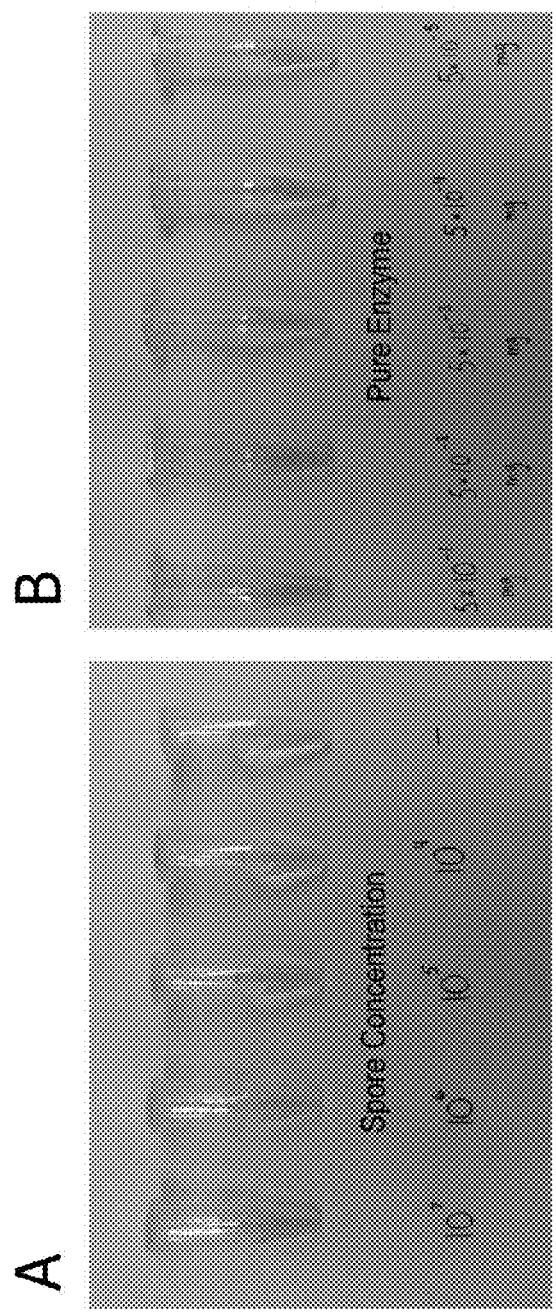
FIG. 16 shows the remediation capability of the BEMD system expressing β-gal enzyme as an MOI. Specifically, a depiction of 1 ml serial dilutions of β-gal enzyme as the MOI in a BEMD system (A) or pure β-gal enzyme in 1 mm o-nitrophenyl-β-galactoside (ONPG) (B) was analyzed over the course of 5 minutes at room temperature. Activity was assayed at 425 nm for the release of o-nitrophenyl from ONPG.

For the initial testing of the β-gal bioparticles, free β-gal enzyme concentrations (Thermo Pierce) were used in comparison to allow for the assessment of total enzyme activity on a single bioparticle. Activity was determined via action of β-gal on the chromogenic substrate o-nitrophenyl-β-galactoside (ONPG) which releases the yellow chromogen o-nitrophenyl (ONP) in response to β-gal enzyme activity. Serial dilutions of bioparticles and the generation of a standard curve allowed for the calculation of active enzyme expressed per bioparticle, which yielded >$2 \times 10^7$ active β-gal enzymes per bioparticle (FIG. 16).

Example 13

Remediation of Contaminants in a Liquid Medium Using the BEMD System

Figure 17:
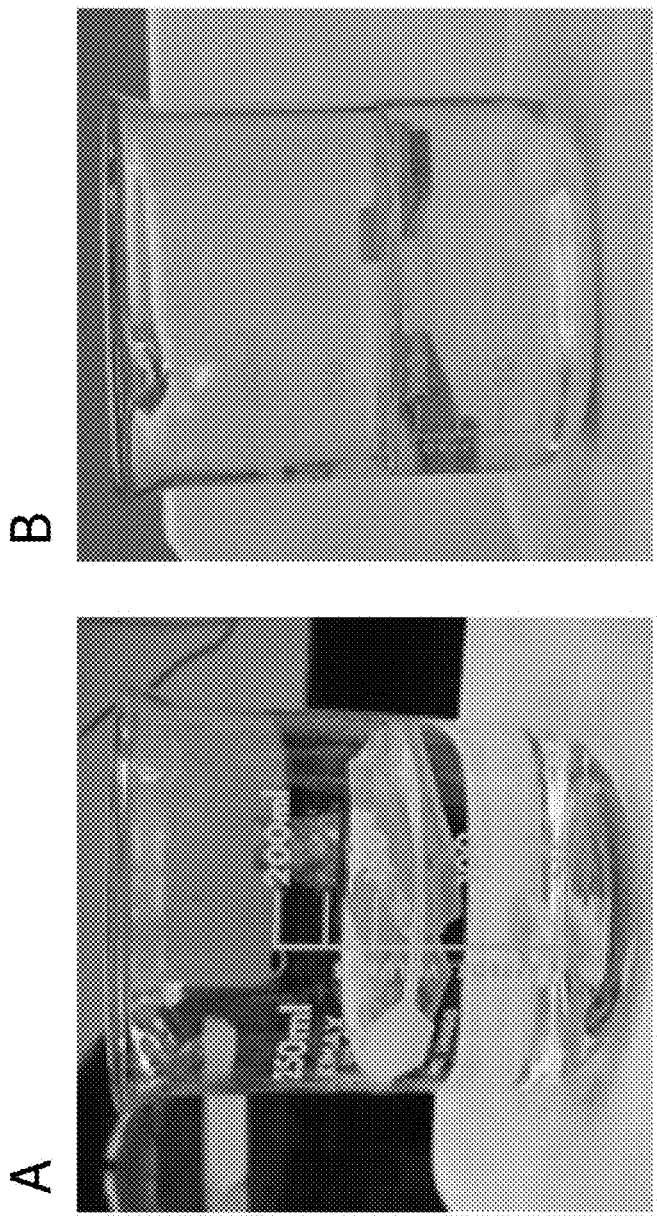
FIG. 17 shows a demonstration of the enzymatic activity of a β-gal expressing BEMD system on 1 mM ONPG substrate in water. The β-gal expressing BEMD system is contained within the dialysis membrane between the two orange dialysis clips at the surface of the solution. Panel A of FIG. 17 shows the demonstration at time 0 hours (h) and panel B of FIG. 17 shows the demonstration at time 12 h. The appearance of yellow color ONP is indicative of the enzymatic reaction of β-gal on colorless ONPG.

One of the potential applications for BEMD bioparticle system includes the remediation of contaminated water sources. To demonstrate the potential effectiveness of BEMD bioparticles in water remediation, a small scale demonstration using β-gal bioparticles to "remediate" a 150 ml solution of 1 mM "ONPG contaminated" $dH_2O$ was created (FIG. 17). $1 \times 10^6$ β-gal bioparticles were contained within a dialysis membrane to allow for the free flow of aqueous solutions but the retention the bioparticles. At room temperature, within 2 hours all of the available ONPG substrate was converted into ONP, demonstrating the robust potential for these bioparticles in the remediation of larger bodies of water (FIG. 17). A further increase in reaction temperature would increase the overall reaction speed, but does represent the likely conditions of contaminated water sources in the environment.

Example 14

Remediation of Contaminants in a Flowing Liquid Medium Using the BEMD System

Figure 18:
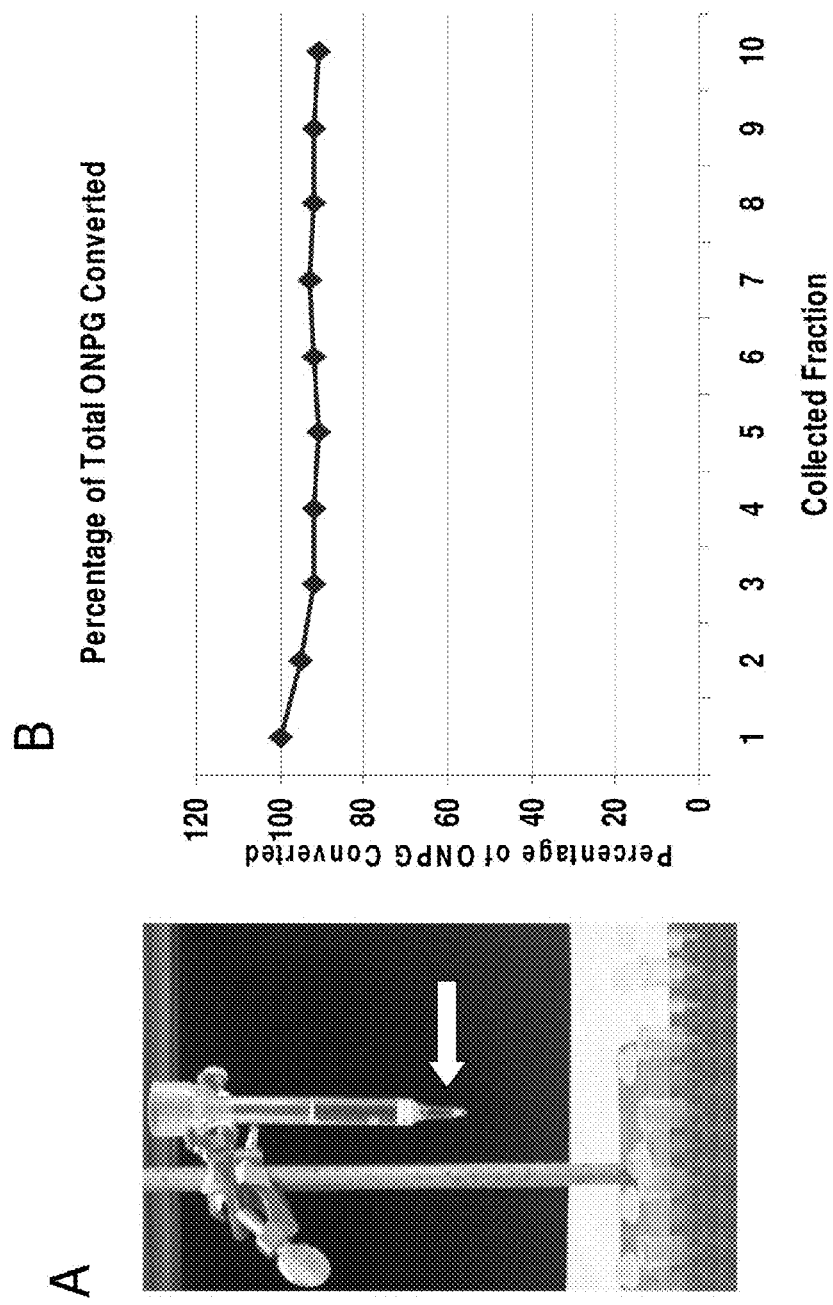
FIG. 18 shows a gravity flow column and the resultant activity of a β-gal expressing BEMD system. The BEMD system particles between the frets are marked by an arrow (A). The flow rate was 1 ml per 30 seconds (s). The results for the conversion of ONPG to OPG over ten fractions was collected (B).

Contaminated water sources are not limited to larger bodies of water such as wells and lakes. The remediation of flowing contaminated water sources (such as runoff or stream waters) is of great concern. To demonstrate the use of bioparticles in this application, a gravity flow column to assay their ability to provide enzyme hydrolysis within a flowing system was created (FIG. 18). $1 \times 10^6$ β-gal bioparticles were contained between two column frets, which allowed for the free flow of solution while containing the bioparticles within the column. In this system, we were able to "bioconvert" >90% of the available ONPG within the 30 seconds it took the solution to pass through the bioparticle compartment (FIG. 18). Higher efficiencies (>99%) can be obtained by either decreased the flow rate or increasing the concentration (10 fold) of bioparticles within the compartment.

Example 15

Remediation of Contaminants in Solid Medium Using the BEMD System

Figure 19:
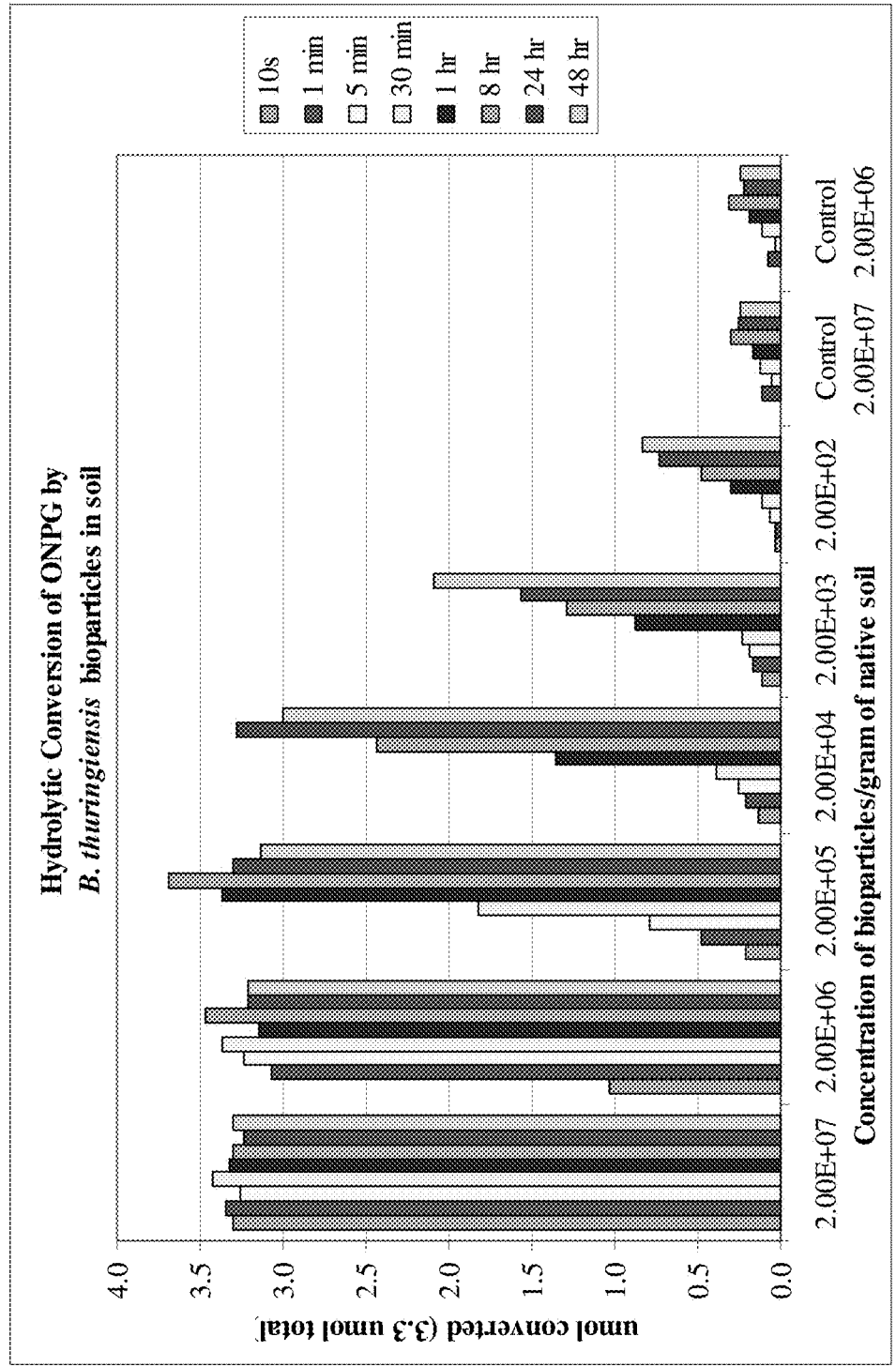
FIG. 19 shows the activity of various concentrations of β-gal expressing BEMD particles in native soil slurries over time. The maximum conversion of ONPG detectable was 3.3 μmol/10 μl cleared slurry in this assay. Controls consisted of bioparticles that do not express β-gal. Activity observed in the controls is due to low levels of naturally occurring β-gal enzymes found in native soil bacteria present in the samples. Background absorbance of cleared soil slurries alone without ONPG was subtracted from overall absorbance levels.
Figure 20A:
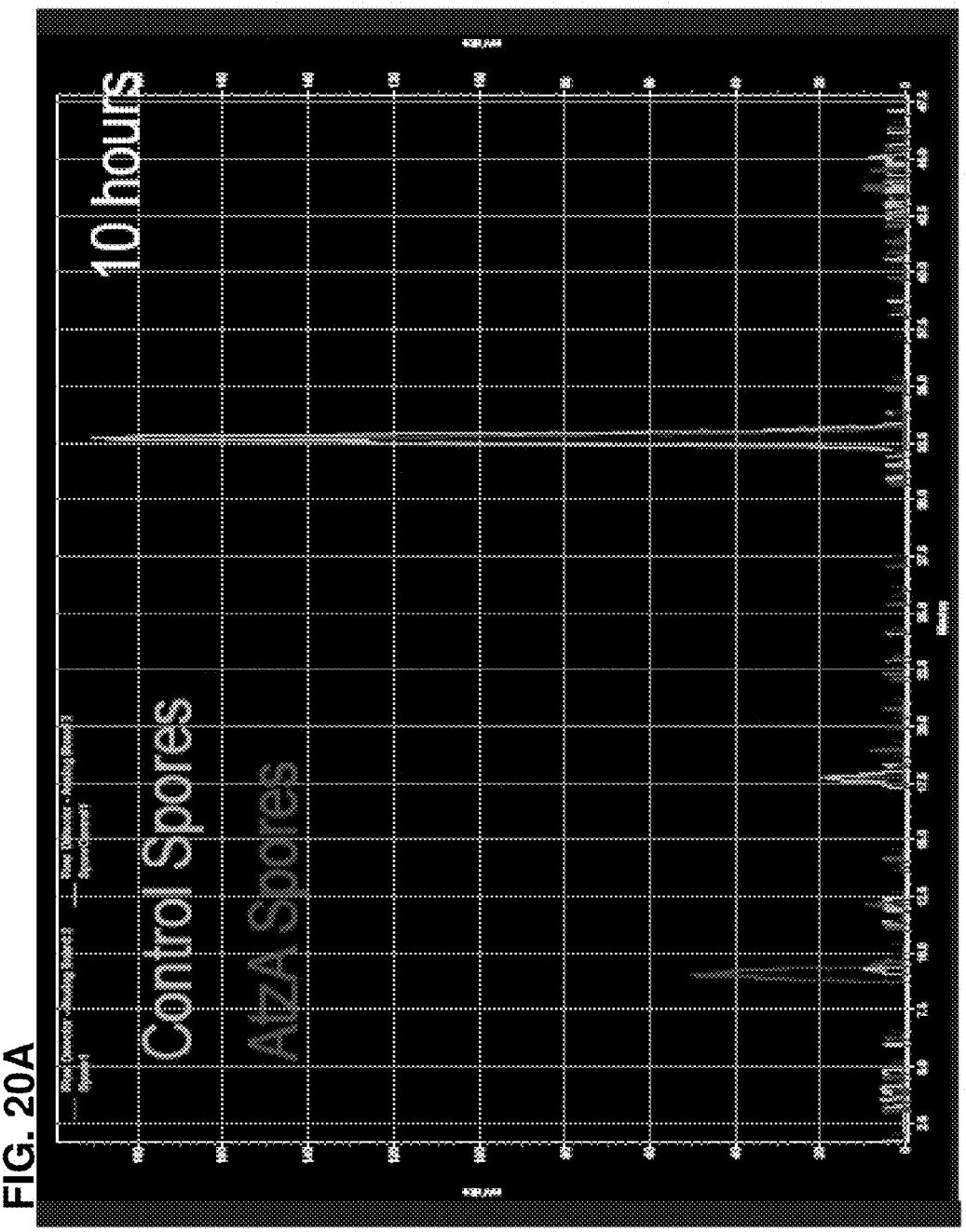
FIGS. 20A-20E show the conversion of atrazine to hydroxyatrazine using AtzA expressing BEMD system particles. AtzA expressing BEMD system particles were incubated with atrazine and analyzed by HPLC for conversion of atrazine to the benign hydroxyatrazine at specific time points.
Figure 20B:
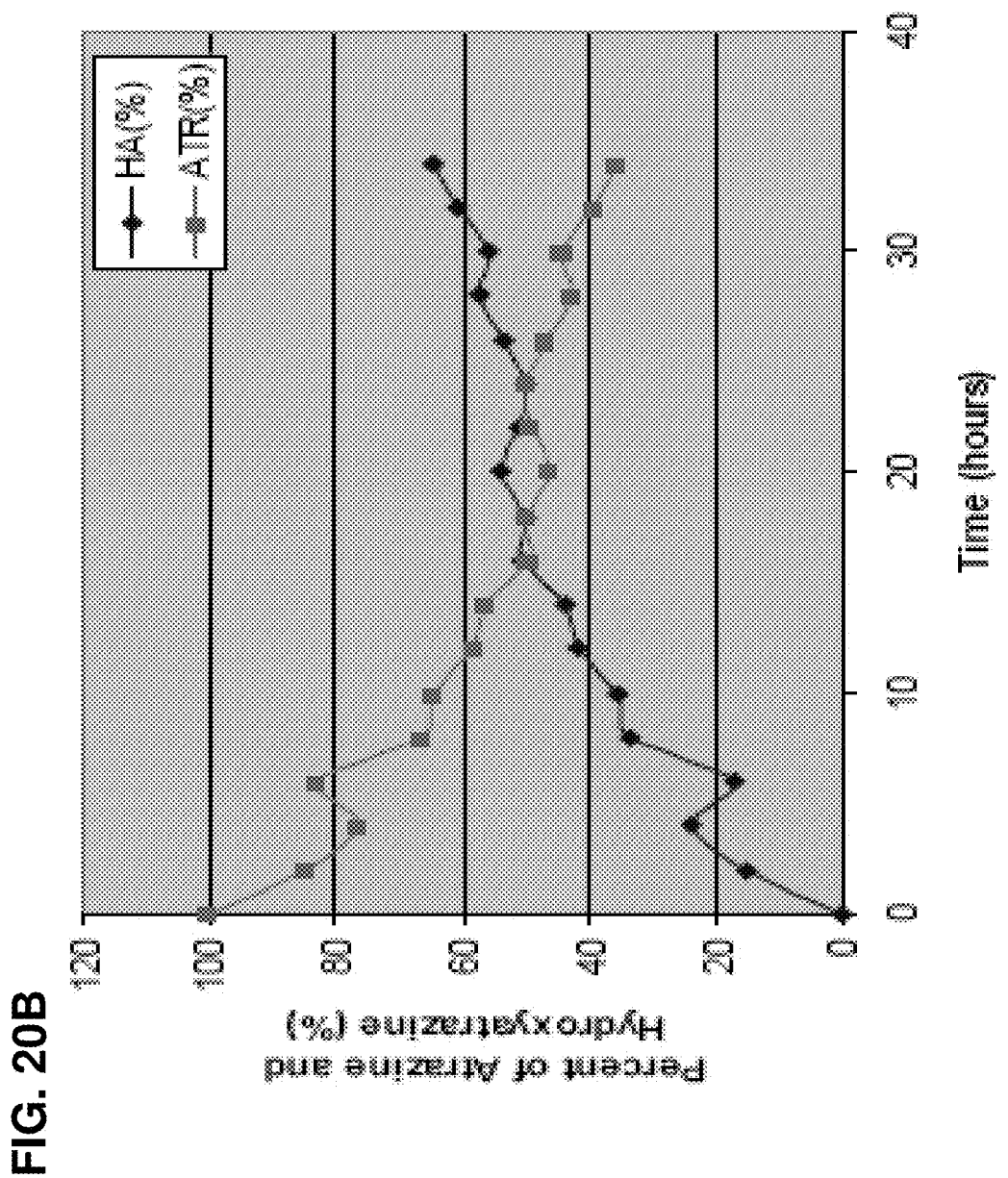
Figure 20C:
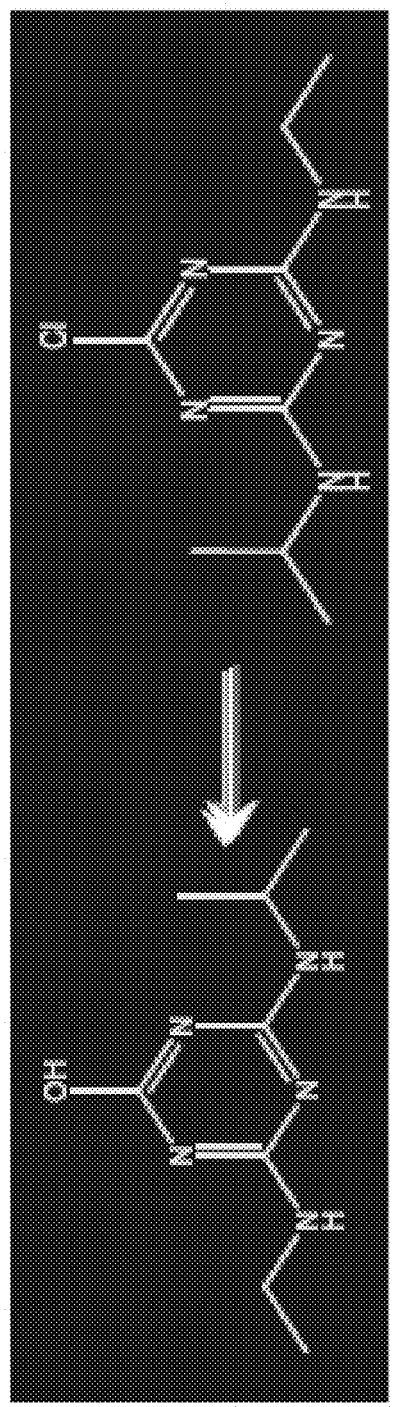
Figure 20D:
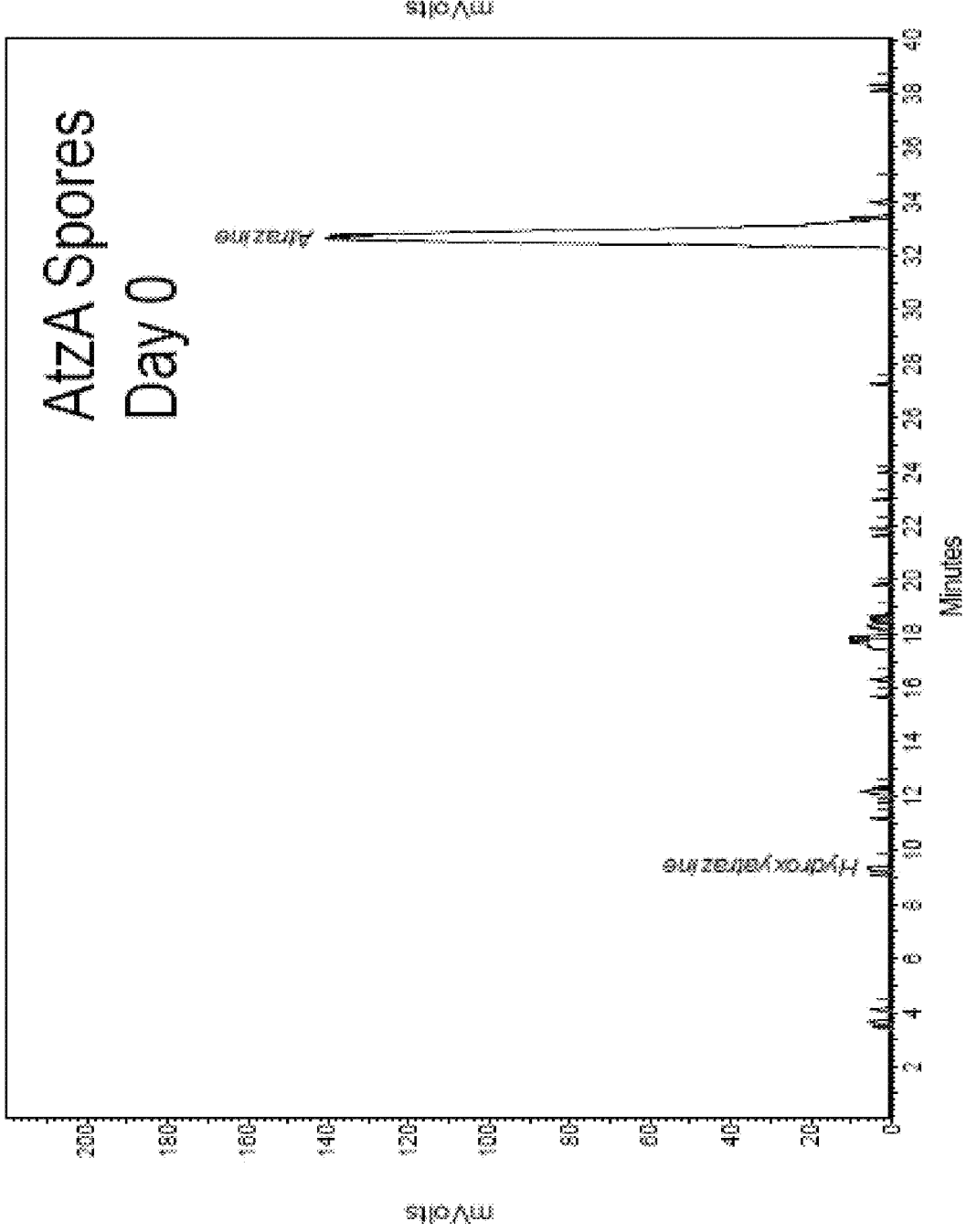
Figure 20E:
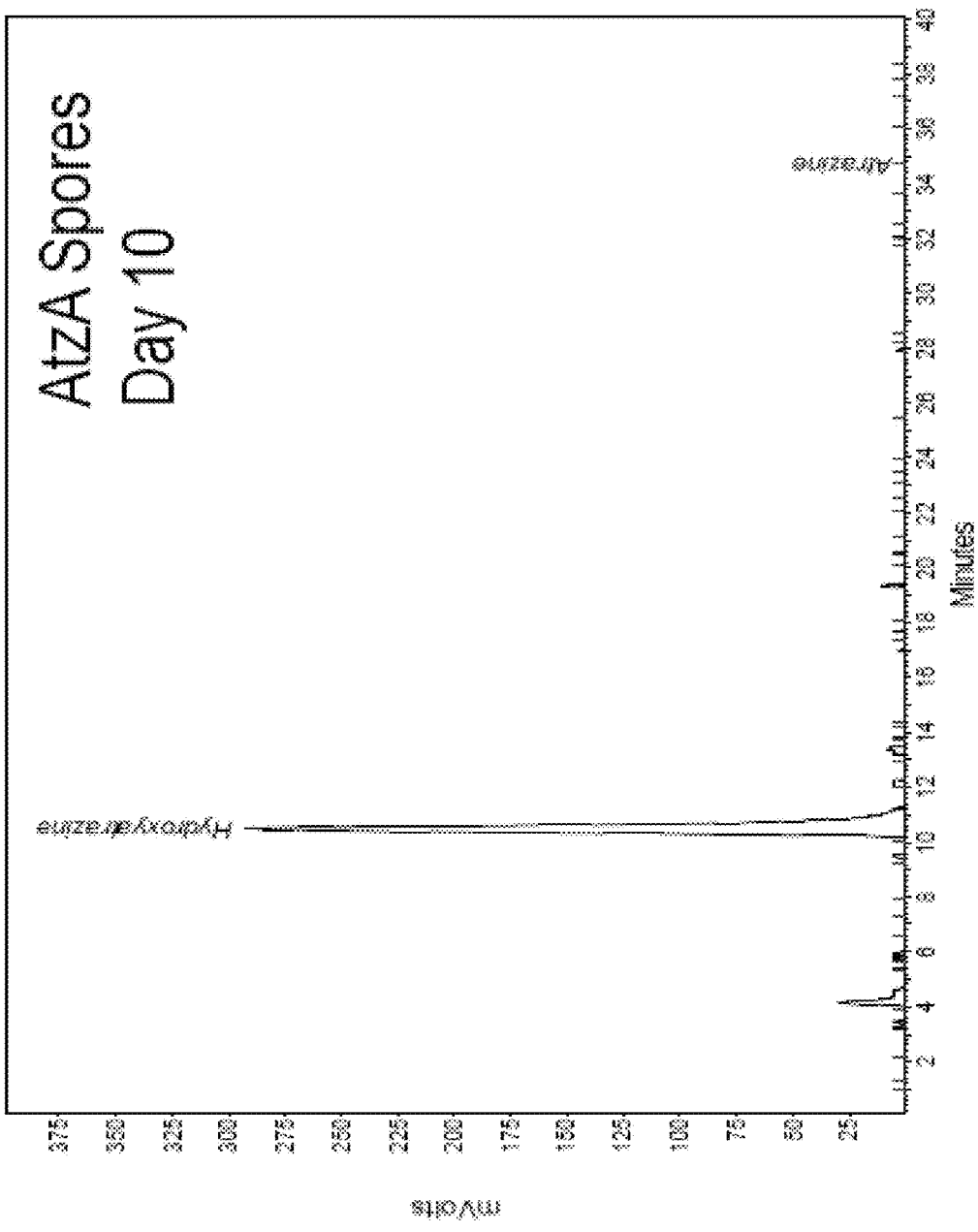

An important application for the bioparticles is in the efficient bioconversion of contaminates in soil. The efficient removal of contaminates from soil sources requires that the enzymes be delivered into the soil and remain active in situ. To demonstrate the potential for soil remediation with the β-gal bioparticles, various concentrations of β-gal bioparticles were placed into 1 g of native soil, and the solution was agitated into a slurry with the addition of 500 ml of 1 mM ONPG in $dH_2O$ (FIG. 19). Enzyme activity in soil was measured over time from 2 seconds to 48 hours at room temperature after removal of soil and bioparticles from slurry via centrifugation. Addition of higher concentrations of β-gal bioparticles into soil led to the efficient conversion of all substrate in as little as 10 seconds. Efficient bioremediation occurred in the presence of as little as 200 β-gal bioparticles/gram soil (FIG. 19). As bioremediation techniques generally operate over the course of months, it is not necessary to utilize the higher concentrations of bioparticles. The tillage of contaminated soil with the addition of slurry concentrations of as little as $1 \times 10^3$ β-gal bioparticles per gram (only 1×10$^6$ per Kg soil) would allow for extremely low cost of production during contaminate remediation.

Example 16

Remediation of Mercury Contamination Using the BEMD System

The toxicity of mercuric compounds, specifically organic mercuric compounds and inorganic mercuric compounds, has been well established (reviewed in Counter et al., 2004; Grandjean et al. 2010). Of the various forms of mercury, organic methylmercury is the most toxic form. Organic mercury is the result of a covalent linkage between the mercury ion and an organic radical. Organic mercury compounds, such as methylmercury (MeHg$_2$) and ethylmercury, are a natural byproduct of aqueous anaerobic bacteria's action on inorganic mercury compounds (Ullrich et al. 2001). Methylmercury compounds work bioaccumulate to concentrated levels in predatory fish and large predators who primarily feed on fish. Ingestion of predatory fish is the most common exposure route of MeHg$_2$ for humans (Hightower and Moore, 2003). Organic mercury compounds are readily absorbed by the body but poorly excreted. This buildup of organic mercuric compounds leads to alterations in the immune and nervous systems, as well as affecting genetic and enzymatic systems of the body (Hightower and Moore, 2003). Methylmercury is of even greater concern in embryonic development, where the developing embryos and children are 5-10 times more susceptible to organic mercury sources (Counter et al. 2004). Nearly 60,000 children are born at risk each year from in utero exposure to methylmercury ingested by the mothers (National Research Council, 2000). Statewide advisories against eating mercury contaminated fish exist throughout the Great Lakes area and Northwestern U.S. With the significant and widespread threat of organic mercury compounds, mercury is rated number 3 of the top concerns by the CERCLA list of hazardous substances and is an ideal target for bioconversion and bioremediation efforts.

Other sources of organic mercury exposures include past contaminations of food via dumping of industrial waste in Niigata, Japan and the mass exposure of citizens of Iraq to food sources sprayed inadvertently with methylmercury-based fungicide in the 1960s and 1970s (Baker et al. 1973, Myers et al. 2004). Mercury compounds, both organic and inorganic are released into the environment upon industrial processes such as alkali and metal processing, incineration of coal, medical and other waste, and the mining of mercury and gold. Exposure to inorganic mercury (Hg$^2$+) or mercuric salts (such as HgCl$_2$) are rare but can lead to gastrointestinal problems and kidney failure. Upon entry into the environment, inorganic mercury is quickly converted through action of natural bacteria into various forms, including the toxic methylmercury and the least toxic form, volatile elemental mercury (Hg$^0$ Osborn et al., 1997). Elemental mercuric vapor is globally distributed into the atmosphere via a mercury cycle, where it can interact with ozone and water to form mercuric ions (Hg$^{2+}$, Munthe and McElroy, 1992). Chronic long term exposure to high levels of elemental mercury vapor can lead to tremors, gingivitis, and long term excitability (Counter et al., 2004).

As methylmercury is toxic to bacteria in the environment, many soil and water species of bacteria have evolved mechanisms to control their internal methylmercury levels. Hundreds of isolated soil bacteria contain two mercuric reductase genes, MerA and MerB (Osborn et al., 1997). The MerA mercuric reductase enzymatically converts methylmercury and related organic mercury compounds into inorganic mercury (Silver and Phung, 1996). Inorganic mercury compounds are then further catalyzed into elemental mercury vapor via the action of the mercuric reductase MerB (Silver and Phung, 1996). With the combined activities of both enzymes, toxic methylmercuric compounds are converted into elemental mercuric vapor. This elemental mercuric vapor, if released slowly over time, is an ideal circumstance for removing more toxic mercuric compounds from solutions. The production of elemental mercury vapor is a natural process, and the over half of elemental vapor in the environment is from natural sources such as volcanoes and geysers (Pacyna et al. 2006). The majority of the remainder of the mercury in the atmosphere comes from stationary combustion, generally from coal-fired power plants (Pacyna et al. 2006).

The contamination of the environment with methylmercury compounds has been a problem to date. Current methods to remove mercury include the adsorption of mercury compounds with ion-exchange resins or bioabsorbents, but have issues with conditions found in the environment (Ritter and Bibbler, 1992; Chang and Hong, 1994). Passive use of bacteria as a bioadsorbent has promise, but leads to large volume of hazardous mercury-laden biomass which is both problematic and expensive to dispose of.

Use of MerA/B enzymes to remediate mercury in the environment is promising, but no record of their use in this purpose has been shown to date. The promise of the MerA/B enzymes has been demonstrated by the creation of glass microcosmos supplemented with mercury-reducing bacteria to simulate the natural environment. A 95% conversion of Hg$^{2+}$ to Hg$^0$ can be obtained over time with merAB containing bacteria in these microcosms (Saouter et al. 1994). Genetically engineered *E. coli* have been developed that overexpress MerA, but have not been tested in the environment (Chen and Wilson, 1997). Additionally, MerA has successfully been expressed in both yeast and plants (Rensing et al. 1992, Rugh et al. 1996).

To construct specific enzymatic systems utilizing the BEMD bioparticle system for the bioremediation of organic mercury and inorganic mercury genes, the MerA and MerB enzymes will be amplified and cloned as described in the previous Examples. The enzymes will be cloned into the p20EXGram positive shuttle vectors which contain the bclA promoter elements, RBS, start codon, and sequence for the initial 35 amino acids of BclA followed by a XhoI restriction enzyme site for site-directed cloning. Placement of the MerA/B ORFs in the p20EX plasmid will be accomplished via PCR with primers flanked by XhoI sites. When cloned in frame in this context the expression of these enzymes will occur during late sporulation only (Thompson and Stewart, 2008). The 35 amino acid BclA "tag" allows for their covalent incorporation into the exosporium layer of the developing *B. thuringiensis* through covalent interaction with the sporulation protein BxpB (Thompson et al. 2011). This plasmid contains 8 additional alanine residues between the BclA "tag" and the cloned enzyme sequence which allows for better retention of native enzyme folding. The 35 amino acid BclA tag does not have any native secondary structure (Rety et al. 2005). Correct clones will be verified via DNA sequencing. Plasmid DNA will be isolated from correct clones and utilized for electroporation into the toxinless *Bacillus thuringiensis* subsp. *israelensis*. Total DNA will be isolated from each *Bacillus* plasmid-containing clone and plasmid DNA transformed into *E. coli* and the resultant plasmids verified via DNA sequencing.

Clones will be grown in BHI broth overnight at 37° C., and placed into our derivatized sporulation broth (Tiger broth) to induce sporulation (Thompson et al. 2011). Tiger broth allows for rapid sporulation and collection of *B. thuringiensis* bioparticles in as little as 16 hours. Spore bioparticles will be collected, purified by differential centrifugation in PBS (Thompson et al. 2007), UV-sterilized, and stored at 4° C. until ready for testing. Alternatively, cells can be plated on nutrient plates at 30° C. for 3 days, the spores swabbed and pooled, and purified and sterilized as above.

*B. thuringiensis* bioparticles expressing MerA or MerB on their exosporium will be delivered to solid surfaces or liquid contaminated with organic or inorganic mercury.

Example 17

Remediation of Hexavalent Chromium (VI) Using the BEMD System

Another heavy metal of great concern in environmental contamination is the presence of hexavalent chromium (VI) resulting from production byproducts from wood, textile, fiber, stainless steel, leather tanning, and anti-corrosive coatings (Kotaś and Stasicka, 2000). Chronic hexavalent chromium exposure leads to the development of many different types of cancer, including lung, kidney, and intestinal variations of cancer due to its high oxidation properties (Katz and Salem, 1992, Barceloux and Barceloux, 1999). The presence of highly contaminated hexavalent chromium sites has led to public outcry and the placement of hexavalent chromium as number 18 on the CERCLA list of hazardous substances. The enzyme ChrR, isolated originally from the soil bacterium *Pseudomonas putida*, is able to convert the toxic hexavalent chromium into the benign chromium (III) (Gonzalez et al. 2005). Chromium (III) is a necessary nutritional component of many organisms and is a common food additive and vitamin supplement found in pharmaceutical concoctions worldwide. Chromium (III) is non-toxic at higher levels due to its poor uptake by cells and ease of removal from the body (Eastman et al. 2008).

Many bacterial species have the ability to reduce hexavalent chromium to Chromium III, but no effective technique has been established for the environmental remediation of hexavalent chromium (Keyhan et al. 2003; Wang, 2000). The greatest barrier for their use for chromium VI remediation is the potent toxicity of chromate to the bacteria (Ackerley et al. 2006). The chromate gives an electron to reactive oxygen species (ROS) and this ROS subject the cells to extreme oxidative stress. The use of the ChrR enzyme BEMD bioparticle alleviates this concern, as the BEMD bioparticles are already inactivated and not subject to the toxic levels of ROS. Additionally, the ChrR enzyme in particular does not produce high levels of chromate, and is an efficient enzyme at converting hexavalent chromium (chromium VI, Cr VI) directly to Chromium III (Gonzalez et al. 2005).

For ChrR bioparticles, we will test for activity of the enzyme-laden bioparticles for their activity on hexavalent chromium VI using a flow injection direct spectrophotometric assay for chromium VI and III speciation (Themelis et al. 2005). This system can accurately detect chromium speciation via the activation of the CrVI-chromotrophic acid complex and reading the absorbance at 370 nm. Briefly, serial dilutions of ChrR bioparticles will be subjected to serial dilutions of hexavalent chromium in solution and assayed to determine a standard curve and overall activity of the ChrR bioparticles. 100 µl samples from each reaction will be collected, mixed with 10 mM chromotrophic acid and 150 mM NaF, and run through the flow injector to determine the concentration of Chromium VI in the solution. The sample is then exposed to 0.1 mM KlO4 and 50 mM NaOH to oxidize the Chromium III to Chromium VI and run through the flow injector a second time to determine total Chromium levels (and therefore the Cr III levels).

Using this ratio, we will obtain the efficiencies of the ChrR bioparticles to bioconvert various concentrations of hexavalent chromium VI.

A preliminary examination of the activity of the bioparticles will be performed in a native soil. 1 g of native soil will be mixed in slurry with 500 ml of ChrR bioparticles and relevant concentrations of Chromium VI. Over time we will collect samples from the cleared slurry and subject them to flow injection or ICP-MS analysis to determine activity in soil.

Example 18

Use of the BEMD System in the Remediation of Atrazine

The BEMD system can be used to degrade atrazine in atrazine contaminated environments. The degradative enzyme AtzA was cloned into the BEMD system as an MOI using the methods described in previous Examples. AtzA BEMD bioparticles were incubated with atrazine. At selected timpoints a sample of the atrazine contaminated environment was analyzed by high phase liquid chromatography (HPLC) for conversion of atrazine to benign hydroxyatrazine (FIGS. 20A-20E). The results indicated that AtzA BEMD bioparticles are efficient at remediation of atrazine contaminated environments.

Example 19

Use of the BEMD System in the Production of Biofuels

BEMD bioparticles expressing enzymes capable of hydrolyzing biomass into sugars will be generated using the methods described in the previous examples. These BEMD bioparticles will be applied to an amount of biomass to be converted to sugars and then fermented to ethanol.

Example 20

Use of the BEMD System in the Decontamination of Surfaces

BEMD bioparticles expressing enzymes capable of converting contaminants to less toxic forms will be generated using the methods described in the previous examples. These BEMD bioparticles will be applied to a contaminated surface and allowed to react with the contaminants.

Example 21

Use of the BEMD System in the Remediation of Fertilizer Products from Soil and Water BEMD bioparticles expressing enzymes capable of converting fertilizer products to less toxic forms will be generated using the methods described in the previous examples.

These BEMD bioparticles will be applied to soil and water contaminated with fertilizer products and allowed to react with the products.

Example 22

Use of the BEMD System in the Production of Biodiesel

BEMD bioparticles expressing enzymes transesterification of methyl- or other short chain esters will be generated using the methods described in the previous examples. These BEMD bioparticles will be applied to vegetable oils and allowed to react to produce biodiesel.

Example 23

Use of the BEMD System in the Degradation of Carcinogens

BEMD bioparticles expressing enzymes capable of degrading carcinogens will be generated using the methods described in the previous examples. These BEMD bioparticles will be applied to carcinogen contaminated environments and allowed to react in order to degrade the carcinogens into a non-carcinogenic form.

Example 24

Use of the BEMD System in the Breakdown of Waste Streams from Agriculture Facilities BEMD bioparticles expressing enzymes capable of degrading contaminants in waste streams from agriculture facilities will be generated using the methods described in the previous examples. These BEMD bioparticles will be applied to the waste streams from agriculture facilities and allowed to react.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference. All patents and publications referred to herein are incorporated by reference.

Baillie, L., Hibbs, S., Tsai, P., Cao, G. L., and Rosen, G. M. (2005) Role of superoxide in the germination of *Bacillus anthracis* endospores. FEMS Microbial. Lett. 245: 33-38.

Baird, G. S., Zacharias, D. A., and Tsien, R. Y. (2000) Biochemistry, mutagenesis, and oligomerization of DsRed, a red fluorescent protein from coral. Proc. Natl. Acad. Sci USA 97: 11984-11989.

Barnes, A. G., Cerovic, V., Hobson, P. S., and Klavinskis, L. S. (2007) *Bacillus subtilis* spores: a novel microparticle adjuvant which can instruct a balanced Th1 and Th2 immune response to specific antigen. Eur. J. Immunol. 37: 1538-1547.

Basu, S., Kang, T. J., Chen, W. H., Fenton, M. J., Baillie, L., Hibbs, S., and Cross, A. S. (2007) Role of *Bacillus anfhracis* spore structures in macrophage cytokine responses. infect Immun. 75: 2351-2358.

Bergman, N. H., Anderson, E. C., Swenson, E. E., Niemeyer, M. M., Miyoshi, A. D., and Hanna, P. C. (2006) Transcriptional profiling of the *Bacillus anthracis* life cycle in vitro and an implied model for regulation of spore formation. J. Bacterial. 188: 6092-6100.

Boydston, J. A., Chen, P., Steichen, C. T., and Turnbough, C. L. Jr. (2005) Orientation within the exosporium and structural stability of the collagen-like glycoprotein BclA of *Bacillus anthracis*. J. Bacteriol. 187: 5310-5317.

Boydston, J. A., Yue, L., Kearney, J. P., and Turnbough, C. L. Jr. (2006) The ExsY protein is required for complete formation of the exosporium of *Bacillus anthracis*. J. Bacterial. 188: 7440-7448.

Brossier, F., Levy, M., and Mock, M. (2002) Anthrax spores make an essential contribution to vaccine efficacy. Infect. Immun. 70: 661-664.

Ciabattini, A., Parigi, R., Isticato, R., Oggioni, M. R., and Pozzi, G. (2004) Oral priming of mice by recombinant spores of *Bacillus subtilis*. Vaccine. 22: 4139-4143.

Chakrabarty, K., Wu, W., Booth, J. L., Duggan, E. S., Coggeshall, K. M., and Metcalf, J. P. (2006) *Bacillus anthracis* spores stimulate cytokine and chemokine innate immune responses in human alveolar macrophages through multiple mitogen-activated protein kinase pathways. Infect Immun. 74: 4430-4438.

Daubenspeck, J. M., Zeng, H., Chen, P., Dong, S., Steichen, C. T., Krishna, N. R., Pritchard, D. G., and Turnbough, C. L. Jr. (2004) Novel oligosaccharide side chains of the collagen-like region of BclA, the major glycoprotein of the *Bacillus anthracis* exosporium. J. Biol. Chem. 279: 30945-30953.

Driks, A. (2002) Maximum shields: the assembly and function of the bacterial spore coat. Trends Microbiol. 10: 251-254.

Due, L. H, Hong, H. A., Atkins, H. S., Flick-Smith, H. C., Durrani, Z., Rijpkema, S., Titball, R. W., and Cutting, S. M. (2007) Immunization against anthrax using *Bacillus subtilis* spores expressing the anthrax protective antigen. Vaccine 25: 346-355.

Due, L. H., Hong, H. A., Fairweather, N., Ricca, E., and Cutting, S. M. (2003) Bacterial spores as vaccine vehicles. Infect. Immun. 71: 2810-2818.

Giorno, R., Bozue, J., Cote, C., Wenzel, T., Moody, K. S., Mallozzi, M., Ryan, M., Wang, R., Zielke, R., Maddock, J. R., Friedlander, A., Welkos, S., and Driks, A. (2007) Morphogenesis of the *Bacillus anthracis* spore. J. Bacterial. 189: 691-705.

Hachisuka, Y., Kojima, K., and Sato, T. (1966) Fine filaments on the outside of the exosporium of *Bacillus anthracis* spores. J. Bacterial. 91: 2382-2384.

Haldenwang, W. G. (1995) The sigma factors of *Bacillus subtilis*. Microbiol. Rev. 59: 1-30.

Henriques, A. O., and Moran, C. P. Jr. (2007) Structure, assembly, and function of the spore surface layers. Ann. Rev. Microbiol. 61: 555-588.

Hilbert, D. W., and Piggot, P. J. (2004) Compartmentalization of gene expression during *Bacillus subtilis* spore formation. Microbial Mol. Biol. Rev. 68: 234-262.

Ho, S. N., Hunt, H. D., Horton, R. M., Pullen, J. K., and Pease, L. R. (1989) Site-directed mutagenesis by overlap extension using the polymerase chain reaction. Gene 77: 51-59.

Horton, R. M., Hunt, H. D., Ho, S. N., Pullen, J. K., and Pease, L. R. (1989) Engineering hybrid genes without the use of restriction enzymes: gene splicing by overlap extension. Gene 77: 61-68.

Isticato, R., Cangiano, G., Tran, H. T., Ciabattini, A., Medaglini, D., Oggioni, M. R., De Felice, M., Pozzi, G., and Ricca, E. (2001) Surface display of recombinant proteins on *Bacillus subtilis* spores. J. Bacteriol. 183: 6294-6301.

Kramer, M. J., and Roth, I. L. (1968) Ultrastructural differences in the exosporium of the Sterne and Vollum strains of *Bacillus anthracis*. Can J. Microbiol. 14: 1297-1299.

Little, S. F., and Knudson, G. B. (1986) Comparative efficacy of *Bacillus anthracis* live spore vaccine and protective antigen vaccine against anthrax in the guinea pig. Infec. Immun. 30 52: 509-512.

Mauriello, E. M., Due, L. H., Isticato, R., Cangiano, G., Hong, H. A., De Felice, M., Ricca, E., and Cutting, S. M. (2004) Display of heterologous antigens on the *Bacillus subtilis* spore coat using CotC as a fusion partner. Vaccine 22: 1177-1187.

Paccez, J. D., Nguyen, H. D., Luiz, W. B., Ferreira, R. C., Sbrogio-Almeida, M. E., Schuman, W., and Ferreira, L. C. (2007) Evaluation of different promoter sequences and antigen sorting signals on the immunogenicity of *Bacillus subtilis* vaccine vehicles. Vaccine 25: 4671-4680.

Raines, K. W., Kang, T. J., Hibbs, S., Cao, G. L., Weaver, J., Tsai, P., Baillie, L., Cross, A. S., and Rosen, G. M. (2006) Importance of nitric oxide synthase in the control of infection by *Bacillus anthracis*. Infect. Immun. 74: 2268-2276.

Redmond, C., Baillie, L. W., Hibbs, S., Moir, A. J., and Moir, A. (2004) Identification of proteins in the exosporium of *Bacillus anthracis*. Microbial. 150: 355-363.

Steichen, C., Chen, P., Kearney, J. P., and Turnbough, C. L. Jr. (2003) Identification of the immunodominant protein and other proteins of the *Bacillus anthracis* exosporium. J. Bacteriol. 185: 1903-1910.

Steichen, C. T., Kearney, J. P., and Turnbough, C. L. Jr. (2005) Characterization of the exosporium basal layer protein BxpB of *Bacillus anthracis*. J. Bacteriol. 187: 5868-5876.

Sullivan, M. A., Yasbin, R. E., and Young, F. E. (1984) New shuttle vectors for *Bacillus subtilis* and *Escherichia coli* which allow rapid detection of inserted fragments. Gene 29: 21-26.

Sylvestre, P., Couture-Tosi, E., and Mock, M. (2002) A collagen-like surface glycoprotein is a structural component of the *Bacillus anthracis* exosporium. Mol. Microbiol. 45: 169-178.

Sylvestre, P., Couture-Tosi, E., and Mock, M. (2003) Polymorphism in the collagen-like region of the *Bacillus anthracis* BclA protein leads to variation in exosporium filament length. J. Bacteriol. 185: 1555-1563.

Swiecki, M. K., Lisanby, M. W., Shu, F., Turnbough, C. L. Jr, and Kearney, J. P. (2006) Monoclonal antibodies for *Bacillus anthracis* spore detection and functional analyses of spore germination and outgrowth. J. Immunol. 176: 6076-6084.

Thompson, B. M., Walter, L. N., Fox, K. F., Fox, A., and Stewart, G. C. (2007) The BclB glycoprotein of *Bacillus anthracis* is involved in exosporium integrity. J. Bacteriol. 189: 6704-6713.

Thompson B M and Stewart G C. (2008) Targeting of the BclA and BclB proteins to the *Bacillus anthracis* spore surface. Mol Microbiol. 70: 421-434.

Turnbull, P. C. B. (1991) Anthrax vaccines: past, present and future. Vaccine 9: 533-539.

Waller, L. N., Stump, M. J., Fox, K. F., Harley, W. M., Fox, A., Stewart, G. C., and Shahgholi, M. (2005) Identification of a second collagen-like glycoprotein produced by *Bacillus anthracis* and demonstration of associated spore-specific sugars. J. Bacteriol. 187: 4592-4597.

Weaver, J., Kang, T. J., Raines, K. W., Cao, G. L., Hibbs, S., Tsai, P., Baillie, L., Rosen, G. M., and Cross, A. S. (2007) Protective role of *Bacillus anthracis* exosporium in macrophage-mediated killing by nitric oxide. Infect. Immun. 75:3894-3901.

Yang, F., Moss, L. G., and Phillips, G. N. Jr. (1996) The molecular structure of green fluorescent protein. Nature Biotech. 14: 1246-1251.

What is claimed is:

1. A method of producing an energy source comprising distributing to a biomass material a recombinant *Bacillus cereus* family member expressing a fusion construct, wherein the fusion construct comprises at least one molecule of interest (MOI) and:
   (a) a targeting sequence comprising amino acids 1-28 of SEQ ID NO: 10;
   (b) a targeting sequence comprising amino acids 13-28 of SEQ ID NO: 10;
   (c) a targeting sequence comprising SEQ ID NO: 10;
   (d) a targeting sequence having at least 50% identity with amino acids 13-28 of SEQ ID NO: 10, wherein the identity with amino acids 18-28 of SEQ ID NO: 10 is at least 63%; or
   (e) a targeting sequence comprising at least the first 35 amino acids of a *Bacillus* BclB protein;
   wherein expression of the fusion construct results in display of the MOI on the exosporium of the recombinant *Bacillus cereus* family member; and wherein the MOI comprises an enzyme, the enzyme comprising an oxidoreductase, a transferase, a hydrolase, a lyase, an isomerase, a ligase, a β-galactosidase, a lipase, a hydrogenase, a laccase, a redox enzyme, or an enzyme capable of hydrolyzing starch, sucrose, lactose, cellulose, or hemicellulose into fermentable sugars.

2. The method of claim 1, wherein the recombinant *Bacillus cereus* family member is selected from the group consisting of strains of *B. anthracis, B. cereus, B. thuringiensis*, and combinations thereof.

3. The method of claim 2, wherein the recombinant *Bacillus cereus* family member comprises *B. thuringiensis*.

4. The method of claim 1, wherein the enzyme comprises a lipase.

5. The method of claim 1, wherein the MOI is physically attached to the exosporium of the recombinant *Bacillus cereus* family member.

6. The method of claim 1, wherein the fusion construct is expressed under the control of a BclA promoter.

7. The method of claim 1, further comprising inactivating the *Bacillus cereus* family member prior to distribution to the biomass material.

8. The method of claim 1, wherein the enzyme comprises an enzyme capable of hydrolyzing cellulose into fermentable sugars.

9. The method of claim 1, wherein the targeting sequence comprises amino acids 1-28 of SEQ ID NO: 10.

10. The method of claim 1, wherein the targeting sequence comprises amino acids 13-28 of SEQ ID NO: 10.

11. The method of claim 1, wherein the targeting sequence comprises SEQ ID NO: 10.

12. The method of claim 1, wherein the targeting sequence has at least 50% identity with amino acids 13-28 of SEQ ID NO: 10, wherein the identity with amino acids 18-28 of SEQ ID NO: 10 is at least 63%.

13. The method of claim 1, wherein the targeting sequence comprises at least the first 35 amino acids of a *Bacillus* BclB protein.

14. The method of claim 1, wherein the enzyme comprises an oxidoreductase.

15. The method of claim 1, wherein the enzyme comprises a transferase.

16. The method of claim 1, wherein the enzyme comprises a hydrolase.

17. The method of claim 1, wherein the enzyme comprises a lyase.

18. The method of claim 1, wherein the enzyme comprises an isomerase.

19. The method of claim 1, wherein the enzyme comprises a ligase.

20. The method of claim 1, wherein the enzyme comprises a β-galactosidase.

21. The method of claim 1, wherein the enzyme comprises a hydrogenase.

22. The method of claim 1, wherein the enzyme comprises a laccase.

23. The method of claim 1, wherein the enzyme comprises a redox enzyme.

24. The method of claim 1, wherein the enzyme comprises an enzyme capable of hydrolyzing starch into fermentable sugars.

25. The method of claim 1, wherein the enzyme comprises an enzyme capable of hydrolyzing sucrose or lactose into fermentable sugars.

26. The method of claim 1, wherein the enzyme comprises an enzyme capable of hydrolyzing hemicellulose into fermentable sugars.

* * * * *